(12) United States Patent
Fu et al.

(10) Patent No.: US 6,436,635 B1
(45) Date of Patent: *Aug. 20, 2002

(54) SOLID PHASE SEQUENCING OF DOUBLE-STRANDED NUCLEIC ACIDS

(75) Inventors: Dong-Jing Fu, Waltham; Charles R. Cantor, Boston; Hubert Köster, Concord; Cassandra L. Smith, Boston, all of MA (US)

(73) Assignees: Boston University, Boston, MA (US); Sequenom, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/614,151

(22) Filed: Mar. 12, 1996

Related U.S. Application Data

(63) Continuation-in-part of application No. 08/420,009, filed on Apr. 11, 1995, now abandoned, which is a continuation-in-part of application No. 08/110,691, filed on Aug. 23, 1993, now Pat. No. 5,795,714, which is a continuation-in-part of application No. 07/972,012, filed on Nov. 6, 1992, now abandoned, and a continuation-in-part of application No. 08/419,994, filed on Apr. 11, 1995, now abandoned, which is a continuation-in-part of application No. 08/001,323, filed on Jan. 7, 1993, now abandoned.

(51) Int. Cl.$^7$ ............................................. C12Q 1/68
(52) U.S. Cl. ............................... 435/6; 536/23.1
(58) Field of Search ........................... 435/6; 536/23.1, 536/26.6

(56) References Cited

U.S. PATENT DOCUMENTS

| | | |
|---|---|---|
| 3,997,298 A | 12/1976 | McLafferty et al. |
| 4,442,354 A | 4/1984 | Hurst et al. |
| 4,931,639 A | 6/1990 | McLafferty |
| 5,002,867 A | 3/1991 | Macevicz |
| 5,002,868 A | 3/1991 | Jacobson et al. |
| 5,003,059 A | 3/1991 | Brennan |
| 5,064,754 A | 11/1991 | Mills |
| 5,068,176 A | 11/1991 | Vijg et al. |
| 5,073,483 A | 12/1991 | Lebacq |
| 5,106,727 A | 4/1992 | Hartley et al. |
| 5,112,734 A | 5/1992 | Kramer et al. |
| 5,112,736 A | 5/1992 | Caldwell et al. |
| 5,114,839 A | 5/1992 | Blocker |
| 5,130,538 A | 7/1992 | Fenn et al. |
| 5,135,870 A | 8/1992 | Williams et al. |
| 5,137,806 A | 8/1992 | Lamaistre et al. |
| 5,149,625 A | 9/1992 | Church et al. |
| 5,174,962 A | 12/1992 | Brennan |
| 5,202,231 A | 4/1993 | Drmanac et al. |
| 5,210,412 A | 5/1993 | Levis et al. .................. 250/288 |
| 5,219,726 A | 6/1993 | Evans |
| 5,221,518 A | 6/1993 | Mills |
| 5,240,859 A | 8/1993 | Aebersold |
| 5,246,865 A | 9/1993 | Stolowitz |
| 5,288,644 A | 2/1994 | Beavis et al. |
| 5,374,559 A | 12/1994 | Devienne |

FOREIGN PATENT DOCUMENTS

| | | |
|---|---|---|
| EP | 0360677 | 9/1989 |
| EP | 0392546 | 12/1990 |
| WO | WO89/10977 | 11/1989 |
| WO | WO89/12694 | 12/1989 |
| WO | WO90/14148 | 11/1990 |
| WO | WO94/16101 | 7/1994 |
| WO | WO94/21822 | 9/1994 |

OTHER PUBLICATIONS

"Optical Properties of Specific Complexes Between Complementary Oligoribonucleotides", Robert B. Gennis et a., *Biochemistry*, vol. 9, No. 24, 1970.

"DNA Sequencing By Hybridization: 100 Bases Read By a Non–gel based Method", Zaklina Strezoska, *Proc. Natl. Acad. Sci. USA*, vol. 88, pp. 10089–10093, Nov. 1991.

"Improved Chips for Sequencing by Hybridization", P.A. Pevzner, et al., *Journal of Biomolecular Structure & Dynamics*, vol. 9, Issue No. 2, 1991.

"A Method for DNA Sequencing By Hybridization with Oligonucleotide Matrix", K.R. Khrapko et al., *DNA Sequence—J.DNA Sequencing and Mapping*, vol. 1, pp. 375–388, 1991.

"Sequence–Selective Recognition of DNA by Strand Displacement with a Thymine–Substituted Polyamide", Peter E. Neilsen et al., *Science*, vol. 254, Dec. 1991.

Parallel Analysis Of Oligodeoxyribonucleotide (oligonucleotide interactions. I Analysis of Factors Influencing Oligonucleotide Duplex Formation, Uwe Maskos, et al. *Nucleic Acids Research*, vol. 20, No. 7, pp. 1675–1678, 1992.

(List continued on next page.)

Primary Examiner—Kenneth R. Horlick
(74) Attorney, Agent, or Firm—Stephanie L. Seidman; Heller Ehrman White & McAuliffe LLP; Paula Schaeneck

(57) ABSTRACT

This invention relates to methods for detecting and sequencing of target double-stranded nucleic acid sequences, to nucleic acid probes and arrays of probes useful in these methods, and to kits and systems which contain these probes. Useful methods involve hybridizing the nucleic acids or nucleic acids which represent complementary or homologous sequences of the target to an array of nucleic acid probes. These probe comprise a single-stranded portion, an optional double-stranded portion and a variable sequence within the single-stranded portion. The molecular weights of the hybridized nucleic acids of the set can be determined by mass spectroscopy, and the sequence of the target determined from the molecular weights of the fragments. Nucleic acids whose sequences can be determined include nucleic acids in biological samples such as patient biopsies and environmental samples. Probes may be fixed to a solid support such as a hybridization chip to facilitate automated determination of molecular weights and identification of the target sequence.

47 Claims, 34 Drawing Sheets-

OTHER PUBLICATIONS

"Analyzing and Comparing Nucleic Acid Sequences by Hybridization to Arrays of Olignucleotides: Evaluation Using Experimental Models", E.M. Southern, *Genomics*, 13, 1008–1017, 1992.

"Oligonucleotide Hybridizations of Glass Supports: A Novel Linker for Oligonucleotide Synthesis and Hybridization Properties of Oligonucleotides Synthesized in Situ," Uwe Maskos, *Nucleic Acids Research*, vol. 20, No. 7 pp. 1679–1684, 1992.

"Encoded Combinatorial Chemistry", Sydney Brenner, *Proc. Natl. Acad. Sci. USA* vol. 89, pp. 5381–5383, Jun. 1992.

"Report on the Sequencing by Hybridization Workshop", C.R. Cantor, *Genomics* 13, 1378–1383, 1992.

"1–Turple DNA Sequencing: Computer Analysis", P.A. Pevzner, *Journal of Biomolecular Structure & Dynamics*, vol. 7, Issue No. 1, pp. 063–069, 1989.

"An Oligonucleotide Hybridization Approach to DNA Sequencing", K.R. Khrapko, et al., *Federation of European Biochemical Societies*, vol. 256, No. 1,2, pp. 118–122, Oct. 1989.

"A New Method for Determining the DNA Nucleotide Sequence by Hybridization With Oligonucleotides", Y.P. Lysov, et al., Plenum Publishing Corporation, pp. 436–438, 1989.

"Rapid Detection and Sequencing of Specific In Vitro Amplified DNA Sequences Using Solid Phase Methods", J. Wahlberg, et al., *Mol. Cell. Probes*, 4(4), pp. 285–297, 1990.

"An Algorithm for the DNA Sequence Generation from K–Tuple Word Contents of the Minimal Number of Random Fragments", R. Drmanac, et al., *Journal of Biomolecular Structure & Dynamics*, vol. 8, Issue No. 5, pp. 1085–1102, 1991.

"Laboratory Methods: Reliable Hybridization of Oligonucleotides as Short as Six Nuclotides", R. Drmanac, et al., *DNA & Cell Biology*, vol. 9, No. 7, pp. 527–534, 1990.

"Review: Analytical Strategies for the Use of DNA Probes", J. Matthews, et al., *Analytical Biochemistry*, vol. 169, pp. 1–25, Feb. 1988.

"A Versatile Acid–Labile Lilnker for Modification of Synthetic Biomolecules", Gildea, et al., *Tetrahedron Letters*, vol. 31, No. 49, pp. 7095–7098, 1990.

Perspective: Analytical Biotechnology, "New Developments in Biochemical Mass Spectrometry: Electrospray Ionization", Smith, et al., *Anal. Chem.*, vol. 62, pp. 882–899, 1990.

"Electrospray Ion Sources. Another Variation on the Free–Jet Theme", Yamashita, et al., *J. Phys. Chem.*, vol. 88, pp. 4451–4459, 1984.

"Mass spectrometric tecniques in nucleic acid research", Pamela F. Crain, *Mass Spectrometry Reviews*, vol. 9, pp. 505–554, 1990.

"Negative Ion FAB Mass Spectrometric Analysis of Non–Charged Key Intermediates in Oligonucleotide Synthesis: Rapid Identification of Partially Protected Dinucleoside Monophosphates", Wolter, et al., *Biomedical & Environmental Mass Spectrometry*, vol. 14, pp. 111–116, 1987.

"Volatilization of High Molecular Weight DNA by Pulsed Laser Ablation of Frozen Aqueous Solutions", Nelson, et al., *Science*, vol. 246, pp. 1585–1587, Dec. 22, 1989.

"Electrospray ionization spectrometry of biomolecules", Jardine, *Nature*, vol. 345, No. 6277, pp. 747–748, Jun. 1990.

|  | $M^1$ | $M^2$ | $M^3$ | $M^5$ |
|---|---|---|---|---|
| Type Ia (base modified DNA) | OH | XR/Hal | OH | H |
| Type Ib (base modified RNA) | OH | XR/Hal | OH | OH |
| Type IIa (5'-modified DNA) | XR/Hal | H | OH | H |
| Type IIb (5'-modified RNA) | XR/Hal | H | OH | OH |
| Type III (3'-modified) | OH | H | OH | XR/Hal |
| Type IVa (P-modified DNA) | OH | H | XR | H |
| Type IVb (P-modified RNA) | OH | H | XR | OH |

FIG. 1B

Nucleoside Triphosphate Elongators:
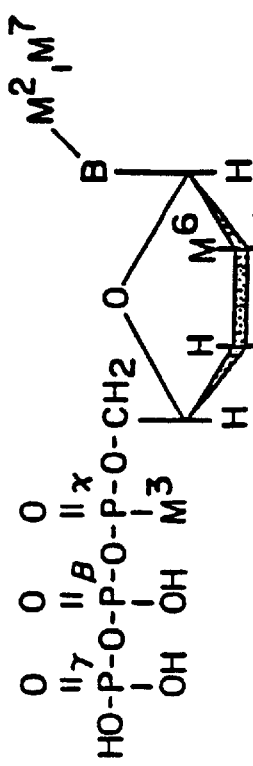
Nucleoside Triphosphate Terminators:
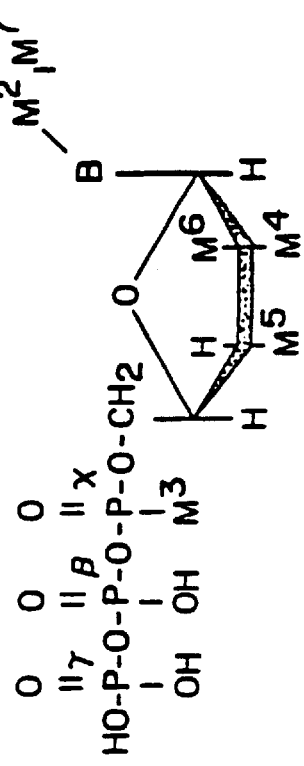
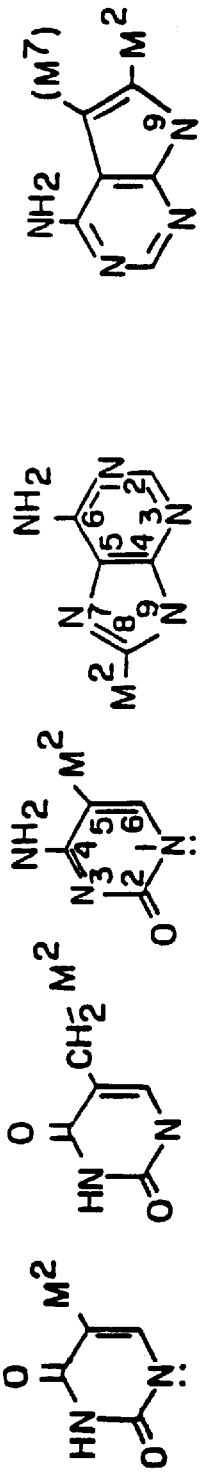
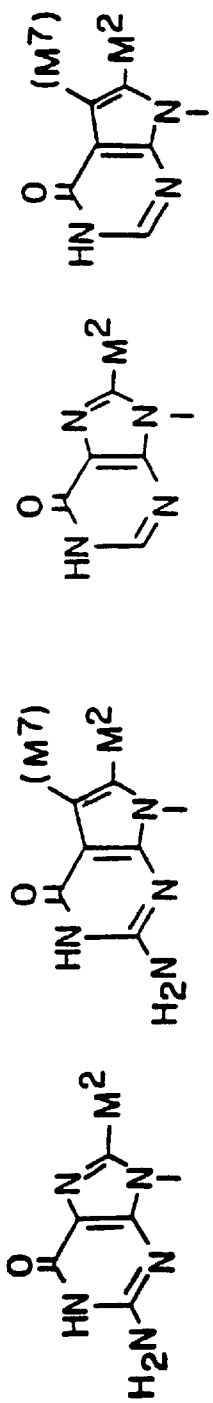
FIG. 2A

|  | $M^2$ | $M^3$ | $M^4$ | $M^5$ |
|---|---|---|---|---|
| Type A (DNA-Termination) | XR | OH | H | H |
| Type B (DNA-Termination) | H | OH | H | XR |
| Type C (DNA-Termination) | H | XR | H | H |
| Type D (RNA-Termination) | XR | OH | OH | H |
| Type E (RNA-Termination) | H | OH | OH | XR |
| Type F (RNA-Termination) | H | XR | OH | H |

Alkyl: -(CH$_2$)$_r$-CH$_3$ e.g. -CH$_3$, -C$_2$H$_5$, and branched e.g. -CH(CH$_3$)$_2$ ICH$_2$(CH$_2$)$_r$-O-H 2,3-Epoxy-1-propanol -(CH$_2$)$_m$-CH$_2$-O-H -(CH$_2$)$_m$-CH$_2$-O-Alkyl -(CH$_2$CH$_2$NH)$_m$-CH$_2$CH$_2$-NH$_2$ $-\left[\text{NH-(CH}_2)_r\text{-NH-}\underset{\underset{O}{\|}}{C}\text{-(CH}_2)_r\text{-}\underset{\underset{O}{\|}}{C}\text{-}\right]_m\text{-NH-(CH}_2)_r\text{-NH-}\underset{\underset{O}{\|}}{C}\text{-(CH}_2)_r\text{-}\underset{\underset{O}{\|}}{C}\text{-OH}$ $-\left[\text{NH-(CH}_2)_r\text{-}\underset{\underset{O}{\|}}{C}\text{-}\right]_m\text{-NH-(CH}_2)_r\text{-}\underset{\underset{O}{\|}}{C}\text{-OH}$ $-\left[\text{NH-CHY-}\underset{\underset{O}{\|}}{C}\text{-}\right]_m\text{-NH-CHY-}\underset{\underset{O}{\|}}{C}\text{-OH}$ $-\left[\text{O-(CH}_2)_r\text{-}\underset{\underset{O}{\|}}{C}\text{-}\right]_m\text{-O-(CH}_2)_r\text{-}\underset{\underset{O}{\|}}{C}\text{-OH}$

-S-

-Si(Alkyl)$_3$

-Halogen

-N$_3$

-CH$_2$F, -CHF$_2$, -CF$_3$ m = 0, 1 - 200
r = 1 - 20

FIG. 4

| NUCLEIC ACID STRUCTURE | CALCULATED $T_m$ (°C, AVERAGE BASE COMPOSITION) | | | |
|---|---|---|---|---|
| | n= 8 | 7 | 6 | 5 |
| ─────── ─── | 38 | 33 | 25 | 15 |
| ─────── `── | 33 | 25 | 15 | 3 |
| ─── ─^─ ─── | 25 | 15 | 3 | -14 |
| ─── ══ │ ── | 51 | 46 | 40 | 31 |
| ─── ══ │ ─' | 46 | 40 | 31 | 21 |
| ─── ══ `── | 40 | 31 | 21 | 11 |

FIG. 7

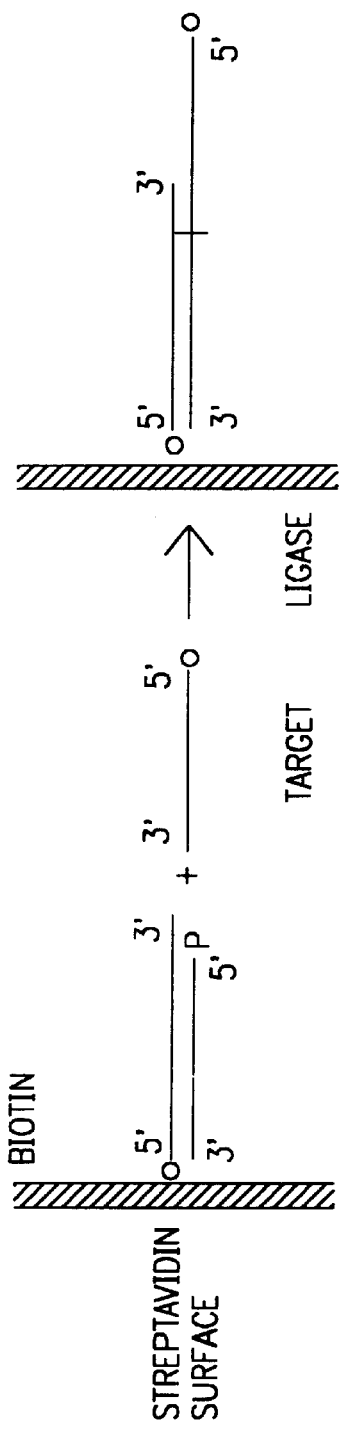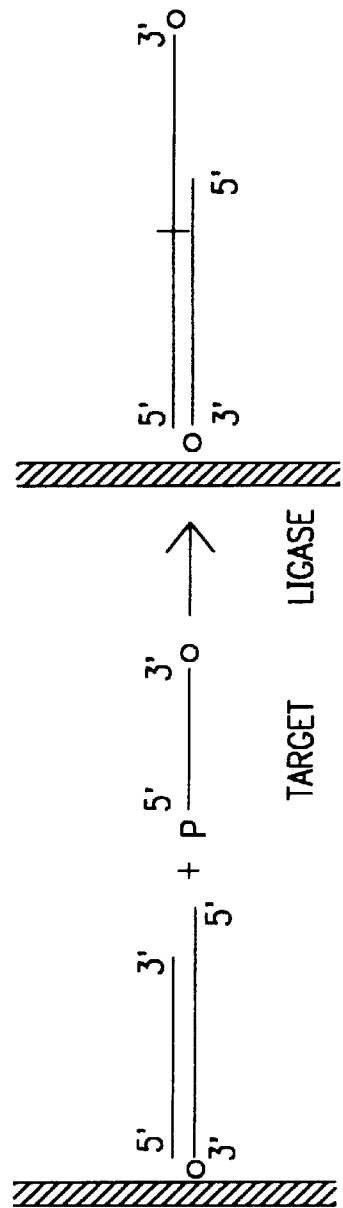
FIG. 12a
FIG. 12b

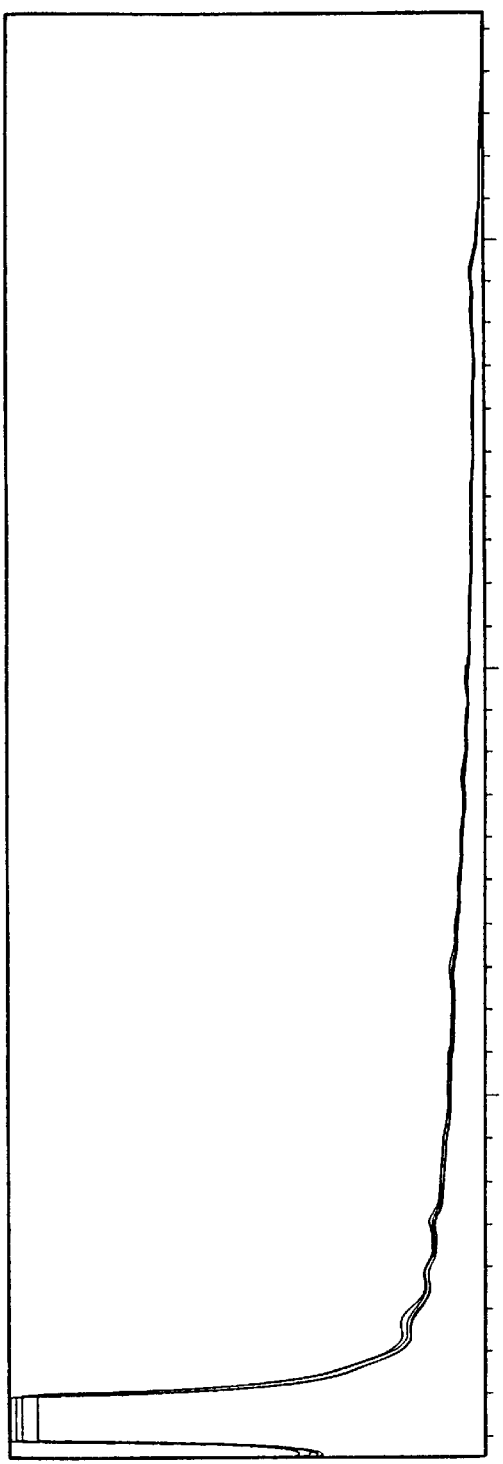
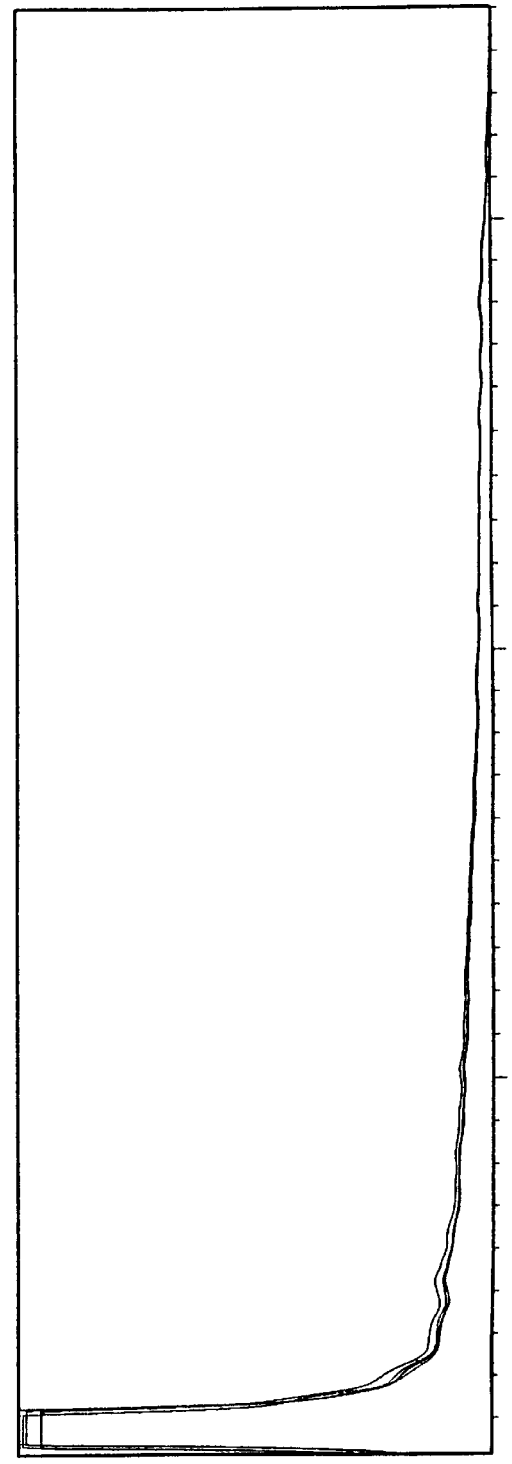
FIG. 13A
FIG. 13B

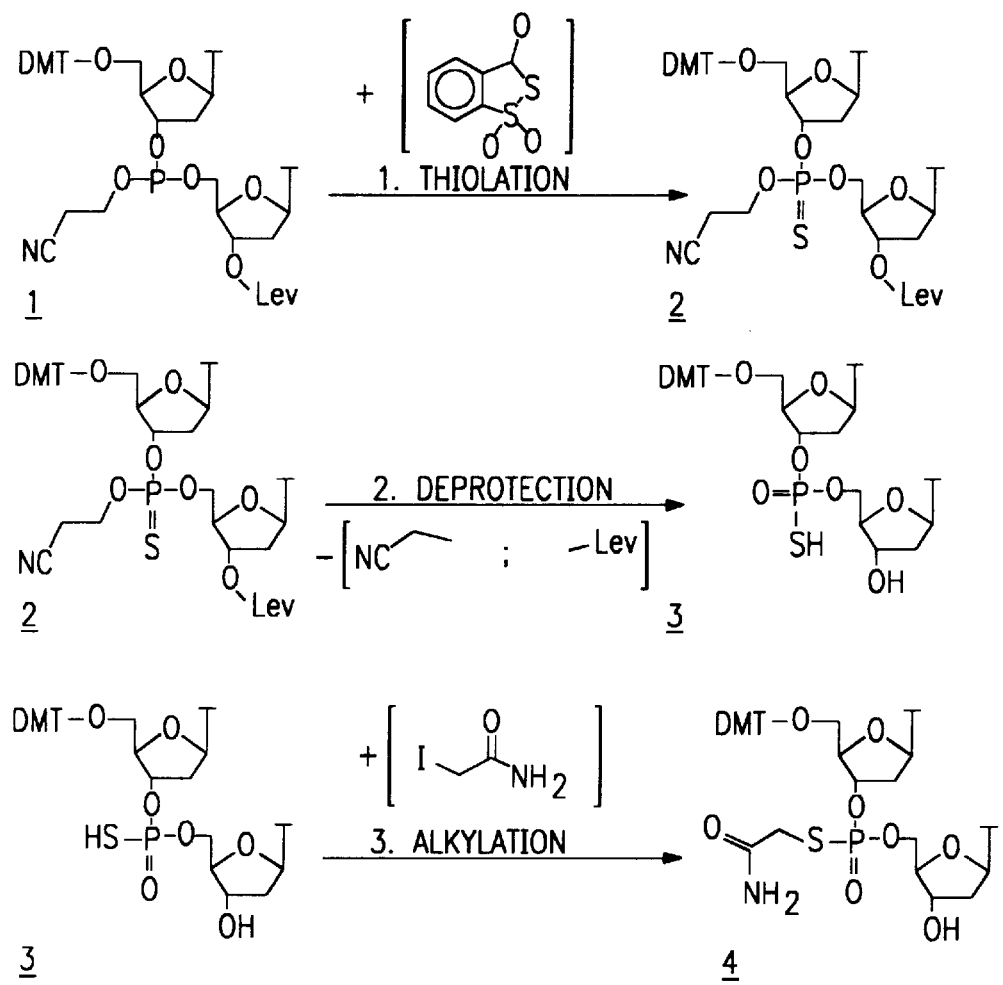
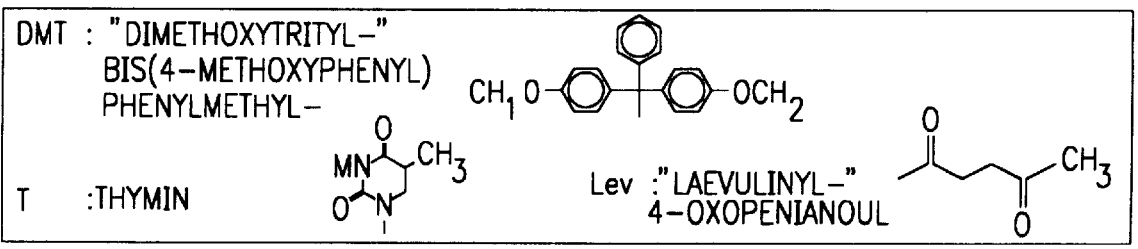
FIG. 15

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TCGAGAACCT TGGCT                                              15

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CTACTAGGCT GCGTAGTC                                         18

(2) INFORMATION FOR SEQ ID NO:3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO

```
        (v) FRAGMENT TYPE:

(vi) ORIGINAL SOURCE:

(xi) SEQUENCE DESCRIPTION: SEQ ID NO:3:

GATGATCCGA CGCATCAGAG CTC                                              23

(2) INFORMATION FOR SEQ ID NO:4:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GATGATCCGA CGCATCAGAG CTT                                              23

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GATGATCCGA CGCATCAGAG CTCT                                             24

(2) INFORMATION FOR SEQ ID NO:6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GATGATCCGA CGCATCAGAG TTCT                                             24
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

GATGATCCGA CGCATCAGAG CTA                                          23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

GATGATCCGA CGCATCAGAG CCC                                          23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

GATGATCCGA CGCATCAGAG TTC                                          23

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

GATGATCCGA CGCATCAGAA CTC                                           23

(2) INFORMATION FOR SEQ ID NO:11:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GATGATCCGA CGCATCAGAG ATC                                           23

(2) INFORMATION FOR SEQ ID NO:12:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

GATGATCCGA CGCATCAGAT ATC                                           23

(2) INFORMATION FOR SEQ ID NO:13:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

```
GATGATCCGA CGCATCAGAT ATT                                              23
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

```
GATGATCCGA CGCATCAGCT GTG                                              23
```

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

```
GATGATCCGA CGCATCACTC AAC                                              23
```

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

```
GATGATCCGA CGCATCAGAA TGT                                              23
```

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

GATGATCCGA CGCATCAGCC TAG                                              23

(2) INFORMATION FOR SEQ ID NO:18:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:18:

GATGATCCGA CGCATCAGTC GAC                                              23

(2) INFORMATION FOR SEQ ID NO:19:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:19:

GATGATCCGA CGCATCACAG CTC                                              23

(2) INFORMATION FOR SEQ ID NO:20:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:20:

GATGATCCGA CGCATCAAGG CCC                                    23

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

TTACACCGGA TCGAGCCGGG TCGATCTAG                              29

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

GGATCGACCG GGTCGATCTA G                                      21

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

AGCTGCCGGA TCGAGCCGGG TCGATCTAG                              29

(2) INFORMATION FOR SEQ ID NO:24:

(i) SEQUENCE CHARACTERISTICS:
        (A) LENGTH: 15 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

TCGAGAACCT TGGCT                                                    15

(2) INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:25:

CCGGGTCGAT CTAG                                                     14

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:26:

CCGGATCAAG CCGGGTCGAT CTAG                                          24

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:27:

TCAAGCCGGG TCGATCTAG                                                                    19

(2) INFORMATION FOR SEQ ID NO:28:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:28:

AGCCGGGTCG ATCTAG                                                                       16

(2) INFORMATION FOR SEQ ID NO:29:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:29:

GTAAAACGAC GGCCAGT                                                                      17

(2) INFORMATION FOR SEQ ID NO:30:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Genomic RNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:30:

UAAAACGACG GCCAGUG                                                                      17

(2) INFORMATION FOR SEQ ID NO:31:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: Genomic RNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:31:

UAAAACGCGG CCAGUG                                              16

(2) INFORMATION FOR SEQ ID NO:32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:32:

AACAGCTATG ACCATG                                              16

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:33:

CTGAATTAGT CAGGTTGG                                            18

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:34:

GATGATCCGA CGCATCACAT CAGTGAC                                              27

(2) INFORMATION FOR SEQ ID NO:35:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:35:

CTACTAGGCT GCGTAGTG                                                        18

(2) INFORMATION FOR SEQ ID NO:36:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:36:

GATGATCCGA CGCATCACTC CACTGTT                                              27

(2) INFORMATION FOR SEQ ID NO:37:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:37:

CTACTAGGCT GCGTAGTG                                                        18

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:38:

GATGATCCGA CGCATCACGT CAGTGTT                      27

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:39:

CTACTAGGCT GCGTAGTG                              18

(2) INFORMATION FOR SEQ ID NO:40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:40:

GATGATCCGA CGCATCACTG CAGTGGA                      27

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:41:

CTACTAGGCT GCGTAGTG                                                        18

(2) INFORMATION FOR SEQ ID NO:42:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:42:

GATGATCCGA CGCATCACGT CACTGAT                                              27

(2) INFORMATION FOR SEQ ID NO:43:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:43:

CTACTAGGCT GCGTAGTG                                                        18

(2) INFORMATION FOR SEQ ID NO:44:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:44:

GATGATCCGA CGCATCACAA CAGTGGA                                   27

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:45:

CTACTAGGCT GCGTAGTG                                             18

(2) INFORMATION FOR SEQ ID NO:46:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:46:

GATGATCCGA CGCATCACGT CAGTGGT                                   27

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:47:

CTACTAGGCT GCGTAGTC                                             18

(2) INFORMATION FOR SEQ ID NO:48:

(i) SEQUENCE CHARACTERISTICS:
        (A) LENGTH: 27 base pairs
        (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:48:

GATGATCCGA CGCATCACAA CACTGGT                                27

(2) INFORMATION FOR SEQ ID NO:49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:49:

CTACTAGGCT GCGTAGTG                                           18

(2) INFORMATION FOR SEQ ID NO:50:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:50:

GATCATCCCA GGGATCACAA GAGTGAC                                27

(2) INFORMATION FOR SEQ ID NO:51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:51:

CTACTAGGGT CCCTAGTG                                                    18

(2) INFORMATION FOR SEQ ID NO:52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:52:

GATGATCCGA CGCATCACAC CACTGAC                                          27

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:53:

CTACTAGGCT GCGTAGTG                                                    18

SOLID PHASE SEQUENCING OF DOUBLE-STRANDED NUCLEIC ACIDS

REFERENCE TO RELATED APPLICATIONS

This application is a continuation-in-part of U.S. patent application, Ser. No. 08/420,009, filed April 11, 1995, now abandoned which is a continuation-in-part of U.S. patent application, Ser. No. 08/110,691, filed Aug. 23, 1993, now U.S. Pat. No. 5,795,714 which is a continuation-in-part of U.S. patent application Ser. No. 07/972,012, filed Nov. 6, 1992 now abandoned; and U.S. patent application, Ser. No. 08/419,994, filed Apr. 11, 1995, now abandoned which is a continuation-in-part of U.S. patent application, Ser. No. 08/001,323, filed Jan. 7, 1993 now abandoned.

RIGHTS IN THE INVENTION

This invention was made with United States Government support under grant number DE-FG-02-93ER61609, awarded by the United States Department of Energy, and the United States Government has certain rights in the invention.

BACKGROUND

1. Field of the Invention

This invention relates to methods for detecting and sequencing double-stranded nucleic acids using sequencing by hybridization technology and molecular weight analysis. The invention also relates to probes and arrays useful in sequencing and detection and to kits and apparatus for determining sequence information.

2. Description of the Background

Since the recognition of nucleic acid as the carrier of the genetic code, a great deal of interest has centered around determining the sequence of that code in the many forms which it is found. Two landmark studies made the process of nucleic acid sequencing, at least with DNA, a common and relatively rapid procedure practiced in most laboratories. The first describes a process whereby terminally labeled DNA molecules are chemically cleaved at single base repetitions (A. M. Maxam and W. Gilbert, Proc. Natl. Acad. Sci. USA 74:560–64, 1977). Each base position in the nucleic acid sequence is then determined from the molecular weights of fragments produced by partial cleavages. Individual reactions were devised to cleave preferentially at guanine, at adenine, at cytosine and thymine, and at cytosine alone. When the products of these four reactions are resolved by molecular weight, using, for example, polyacrylamide gel electrophoresis, DNA sequences can be read from the pattern of fragments on the resolved gel.

The second study describes a procedure whereby DNA is sequenced using a variation of the plus-minus method (F. Sanger et al., Proc. Natl. Acad. Sci. USA 74:5463–67, 1977). This procedure takes advantage of the chain terminating ability of dideoxynucleoside triphosphates (ddNTPs) and the ability of DNA polymerase to incorporate ddNTPs with nearly equal fidelity as the natural substrate of DNA polymerase, deoxynucleosides triphosphates (dNTPs). Briefly, a primer, usually an oligonucleotide, and a template DNA are incubated together in the presence of a useful concentration of all four dNTPs plus a limited amount of a single ddNTP. The DNA polymerase occasionally incorporates a dideoxynucleotide which terminates chain extension. Because the dideoxynucleotide has no 3'-hydroxyl, the initiation point for the polymerase enzyme is lost. Polymerization produces a mixture of fragments of varied sizes, all having identical 3' termini. Fractionation of the mixture by, for example, polyacrylamide gel electrophoresis, produces a pattern which indicates the presence and position of each base in the nucleic acid. Reactions with each of the four ddNTPs allows one of ordinary skill to read an entire nucleic acid sequence from a resolved gel.

Despite their advantages, these procedures are cumbersome and impractical when one wishes to obtain megabases of sequence information. Further, these procedures are, for all practical purposes, limited to sequencing DNA. Although variations have developed, it is still not possible using either process to obtain sequence information directly from any other form of nucleic acid.

A relatively new method for obtaining sequence information from a nucleic acid has recently been developed whereby the sequences of groups of contiguous bases are determined simultaneously. In comparison to traditional techniques whereby one determines base specific information of a sequence individually, this method, referred to as sequencing by hybridization (SBH), represents a many-fold amplification in speed. Due, at least in part to the increased speed, SBH presents numerous advantages including reduced expense and greater accuracy. Two general approaches of sequencing by hybridization have been suggested and their practicality has been demonstrated in pilot studies. In one format, a complete set of $4^n$ nucleotides of length n is immobilized as an ordered array on a solid support and an unknown DNA sequence is hybridized to this array (K. R. Khrapko et al., J. DNA Sequencing and Mapping 1:375–88, 1991). The resulting hybridization pattern provides all "n-tuple" words in the sequence. This is sufficient to determine short sequences except for simple tandem repeats.

In the second format, an array of immobilized samples is hybridized with one short oligonucleotide at a time (Z. Strezoska et al., Proc. Natl. Acad. Sci. USA 88:10,089–93, 1991). When repeated $4^n$ times for each oligonucleotide of length n, much of the sequence of all the immobilized samples would be determined. In both approaches, the intrinsic power of the method is that many sequenced regions are determined in parallel. In actual practice the array size is about $10^4$ to $10^5$.

Another aspect of the method is that information obtained is quite redundant, and especially as the size of the nucleic acid probe grows. Mathematical simulations have shown that the method is quite resistant to experimental errors and that far fewer than all probes are necessary to determine reliable sequence data (P. A. Pevzner et al., J. Biomol. Struc. & Dyn. 9:399–410, 1991; W. Bains, Genomics 11:295–301, 1991).

In spite of an overall optimistic outlook, there are still a number of potentially severe drawbacks to actual implementation of sequencing by hybridization. First and foremost among these is that $4^n$ rapidly becomes quite a large number if chemical synthesis of all of the oligonucleotide probes is actually contemplated. Various schemes of automating this synthesis and compressing the products into a small scale array, a sequencing chip, have been proposed.

There is also a poor level of discrimination between a correctly hybridized, perfectly matched duplexes, and end mismatches. In part, these drawbacks have been addressed at least to a small degree by the method of continuous stacking hybridization as reported by a Khrapko et al. (FEBS Lett. 256:118–22, 1989). Continuous stacking hybridization is based upon the observation that when a single-stranded oligonucleotide is hybridized adjacent to a double-stranded oligonucleotide, the two duplexes are mutually stabilized as if they are positioned side-to-side due to a stacking contact between them. The stability of the interaction decreases significantly as stacking is disrupted by nucleotide displacement, gap or terminal mismatch. Internal mismatches are presumably ignorable because their thermodynamic stability is so much less than perfect matches. Although promising, a related problem arises which is the inability to distinguish between weak, but correct duplex formation, and simple background such as non-specific adsorption of probes to the underlying support matrix.

Detection is also monochromatic wherein separate sequential positive and negative controls must be run to discriminate between a correct hybridization match, a mismatch, and background. All to often, ambiguities develop in reading sequences longer than a few hundred base pairs on account of sequence recurrences.

For example, if a sequence one base shorter than the probe recurs three times in the target, the sequence position cannot be uniquely determined. The locations of these sequence ambiguities are called branch points.

Secondary structures often develop in the target nucleic acid affecting accessibility of the sequences. This could lead to blocks of sequences that are unreadable if the secondary structure is more stable than occurs on the complementary strand.

A final drawback is the possibility that certain probes will have nomalous behavior and for one reason or another, be recalcitrant to hybridization under whatever standard sets of conditions ultimately used. A simple example of this s the difficulty in finding matching conditions for probes rich in G/C content. A more complex example could be sequences with a high propensity to form triple helices. The only way to rigorously explore these possibilities is to carry out extensive hybridization studies with all possible oligonucleotides of length "n" under the particular format and conditions chosen. This is clearly impractical if many sets of conditions are involved.

Among the early publication which appeared discussing sequencing by hybridization, E. M. Southern (WO 89/10977), described methods whereby unknown, or target, nucleic acids are labeled, hybridized to a set of nucleotides of chosen length on a solid support, and the nucleotide sequence of the target determined, at least partially, from knowledge of the sequence of the bound fragments and the pattern of hybridization observed. Although promising, as a practical matter, this method has numerous drawbacks. Probes are entirely single-stranded and binding stability is dependent upon the size of the duplex. However, every additional nucleotide of the probe necessarily increases the size of the array by four fold creating a dichotomy which severely restricts its plausible use. Further, there is an inability to deal with branch point ambiguities or secondary structure of the target, and hybridization conditions will have to be tailored or in some way accounted for each binding event. Attempts have been made to overcome or circumvent these problems.

R. Drmanac et al. (U.S. Pat. No. 5,202,231) is directed to methods for sequencing by hybridization using sets of oligonucleotide probes with random or variable sequences. These probes, although useful, suffer from some of the same drawbacks as the methodology of Southern (1989), and like Southern, fail to recognize the advantages of stacking interactions.

K. R. Khrapko et al. (FEBS Lett. 256:118–22, 1989; and J. DNA Sequencing and Mapping 1:357–88, 1991) attempt to address some of these problems using a technique referred to as continuous stacking hybridization. With continuous stacking, conceptually, the entire sequence of a target nucleic acid can be determined. Basically, the target is hybridized to an array of probes, again single-stranded, denatured from the array, and the dissociation kinetics of denaturation analyzed to determine the target sequence. Although also promising, discrimination between matches and mis-matches (and simple background) is low and, further, as hybridization conditions are inconstant for each duplex, discrimination becomes increasingly reduced with increasing target complexity.

Another major problem with current sequencing formats is the inability to efficiently detect sequence information. In conventional procedures, individual sequences are separated by, for example, electrophoresis using capillary or slab gels. This step is slow, expensive and requires the talents of a number of highly trained individuals, and, more importantly, is prone to error. One attempt to overcome these difficulties has been to utilize the technology of mass spectrometry.

Mass spectrometry of organic molecules was made possible by the development of instruments able to volatize large varieties of organic compounds and by the discovery that the molecular ion formed by volatization breaks down into charged fragments whose structures can be related to the intact molecule. Although the process itself is relatively straight forward, actual implementation is quite complex. Briefly, the sample molecule or analyte is volatized and the resulting vapor passed into an ion chamber where it is bombarded with electrons accelerated to a compatible energy level. Electron bombardment ionizes the molecules of the sample analyte and then directs the ions formed to a mass analyzer. The mass analyzer, with its combination of electrical and magnetic fields, separates impacting ions according to their mass/charge (m/e) ratios. From these ratios, the molecular weights of the impacting ions can be determined and the structure and molecular weight of the analyte determined. The entire process requires less than about 20 microseconds.

Attempts to apply mass spectrometry to the analysis of biomolecules such as proteins and nucleic acids have been disappointing. Mass spectrometric analysis has traditionally been limited to molecules with molecular weights of a few thousand daltons. At higher molecular weights, samples become increasingly difficult to volatize and large polar molecules generally cannot be vaporized without catastrophic consequences. The energy requirement is so significant that the molecule is destroyed or, even worse, fragmented. Mass spectra of fragmented molecules are often difficult or impossible to read. Fragment linking order, particularly useful for reconstructing a molecular structure, has been lost in the fragmentation process. Both signal to noise ratio and resolution are significantly negatively affected. In addition, and specifically with regard to biomolecular sequencing, extreme sensitivity is necessary to detect the single base differences between biomolecular polymers to determine sequence identity.

A number of new methods have been developed based on the idea that heat, if applied with sufficient rapidity, will vaporize the sample biomolecule before decomposition has an opportunity to take place. This rapid heating technique is referred to as plasma desorption and there are many variations. For example, one method of plasma desorption involves placing a radioactive isotope such as Californium-252 on the surface of a sample analyte which forms a blob of plasma. From this plasma, a few ions of the sample molecule will emerge intact. Field desorption ionization, another form of desorption, utilizes strong electrostatic fields to literally extract ions from a substrate. In secondary ionization mass spectrometry or fast ion bombardment, an analyte surface is bombarded with electrons which encourage the release of intact ions. Fast atom bombardment involves bombarding a surface with accelerated ions which are neutralized by a charge exchange before they hit the surface. Presumably, neutralization of the charge lessens the probability of molecular destruction, but not the creation of ionic forms of the sample. In laser desorption, photons comprise the vehicle for depositing energy on the surface to volatize and ionize molecules of the sample. Each of these techniques has had some measure of success with different types of sample molecules. Recently, there have also been a variety of techniques and combinations of techniques specifically directed to the analysis of nucleic acids.

Brennan et al. used nuclide markers to identify terminal nucleotides in a DNA sequence by mass spectrometry (U.S. Pat. No. 5,003,059). Stable nuclides, detectable by mass spectrometry, were placed in each of the four dideoxynucleotides used as reagents to polymerize cDNA copies of the target DNA sequence. Polymerized copies were separated electrophoretically by size and the terminal nucleotide identified by the presence of the unique label.

Fenn et al. describes a process for the production of a mass spectrum containing a multiplicity of peaks (U.S. Pat. No. 5,130,538). Peak components comprised multiply charged ions formed by dispersing a solution containing an analyte into a bath gas of highly charged droplets. An electrostatic field charged the surface of the solution and dispersed the liquid into a spray referred to as an electrospray (ES) of charged droplets. This nebulization provided a high charge/mass ratio for the droplets increasing the upper limit of volatization. Detection was still limited to less than about 100,000 daltons.

Jacobson et al. utilizes mass spectrometry to analyze a DNA sequence by incorporating stable isotopes into the sequence (U.S. Pat. No. 5,002,868). Incorporation required the steps of enzymatically introducing the isotope into a strand of DNA at a terminus, electrophoretically separating the strands to determine fragment size and analyzing the separated strand by mass spectrometry. Although accuracy was stated to have been increased, electrophoresis was necessary to isolate the labeled strand.

Brennan also utilized stable markers to label the terminal nucleotides in a nucleic acid sequence, but added the step of completely degrading the components of the sample prior to analysis (U.S. Pat. Nos. 5,003,059 and 5,174,962). Nuclide markers, enzymatically incorporated into either dideoxynucleotides or nucleic acid primers, were electrophoretically separated. Bands were collected and subjected to combustion and passed through a mass spectrometer. Combustion converts the DNA into oxides of carbon, hydrogen, nitrogen and phosphorous, and the label into sulfur dioxide. Labeled combustion products were identified and the mass of the initial molecule reconstructed. Although fairly accurate, the process does not lend itself to large scale sequencing of biopolymers.

A recent advancement in the mass spectrometric analysis of high molecular weight molecules in biology has been the development of time of flight mass spectrometry (TOF-MS) with matrix-assisted laser desorption ionization (MALDI). This process involves placing the sample into a matrix which contains molecules which assist in the desorption process by absorbing energy at the frequency used to desorp the sample. The theory is that volatization of the matrix molecules encourages volatization of the sample without significant destruction. Time of flight analysis utilizes the travel time or flight time of the various ionic species as an accurate indicator of molecular mass. There have been some notable successes with these techniques.

Beavis et al. proposed to measure the molecular weights of DNA fragments in mixtures prepared by either Maxam-Gilbert or Sanger sequencing techniques (U.S. Pat. No. 5,288,644). Each of the different DNA fragments to be generated would have a common origin and terminate at a particular base along an unknown sequence. The separate mixtures would be analyzed by laser desorption time of flight mass spectroscopy to determine fragment molecular weights. Spectra obtained from each reaction would be compared using computer algorithms to determine the location of each of the four bases and ultimately, the sequence of the fragment.

Williams et al. utilized a combination of pulsed laser ablation, multiphoton ionization and time of flight mass spectrometry. Effective laser desorption was accomplished by ablating a frozen film of a solution containing sample molecules. When ablated, the film produces an expanding vapor plume which entrains the intact molecules for analysis by mass spectrometry.

Even more recent developments in mass spectrometry have further increased the upper limits of molecular weight detection and determination. Mass spectrograph systems with reflectors in the flight tube have effectively doubled resolution. Reflectors also compensate for errors in mass caused by the fact that the ionized/accelerated region of the instrument is not a point source, but an area of finite size wherein ions can accelerate at any point. Spatial differences between particle the origination points of the particles, problematic in conventional instruments because arrival times at the detector will vary, are overcome. Particles that spend more time in the accelerating field will also spend more time in the retarding field. Therefore, all particles emerging from the reflector should be synchronous, vastly improving resolution.

Despite these advances, it is still not possible to generate coordinated spectra representing a continuous sequence. Furthermore, throughput is sufficiently slow so as to make these methods impractical for large scale analysis of sequence information.

SUMMARY OF THE INVENTION

The present invention overcomes the problems and disadvantages associated with current strategies and designs and provides methods, kits and apparatus for determining the sequence of target nucleic acids.

One embodiment of the invention is directed to methods for sequencing a target nucleic acid. A set of nucleic acid fragments containing a sequence which is complementary or homologous to a sequence of the target is hybridized to an array of nucleic acid probes wherein each probe comprises a double-stranded portion, a single-stranded portion and a variable sequence within said single-stranded portion, forming a target array of nucleic acids. Molecular weights for a plurality of nucleic acids of the target array are determined and the sequence of the target constructed.

Nucleic acids of the target, the target sequence, the set and the probes may be DNA, RNA or PNA comprising purine, pyrimidine or modified bases. The probes may be fixed to a solid support such as a hybridization chip to facilitate automated determination of molecular weights and identification of the target sequence.

Another embodiment of the invention is directed to methods for sequencing a target nucleic acid. A set of nucleic acid fragments containing a sequence which is complementary or homologous to a sequence of the target is hybridized to an array of nucleic acid probes forming a target array containing a plurality of nucleic acid complexes. One strand of those probes hybridized by a fragment is extended using the fragment as a template. Molecular weights for a plurality of nucleic acids of the target array are determined and the sequence of the target constructed. Strands can be enzymatically extended using chain terminating and chain elongating nucleotides. The resulting nested set of nucleic acids represents the sequence of the target.

Another embodiment of the invention is directed to methods for detecting a target nucleic acid. A set of nucleic acids complementary to a sequence of the target, is hybridized to a fixed array of nucleic acid probes. The molecular weights of the hybridized nucleic acids are determined by mass spectrometry and a sequence of the target can be identified. Target nucleic acids may be obtained from biological samples such as patient samples wherein detection of the target is indicative of a disorder in the patient, such as a genetic defect, a neoplasm or an infection.

Another embodiment of the invention is directed to methods for sequencing a target nucleic acid. A sequence of the target is cleaved into nucleic acid fragments and the fragments hybridized to an array of nucleic acid probes. Fragments are created by enzymatically or physically cleaving the target and the sequence of the fragments is homologous with or complementary to at least a portion of the target sequence. The array is attached to a solid support and the molecular weights of the hybridized fragments determined by mass spectrometry. From the molecular weights determined, nucleotide sequences of the hybridized fragments are determined and a nucleotide sequence of the target can be identified.

Another embodiment of the invention is directed to methods for sequencing a target nucleic acid. A set of nucleic acids complementary to a sequence of the target is hybridized to an array of single-stranded nucleic acid probes wherein each probe comprises a constant sequence and a variable sequence and said variable sequence is determinable. The molecular weights of the hybridized nucleic acids are determined and the sequence of said target identified. The array comprises less than or equal to about $4^R$ different probes and R is the length in nucleotides of the variable sequence and may be attached to a solid support.

Another embodiment of the invention is directed to methods for sequencing a target nucleic acid by strand-displacement, double-stranded sequencing. A set of partially single-stranded and partially double-stranded nucleic acid fragments are provided wherein each fragment contains a sequence that corresponds to a sequence of the target. These nucleic acid fragments are hybridized to a set of partially single-stranded and partially double-stranded nucleic acid probes, via the single-stranded regions of each, to form a set of fragment/probe complexes. Prior to hybridization, either the fragments or the probes may be treated with a phosphorylase to remove phosphate groups from the 5'-termini of the nucleic acids. 5'-termini are ligated with adjacent 3'-termini of the complex forming a common single strand. The complementary unligated strand contains a nick which is recognized by a nucleic acid polymerase that initiates strand-displacement polymerization, extending the unligated strand. Polymerization proceeds, using the ligated strand as a template, in the presence of labeled nucleotides such as mass modified nucleotides. The sequence of the target can be determined by mass spectrometry from the molecular weights of the extended strands. This process can be used to sequence target nucleic acids and also to identify a single sequence in a mixed background. Selection of the species of nucleic acid to be sequenced occurs upon hybridization to the probe. As only fragments complementary to the single-stranded region of the probe will form complexes, only those fragments complexes are sequenced.

Another embodiment of the invention is directed to arrays of nucleic acid probes. In these arrays, each probe comprises a first strand and a second strand wherein the first strand is hybridized to the second strand forming a double-stranded portion, a single-stranded portion and a variable sequence within the single-stranded portion. The array may be attached to a solid support such as a material that facilitates volatization of nucleic acids for mass spectrometry. Arrays can be fixed to hybridization chips containing less than or equal to about $4^R$ different probes wherein R is the length in nucleotides of the variable sequence. Arrays can be used in detection methods and in kits to detect nucleic acid sequences which may be indicative of a disorder and in sequencing systems such as sequencing by mass spectrometry.

Another embodiment of the invention is directed to arrays of single-stranded nucleic acid probes wherein each probe of the array comprises a constant sequence and a variable sequence which is determinable. Arrays may be attached to solid supports which comprise matrices that facilitate volatization of nucleic acids for mass spectrometry. Arrays, generated by conventional processes, may be characterized using the above methods and replicated in mass for use in nucleic acid detection and sequencing systems.

Another embodiment of the invention is directed to kits for detecting a sequence of a target nucleic acid. Kits contain arrays of nucleic acid probes fixed to a solid support wherein each probe comprises a double-stranded portion, a single-stranded portion and a variable sequence within said single-stranded portion. The solid support may be, for example, coated with a matrix that facilitates volatization of nucleic acids for mass spectrometry such as an aqueous composition.

Another embodiment of the invention is directed to mass spectrometry systems for the rapid sequencing of nucleic acids. Systems comprise a mass spectrometer, a computer with appropriate software and probe arrays which can be used to capture and sort nucleic acid sequences for subsequent analysis by mass spectrometry.

Other embodiments and advantages of the invention are set forth, in part, in the description which follows and, in part, will be obvious from this description and may be learned from the practice of the invention.

DESCRIPTION OF THE DRAWINGS

FIG. 4 List of mass modification moieties.

FIG. 7 Calculated $T_m$ of matched and mismatched complementary DNA.

FIG. 12 (A) Ligation of target DNA with probe attached at 5'-terminus; and (B) ligation of target DNA with probe attached at the 3'-terminus.

FIG. 15 Schematic of mass modification by alkylation.

DESCRIPTION OF THE INVENTION

Figure 1A:
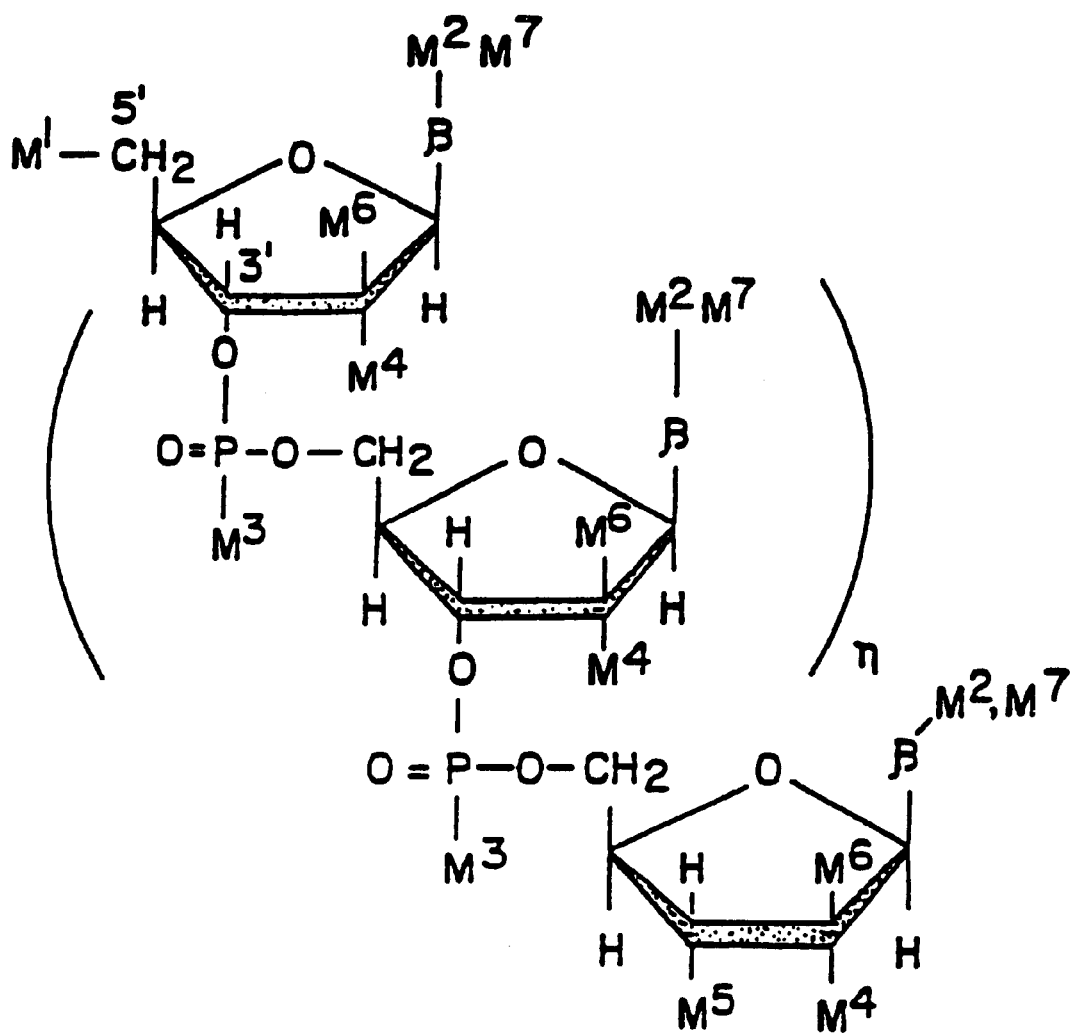
FIG. 1 (A) Schematic of a mass modified nucleic acid primer; and (B) primer mass modification moieties.

As embodied and broadly described herein, the present invention is directed to methods for sequencing a nucleic acid, probe arrays useful for sequencing by mass spectrometry and kits and systems which comprise these arrays.

Nucleic acid sequencing, on both a large and small scale, is critical to many aspects of medicine and biology such as, for example, in the identification, analysis or diagnosis of diseases and disorders, and in determining relationships between living organisms. Conventional sequencing techniques rely on a base-by-base identification of the sequence using electrophoresis in a semi-solid such as an agarose or polyacrylamide gel to determine sequence identity. Although attempts have been made to apply mass spectrometric analysis to these methods, the two processes are not well suited because, at least in part, information is still be gathered in a single base format. Sequencing-by-hybridization methodology has enhanced the sequencing process and provided a more optimistic outlook for more rapid sequencing techniques, however, this methodology is no more applicable to mass spectrometry than traditional sequencing techniques.

In contrast, positional sequencing by hybridization (PSBH) with its ability to stably bind and discriminate different sequences with large or small arrays of probes is well suited to mass spectrometric analysis. Sequence information is rapidly determined in batches and with a minimum of effort. Such processes can be used for both sequencing unknown nucleic acids and for detecting known sequences whose presence may be an indicators of a disease or contamination. Additionally, these processes can be utilized to create coordinated patterns of probe arrays with known sequences. Determination of the sequence of fragments hybridized to the probes also reveals the sequence of the probe. These processes are currently not possible with conventional techniques and, further, a coordinated batch-type analysis provides a significant increase in sequencing speed and accuracy which is expected to be required for effective large scale sequencing operations.

PSBH is also well suited to nucleic acid analysis wherein sequence information is not obtained directly from hybridization. Sequence information can be learned by coupling PSBH with techniques such as mass spectrometry. Target nucleic acid sequences can be hybridized to probes or array of probes as a method of sorting nucleic acids having distinct sequences without having a priori knowledge of the sequences of the various hybridization events. As each probe will be represented as multiple copies, it is only necessary that hybridization has occurred to isolate distinct sequence packages. In addition, as distinct packages of sequences, they can be amplified, modified or otherwise controlled for subsequent analysis. Amplification increases the number of specific sequences which assists in any analysis requiring increased quantities of nucleic acid while retaining sequence specificity. Modification may involve chemically altering the nucleic acid molecule to assist with later or downstream analysis.

Consequently, another important feature of the invention is the ability to simply and rapidly mass modify the sequences of interest. A mass modification is an alteration in the mass, typically measured in terms of molecular weight as daltons, of a molecule. Mass modification which increase the discrimination between at least two nucleic acids with single base differences in size or sequence can be used to facilitate sequencing using, for example, molecular weight determinations.

One embodiment of the invention is directed to a method for sequencing a target nucleic acid using mass modified nucleic acids and mass spectrometry technology. Target nucleic acids which can be sequenced include sequences of deoxyribonucleic acid (DNA) or ribonucleic acid (RNA). Such sequences may be obtained from biological, recombinant or other man-made sources, or purified from a natural source such as a patient's tissue or obtained from environmental sources. Alternate types of molecules which can be sequenced includes polyamide nucleic acid (PNA) (P. E. Nielsen et al., Sci. 254:1497–1500, 1991) or any sequence of bases joined by a chemical backbone that have the ability to base pair or hybridize with a complementary chemical structure.

The bases of DNA, RNA and PNA include purines, pyrimidines and purine and pyrimidine derivatives and modifications, which are linearly linked to a chemical backbone. Common chemical backbone structures are deoxyribose phosphate, ribose phosphate, and polyamide. The purines of both DNA and RNA are adenine (A) and guanine (G). Others that are known to exist include xanthine, hypoxanthine, 2- and 1-diaminopurine, and other more modified bases. The pyrimidines are cytosine (C), which is common to both DNA and RNA, uracil (U) found predominantly in RNA, and thymidine (T) which occurs almost exclusively in DNA. Some of the more atypical pyrimidines include methylcytosine, hydroxymethyl-cytosine, methyluracil, hydroxymethyluracil, dihydroxypentyluracil, and other base modifications. These bases interact in a complementary fashion to form base-pairs, such as, for example, guanine with cytosine and adenine with thymidine. This invention also encompasses situations in which there is non-traditional base pairing such as Hoogsteen base pairing which has been identified in certain tRNA molecules and postulated to exist in a triple helix.

Sequencing involves providing a nucleic acid sequence which is homologous or complementary to a sequence of the target. Sequences may be chemically synthesized using, for example, phosphoramidite chemistry or created enzymatically by incubating the target in an appropriate buffer with chain elongating nucleotides and a nucleic acid polymerase. Initiation and termination sites can be controlled with dideoxynucleotides or oligonucleotide primers, or by placing coded signals directly into the nucleic acids. The sequence created may comprise any portion of the target sequence or the entire sequence. Alternatively, sequencing may involve elongating DNA in the presence of boron derivatives of nucleotide triphosphates. Resulting double-stranded samples are treated with a 3' exonuclease such as exonuclease III. This exonuclease stops when it encounters a boronated residue thereby creating a sequencing ladder.

Nucleic acids can also be purified, if necessary to remove substances which could be harmful (e.g. toxins), dangerous (e.g. infectious) or might interfere with the hybridization reaction or the sensitivity of that reaction (e.g. metals, salts, protein, lipids). Purification may involve techniques such as chemical extraction with salts, chloroform or phenol, sedimentation centrifugation, chromatography or other techniques known to those of ordinary skill in the art.

If sufficient quantities of target nucleic acid are available and the nucleic acids are sufficiently pure or can be purified so that any substances which would interfere with hybridization are removed, a plurality of target nucleic acids may be directly hybridized to the array. Sequence information can be obtained without creating complementary or homologous copies of a target sequence.

Sequences may also be amplified, if necessary or desired, to increase the number of copies of the target sequence using, for example, polymerase chain reactions (PCR) technology or any of the amplification procedures. Amplification involves denaturation of template DNA by heating in the presence of a large molar excess of each of two or more oligonucleotide primers and four dNTPs (dGTP, dCTP, dATP, dTTP). The reaction mixture is cooled to a temperature that allows the oligonucleotide primer to anneal to target sequences, after which the annealed primers are extended with DNA polymerase. The cycle of denaturation, annealing, and DNA synthesis, the principal of PCR amplification, is repeated many times to generate large quantities of product which can be easily identified.

The major product of this exponential reaction is a segment of double stranded DNA whose termini are defined by the 5' termini of the oligonucleotide primers and whose length is defined by the distance between the primers. Under normal reaction conditions, the amount of polymerase becomes limiting after 25 to 30 cycles or about one million fold amplification. Further, amplification is achieved by diluting the sample 1000 fold and using it as the template for further rounds of amplification in another PCR. By this method, amplification levels of $10^9$ to $10^{10}$ can be achieved during the course of 60 sequential cycles. This allows for the detection of a single copy of the target sequence in the presence of contaminating DNA, for example, by hybridization with a radioactive probe. With the use of sequential PCR, the practical detection limit of PCR can be as low as 10 copies of DNA per sample.

Although PCR is a reliable method for amplification of target sequences, a number of other techniques can be used such as ligase chain reaction, self sustained sequence replication, Qβ replicase amplification, polymerase chain reaction linked ligase chain reaction, gapped ligase chain reaction, ligase chain detection and strand displacement amplification. The principle of ligase chain reaction is based in part on the ligation of two adjacent synthetic oligonucleotide primers which uniquely hybridize to one strand of the target DNA or RNA. If the target is present, the two oligonucleotides can be covalently linked by ligase. A second pair of primers, almost entirely complementary to the first pair of primers is also provided. The template and the four primers are placed into a thermocycler with a thermostable ligase. As the temperature is raised and lowered, oligonucleotides are renatured immediately adjacent to each other on the template and ligated. The ligated product of one reaction serves as the template for a subsequent round of ligation. The presence of target is manifested as a DNA fragment with a length equal to the sum of the two adjacent oligonucleotides.

Target sequences are fragmented, if necessary, into a plurality of fragments using physical, chemical or enzymatic means to create a set of fragments of uniform or relatively uniform length. Preferably, the sequences are enzymatically cleaved using nucleases such as DNases or RNases (mung bean nuclease, micrococcal nuclease, DNase I, RNase A, RNase T1), type I or II restriction endonucleases, or other site-specific or non-specific endonucleases. Sizes of nucleic acid fragments are between about 5 to about 1,000 nucleotides in length, preferably between about 10 to about 200 nucleotides in length, and more preferably between about 12 to about 100 nucleotides in length. Sizes in the range of about 5, 10, 12, 15, 18, 20, 24, 26, 30 and 35 are useful to perform small scale analysis of short regions of a nucleic acid target. Fragment sizes in the range of 25, 50, 75, 125, 150, 175, 200 and 250 nucleotides and larger are useful for rapidly analyzing larger target sequences.

Target sequences may also be enzymatically synthesized using, for example, a nucleic acid polymerase and a collection of chain elongating nucleotides (NTPs, dNTPs) and limiting amounts of chain terminating (ddNTPs) nucleotides. This type of polymerization reaction can be controlled by varying the concentration of chain terminating nucleotides to create sets, for example nested sets, which span various size ranges. In a nested set, fragments will have common one terminus and one terminus which will be different between the members of the set such that the larger fragments will contain the sequences of the smaller fragments.

The set of fragments created, which may be either homologous or complementary to the target sequence, is hybridized to an array of nucleic acid probes forming a target array of nucleic acid probe/fragment complexes. An array constitutes an ordered or structured plurality of nucleic acids which may be fixed to a solid support or in liquid suspension. Hybridization of the fragments to the array allows for sorting of very large collections of nucleic acid fragments into identifiable groups. Sorting does not require a priori knowledge of the sequences of the probes, and can greatly facilitate analysis by, for example, mass spectrophotometric techniques.

Hybridization between complementary bases of DNA, RNA, PNA, or combinations of DNA, RNA and PNA, occurs under a wide variety of conditions such as variations in temperature, salt concentration, electrostatic strength, and buffer composition. Examples of these conditions and methods for applying them are described in *Nucleic Acid Hybridization: A Practical Approach* (B. D. Hames and S. J.

Higgins, editors, IRL Press, 1985). It is preferred that hybridization takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. For example, typical hybridization conditions for a mixture of two 20-mers is to bring the mixture to 68° C. and let cool to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Examples of other reagents and chemicals include divalent ions, polyvalent ions and intercalating substances such as ethidium bromide, actinomycin D, psoralen and angelicin.

Optionally, hybridized target sequences may be ligated to a single-strand of the probes thereby creating ligated target-probe complexes or ligated target arrays. Ligation of target nucleic acid to probe increases fidelity of hybridization and allows for incorrectly hybridized target to be easily washed from correctly hybridized target. More importantly, the addition of a ligation step allows for hybridizations to be performed under a single set of hybridization conditions. Variation of hybridization conditions due to base composition are no longer relevant as nucleic acids with high A/T or G/C content ligate with equal efficiency. Consequently, discrimination is very high between matches and mismatches, much higher than has been achieved using other methodologies wherein the effects of G/C content were only somewhat neutralized in high concentrations of quaternary or tertiary amines such as, for example, 3M tetramethyl ammonium chloride. Further, hybridization conditions such as temperatures of between about 22° C. to about 37° C., salt concentrations of between about 0.05 M to about 0.5 M, and hybridization times of between about less than one hour to about 14 hours (overnight), are also suitable for ligation. Ligation reactions can be accomplished using a eukaryotic derived or a prokaryotic derived ligase such as T4 DNA or RNA ligase. Methods for use of these and other nucleic acid modifying enzymes are described in *Current Protocols in Molecular Biology* (F. M. Ausubel et al., editors, John Wiley & Sons, 1989).

Each probe of the probe array comprises a single-stranded portion, an optional double-stranded portion and a variable sequence within the single-stranded portion. These probes may be DNA, RNA, PNA, or any combination thereof, and may be derived from natural sources or recombinant sources, or be organically synthesized. Preferably, each probe has one or more double stranded portions which are about 4 to about 30 nucleotides in length, preferably about 5 to about 15 nucleotides and more preferably about 7 to about 12 nucleotides, and may also be identical within the various probes of the array, one or more single stranded portions which are about 4 to 20 nucleotides in length, preferably between about 5 to about 12 nucleotides and more preferably between about 6 to about 10 nucleotides, and a variable sequence within the single stranded portion which is about 4 to 20 nucleotides in length and preferably about 4, 5, 6, 7 or 8 nucleotides in length. Overall probe sizes may range from as small as 8 nucleotides in lengths to 100 nucleotides and above. Preferably, sizes are from about 12 to about 35 nucleotides, and more preferably, from about 12 to about 25 nucleotides in length.

Probe sequences may be partly or entirely known, determinable or completely unknown. Known sequences can be created, for example, by chemically synthesizing individual probes with a specified sequence at each region. Probes with determinable variable regions may be chemically synthesized with random sequences and the sequence information determined separately. Either or both the single-stranded and the double-stranded regions may comprise constant sequences such as, for example, when an area of the probe or hybridized nucleic acid would benefit from having a constant sequence as a point of reference in subsequent analyses.

An advantage of this type of probe is in its structure. Hybridization of the target nucleic acid is encouraged due to the favorable thermodynamic conditions, including base-stacking interactions, established by the presence of the adjacent double strandedness of the probe. Probes may be structured with terminal single-stranded regions which consist entirely or partly of variable sequences, internal single-stranded regions which contain both constant and variable regions, or combinations of these structures. Preferably, the probe has a single-stranded region at one terminus and a double-stranded region at the opposite terminus.

Fragmented target sequences, preferably, will have a distribution of terminal sequences sufficiently broad so that the nucleotide sequence of the hybridized fragments will include the entire sequence of the target nucleic acid. Consequently, the typical probe array will comprise a collection of probes with sufficient sequence diversity in the variable regions to hybridize, with complete or nearly complete discrimination, all of the target sequence or the target-derived sequences. The resulting target array will comprise the entire target sequence on strands of hybridized probes. By way of example only, if the variable portion consisted of a four nucleotide sequence (R=4) of adenine, guanine, thymine, and cytosine, the total number of possible combinations ($4^R$) would be $4^4$ or 256 different nucleic acid probes. If the number of nucleotides in the variable sequence was five, the number of different probes within the set would be $4^5$ or 1,024. In addition, it is also possible to utilize probes wherein the variable nucleotide sequence contains gapped segments, or positions along the variable sequence which will base pair with any nucleotide or at least not interfere with adjacent base pairing.

A nucleic acid strand of the target array may be extended or elongated enzymatically. Either the hybridized fragment or one or the other of the probe strands can be extended. Extension reactions can utilize various regions of the target array as a template. For example, when fragment sequences are longer than the hybridizable portion of a probe having a 3' single-stranded terminus, the probe will have a 3' overhang and a 5' overhang after hybridization of the fragment. The now internal 3' terminus of the one strand of the probe can be used as a primer to prime an extension reaction using, for example, an appropriate nucleic acid polymerase and chain elongating nucleotides. The extended strand of the probe will contain sequence information of the entire hybridized fragment. Reaction mixtures containing dideoxynucleotides will create a set of extended strands of varying lengths and, preferably, a nested set of strands. As the fragments have been initially sorted by hybridization to the array, each probe of the array will contain sets of nucleic acids that represent each segment of the target sequence. Base sequence information can be determined from each extended probe. Compilation of the sequence information from the array, which may require computer assistance with very large arrays, will allow one to determine the sequence of the target. Depending on the structure of the probe (e.g. 5' overhang, 3' overhang, internal single-stranded region), strands of the probe or strands of hybridized nucleic acid containing target sequence can also be enzymatically amplified by, for example, single primer PCR reactions. Variations of this process may involve aspects of strand displacement amplification, Qβ replicase amplification, self-sustained sequence replication amplification and any of the various polymerase chain reaction amplification technologies.

Figure 3:
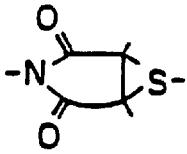
FIG. 3 List of mass modification moieties.

Extended nucleic acid strands of the probe can be mass modified using a variety of techniques and methodologies. The most straight forward may be to enzymatically synthesize the extension utilizing a polymerase and nucleotide reagents, such as mass modified chain elongating and chain terminating nucleotides. Mass modified nucleotides incorporate into the growing nucleic acid chain. Mass modifications may be introduced in most sites of the macromolecule which do not interfere with the hydrogen bonds required for base pair formation during nucleic acid hybridization. Typical modifications include modification of the heterocyclic bases, modifications of the sugar moiety (ribose or deoxyribose), and modifications of the phosphate group. Specifically, a modifying functionality, which may be a chemical moiety, is placed at or covalently coupled to the C2, N3, N7 or N8 positions of purines, or the N7 or N9 positions of deazapurines. Modifications may also be placed at the C5 or C6 positions of pyrimidines (e.g. FIGS. 1A, 1B, 2A and 2B). Examples of useful modifying groups include deuterium, F, Cl, Br, I, biotin, fluorescein, iododicarbocyanine dye, SiR, $Si(CH_3)_3$, $Si(CH_3)_2(C_2H_5)$, $Si(CH_3)_2(C_2H_5)_2$, $Si(CH_3)(C_2H_5)_2$, $Si(C_2H_5)_3$, $(CH_2)_nCH_3$, $(CH_2)_nNR$, $CH_2CONR$, $(CH_2)_nOH$, $CH_2F$, $CHF_2$ and $CF_3$; wherein n is an integer and R is selected from the group consisting of —H, deuterium and alkyls, alkoxys and aryls of 1–6 carbon atoms, polyoxymethylene, monoalkylated polyoxymethylene, polyethylene imine, polyamide, polyester, alkylated silyl, hetero-oligo/polyaminoacid and polyethylene glycol (FIGS. 3 and 4).

Mass modifying functionalities may also be generated from a precursor functionality such as $-N_3$ or —XR, wherein X is: —OH, $-NH_2$, —NHR, —SH, —NCS, $-OCO(CH_2)_nCOOH$, $-NHCO(CH_2)_nCOOH$, $-OSO_2OH$, $-OCO(CH_2)_nI$ or $-OP(O-alkyl)-N-(alkyl)_2$, and n is an integer from 1 to 20; and R is: —H, deuterium and alkyls, alkoxys or aryls of 1–6 carbon atoms, such as methyl, ethyl, propyl, isopropyl, t-butyl, hexyl, benzyl, benzhydral, trityl, substituted trityl, aryl, substituted aryl, polyoxymethylene, monoalkylated polyoxymethylene, polyethylene imine, polyamide, polyester, alkylated silyl, heterooligo/polyaminoacid or polyethylene glycol. These and other mass modifying functionalities which do not interfere with hybridization can be attached to a nucleic acids either alone or in combination. Preferably, combinations of different mass modifications are utilized to maximize distinctions between nucleic acids having different sequences.

Mass modifications may be major changes of molecular weight, such as occurs with coupling between a nucleic acid and a heterooligo/polyaminoacid, or more minor such as occurs by substituting chemical moieties into the nucleic acid having molecular masses smaller than the natural moiety. Non-essential chemical groups may be eliminated or modified using, for example, an alkylating agent such as iodoacetamide. Alkylation of nucleic acids with iodoacetamide has an additional advantage that a reactive oxygen of the 3'-position of the sugar is eliminated. This provides one less site per base for alkali cations, such as sodium, to interact. Sodium, present in nearly all nucleic acids, increases the likelihood of forming satellite adduct peaks upon ionization. Adduct peaks appear at a slightly greater mass than the true molecule which would greatly reduce the accuracy of molecular weight determinations. These problems can be addressed, in part, with matrix selection in mass spectrometric analysis, but this only helps with nucleic acids of less than 20 nucleotides. Ammonium ($^+NH_3$), which can substitute for the sodium cation ($^+Na$) during ion exchange, does not increase adduct formation. Consequently, another useful mass modification is to remove alkali cations from the entire nucleic acid. This can be accomplished by ion exchange with aqueous solutions of ammonium such as ammonium acetate, ammonium carbonate, diammonium hydrogen citrate, ammonium tartrate and combinations of these solutions. DNA dissolved in 3 M aqueous ammonium hydroxide neutralizes all the acidic functions of the molecule. As there are no protons, there is a significant reduction in fragmentation during procedures such as mass spectrometry.

Another mass modification is to utilize nucleic acids with non-ionic polar phosphate backbones (e.g. PNA). Such nucleotides can be generated by oligonucleoside phosphomonothioate diesters or by enzymatic synthesis using nucleic acid polymerases and alpha- (α-) thio nucleoside triphosphate and subsequent alkylation with iodoacetamide. Synthesis of such compounds is straight forward and can be performed and the products separated and isolated by, for example, analytical HPLC.

Mass modification of arrays can be performed before or after target hybridization as the modification do not interfere with hybridization of or hybridized nucleic. This conditioning of the array is simply to perform and easily adaptable in bulk. Probe arrays can therefore be synthesized with no special manipulations. Only after the arrays are fixed to solid supports, just in fact when it would be most convenient to perform mass modification, would probes be conditioned.

Probe strands may also be mass modified subsequent to synthesis by, for example, contacting by treating the extended strands with an alkylating agent, a thiolating agent or subjecting the nucleic acid to cation exchange. Nucleic acid which can be modified include target sequences, probe sequences and strands, extended strands of the probe and other available fragments. Probes can be mass modified on either strand prior to hybridization. Such arrays of mass modified or conditioned nucleic acids can be bound to fragments containing the target sequence with no interference to the fidelity of hybridization. Subsequent extension of either strand of the probe, for example using Sanger sequencing techniques, and using the target sequences as templates will create mass modified extended strands. The molecular weights of these strands can be determined with excellent accuracy.

Probes may be in solution, such as in wells or on the surface of a micro-tray, or attached to a solid support. Mass modification can occur while the probes are fixed to the support, prior to fixation or upon cleavage from the support which can occur concurrently with ablation when analyzed by mass spectrometry. In this regard, it can be important which strand is released from the support upon laser ablation. Preferably, in such cases, the probe is differentially attached to the support. One strand may be permanent and the other temporarily attached or, at least, selectively releasable.

Examples of solid supports which can be used include a plastic, a ceramic, a metal, a resin, a gel and a membrane.

Useful types of solid supports include plates, beads, microbeads, whiskers, combs, hybridization chips, membranes, single crystals, ceramics and self-assembling monolayers. A preferred embodiment comprises a two-dimensional or three-dimensional matrix, such as a gel or hybridization chip with multiple probe binding sites (Pevzner et al., J. Biomol. Struc. & Dyn. 9:399–410, 1991; Maskos and Southern, Nuc. Acids Res. 20:1679–84, 1992). Hybridization chips can be used to construct very large probe arrays which are subsequently hybridized with a target nucleic acid. Analysis of the hybridization pattern of the chip can assist in the identification of the target nucleotide sequence. Patterns can be manually or computer analyzed, but it is clear that positional sequencing by hybridization lends itself to computer analysis and automation. Algorithms and software have been developed for sequence reconstruction which are applicable to the methods described herein (R. Drmanac et al., J. Biomol. Struc. & Dyn. 5:1085–1102, 1991; P. A. Pevzner, J. Biomol. Struc. & Dyn. 7:63–73, 1989).

Nucleic acid probes may be attached to the solid support by covalent binding such as by conjugation with a coupling agent or by, covalent or non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (T. Sano and C. R. Cantor, Bio/Technology 9:1378–81, 1991), or derivatives or combinations of these agents. Nucleic acids may be attached to the solid support by a photocleavable bond, an electrostatic bond, a disulfide bond, a peptide bond, a diester bond or a combination of these sorts of bonds. The array may also be attached to the solid support by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

Binding may be reversible or permanent where strong associations would be critical. In addition, probes may be attached to solid supports via spacer moieties between the probes of the array and the solid support. Useful spacers include a coupling agent, as described above for binding to other or additional coupling partners, or to render the attachment to the solid support cleavable.

Cleavable attachments may be created by attaching cleavable chemical moieties between the probes and the solid support such as an oligopeptide, oligonucleotide, oligopolyamide, oligoacrylamide, oligoethylene glycerol, alkyl chains of between about 6 to 20 carbon atoms, and combinations thereof. These moieties may be cleaved with added chemical agents, electromagnetic radiation or enzymes. Examples of attachments cleavable by enzymes include peptide bonds which can be cleaved by proteases and phosphodiester bonds which can be cleaved by nucleases. Chemical agents such as β-mercaptoethanol, dithiothreitol (DTT) and other reducing agents cleave disulfide bonds. Other agents which may be useful include oxidizing agents, hydrating agents and other selectively active compounds. Electromagnetic radiation such as ultraviolet, infrared and visible light cleave photocleavable bonds. Attachments may also be reversible such as, for example, using heat or enzymatic treatment, or reversible chemical or magnetic attachments. Release and reattachment can be performed using, for example, magnetic or electrical fields.

Hybridized probes can provide direct or indirect information about the hybridized sequence. Direct information may be obtained from the binding pattern of the array wherein probe sequences are known or can be determined. Indirect information requires additional analysis of a plurality of nucleic acids of the target array. For example, a specific nucleic acid sequence will have a unique or relatively unique molecular weight depending on its size and composition. That molecular weight can be determined, for example, by chromatography (e.g. HPLC), nuclear magnetic resonance (NMR), high-definition gel electrophoresis, capillary electrophoresis (e.g. HPCE), spectroscopy or mass spectrometry. Preferably, molecular weights are determined by measuring the mass/charge ratio with mass spectrometry technology.

Mass spectrometry of biopolymers such as nucleic acids can be performed using a variety of techniques (e.g. U.S. Pat. Nos. 4,442,354; 4,931,639; 5002,868; 5,130,538; 5,135,870; 5,174,962). Difficulties associated with volatization of high molecular weight molecules such as DNA and RNA have been overcome, at least in part, with advances in techniques, procedures and electronic design. Further, only small quantities of sample are needed for analysis, the typical sample being a mixture of 10 or so fragments. Quantities which range from between about 0.1 femtomole to about 1.0 nanomole, preferably between about 1.0 femtomole to about 1000 femtomoles and more preferably between about 10 femtomoles to about 100 femtomoles are typically sufficient for analysis. These amounts can be easily placed onto the individual positions of a suitable surface or attached to a support.

Another of the important features of this invention is that it is unnecessary to volatize large lengths of nucleic acids to determine sequence information. Using the methods of the invention, segments of the nucleic acid target, discretely isolated into separate complexes on the target array, can be sequenced and those sequence segments collated making it unnecessary to have to volatize the entire strand at once. Techniques which can be used to volatize a nucleic acid fragment include fast atom bombardment, plasma desorption, matrix-assisted laser desorption/ionization, electrospray, photochemical release, electrical release, droplet release, resonance ionization and combinations of these techniques.

In electrohydrodynamic ionization, thermospray, aerospray and electrospray, the nucleic acid is dissolved in a solvent and injected with the help of heat, air or electricity, directly into the ionization chamber. If the method of ionization involves a light beam, particle beam or electric discharge, the sample may be attached to a surface and introduced into the ionization chamber. In such situations, a plurality of samples may be attached to a single surface or multiple surfaces and introduced simultaneously into the ionization chamber and still analyzed individually. The appropriate sector of the surface which contains the desired nucleic acid can be moved to proximate the path an ionizing beam. After the beam is pulsed on and the surface bound molecules are ionized, a different sector of the surface is moved into the path of the beam and a second sample, with the same or different molecule, is analyzed without reloading the machine. Multiple samples may also be introduced at electrically isolated regions of a surface. Different sectors of the chip are connected to an electrical source and ionized individually. The surface to which the sample is attached may be shaped for maximum efficiency of the ionization method used. For field ionization and field desorption, a pin or sharp edge is an efficient solid support and for particle bombardment and laser ionization, a flat surface.

The goal of ionization for mass spectroscopy is to produce a whole molecule with a charge. Preferably, a matrix-assisted laser desorption/ionization (MALDI) or electrospray (ES) mass spectroscopy is used to determine molecular weight and, thus, sequence information from the target array. It will be recognized by those of ordinary skill that a variety of methods may be used which are appropriate for large molecules such as nucleic acids. Typically, a nucleic acid is dissolved in a solvent and injected into the ionization chamber using electrohydrodynamic ionization, thermospray, aerospray or electrospray. Nucleic acids may also be attached to a surface and ionized with a beam of particles or light. Particles which have successfully used include plasma (plasma desorption), ions (fast ion bombardment) or atoms (fast atom bombardment). Ions have also been produced with the rapid application of laser energy (laser desorption) and electrical energy (field desorption).

In mass spectrometer analysis, the sample is ionized briefly by a pulse of laser beams or by an electric field induced spray. The ions are accelerated in an electric field and sent at a high velocity into the analyzer portion of the spectrometer. The speed of the accelerated ion is directly proportional to the charge (z) and inversely proportional to the mass (m) of the ion. The mass of the molecule may be deduced from the flight characteristics of its ion. For small ions, the typical detector has a magnetic field which functions to constrain the ions stream into a circular path. The radii of the paths of equally charged particles in a uniform magnetic field is directly proportional to mass. That is, a heavier particle with the same charge as a lighter particle will have a larger flight radius in a magnetic field. It is generally considered to be impractical to measure the flight characteristics of large ions such as nucleic acids in a magnetic field because the relatively high mass to charge (m/z) ratio requires a magnet of unusual size or strength. To overcome this limitation the electrospray method, for example, can consistently place multiple ions on a molecule. Multiple charges on a nucleic acid will decrease the mass to charge ratio allowing a conventional quadrupole analyzer to detect species of up to 100,000 daltons.

Nucleic acid ions generated by the matrix assisted laser desorption/ionization only have a unit charge and because of their large mass, generally require analysis by a time of flight analyzer. Time of flight analyzers are basically long tubes with a detector at one end. In the operation of a TOF analyzer, a sample is ionized briefly and accelerated down the tube. After detection, the time needed for travel down the detector tube is calculated. The mass of the ion may be calculated from the time of flight. TOF analyzers do not require a magnetic field and can detect unit charged ions with a mass of up to 100,000 daltons. For improved resolution, the time of flight mass spectrometer may include a reflectron, a region at the end of the flight tube which negatively accelerates ions. Moving particles entering the reflectron region, which contains a field of opposite polarity to the accelerating field, are retarded to zero speed and then reverse accelerated out with the same speed but in the opposite direction. In the use of an analyzer with a reflectron, the detector is placed on the same side of the flight tube as the ion source to detect the returned ions and the effective length of the flight tube and the resolution power is effectively doubled. The calculation of mass to charge ratio from the time of flight data takes into account of the time spent in the reflectron.

Ions with the same charge to mass ratio will typically leave the ion accelerators with a range of energies because the ionization regions of a mass spectrometer is not a point source. Ions generated further away from the flight tube, spend a longer time in the accelerator field and enter the flight tube at a higher speed. Thus ions of a single species of molecule will arrive at the detector at different times. In time of flight analysis, a longer time in the flight tube in theory provide more sensitivity, but due to the different speeds of the ions, the noise (background) will also be increased. A reflectron, besides effectively doubling the effective length of the flight tube, can reduce the error and increase sensitivity by reducing the spread of detector impingement time of a single species of ions. An ion with a higher velocity will enter the reflectron at a higher velocity and stay in the reflectron region longer than a lower velocity ion. If the reflectron electrode voltages are arranged appropriately, the peak width contribution from the initial velocity distribution can be largely corrected for at the plane of the detector. The correction provided by the reflectron leads to increased mass resolution for all stable ions, those which do not dissociate in flight, in the spectrum.

While a linear field reflectron functions adequately to reduce noise and enhance sensitivity, reflectrons with more complex field strengths offer superior correctional abilities and a number of complex reflectrons can be used. The double stage reflectron has a first region with a weaker electric field and a second region with a stronger electric field. The quadratic and the curve field reflectron have a electric field which increases as a function of the distance. These functions, as their name implies, may be a quadratic or a complex exponential function. The dual stage, quadratic, and curve field reflectrons, while more elaborate are also more accurate than the linear reflectron.

The detection of ions in a mass spectrometer is typically performed using electron detectors. To be detected, the high mass ions produced by the mass spectrometer is converted into either electrons or low mass ions at a conversion electrode. These electrons or low mass ions are then used to start the electron multiplication cascade in an electron multiplier and further amplified with a fast linear amplifier. The signals from multiple analysis of a single sample are combined to improve the signal to noise ratio and the peak shapes, which also increase the accuracy of the mass determination.

This invention is also directed to the detection of multiple primary ions directly through the use of ion cyclotron resonance and Fourier analysis. This is useful for the analysis of a complete sequencing ladder immobilized on a surface. In this method, a plurality of samples are ionized at once and the ions are captured in a cell with a high magnetic field. An RF field excites the population of ions into cyclotron orbits. Because the frequencies of the orbits are a function of mass, an output signal representing the spectrum of the ion masses is obtained. This output is analyzed by a computer using Fourier analysis which reduces the combined signal to its component frequencies and thus provides a measurement of the ion masses present in the ion sample. Ion cyclotron resonance and Fourier analysis can determine the masses of all nucleic acids in a sample. The application of this method is especially useful on a sequencing ladder.

The data from mass spectrometry, either performed singly or in parallel (multiplexed), can determine the molecular mass of a nucleic acid sample. The molecular mass, combined with the known sequence of the sample, can be analyzed to determine the length of the sample. Because different bases have different molecular weight, the output of a high resolution mass spectrometer, combined with the known sequence and reaction history of the sample, will determine the sequence and length of the nucleic acid analyzed. In the mass spectroscopy of a sequencing ladder, generally the base sequence of the primers are known. From a known sequence of a certain length, the added base of a sequence one base longer can be deduced by a comparison of the mass of the two molecules. This process is continued until the complete sequence of a sequencing ladder is determined.

Another embodiment of the invention is directed to a method for detecting a target nucleic acid. As before, a set of nucleic acids complementary or homologous to a sequence of the target is hybridized to an array of nucleic acid probes. The molecular weights of the hybridized nucleic acids determined by, for example, mass spectrometry and the nucleic acid target detected by the presence of its sequence in the sample. As the object is not to obtain extensive sequence information, probe arrays may be fairly small with the critical sequences, the sequences to be detected, repeated in as many variations as possible. Variations may have greater than 95% homology to the sequence of interest, greater than 80%, greater than 70% or greater than about 60%. Variations may also have additional sequences not required or present in the target sequence to increase or decrease the degree of hybridization. Sensitivity of the array to the target sequence is increased while reducing and hopefully eliminating the number of false positives.

Target nucleic acids to be detected may be obtained from a biological sample, an archival sample, an environmental sample or another source expected to contain the target sequence. For example, samples may be obtained from biopsies of a patient and the presence of the target sequence is indicative of the disease or disorder such as, for example, a neoplasm or an infection. Samples may also be obtained from environmental sources such as bodies of water, soil or waste sites to detect the presence and possibly identify organisms and microorganism which may be present in the sample. The presence of particular microorganisms in the sample may be indicative of a dangerous pathogen or that the normal flora is present.

Another embodiment of the invention is directed to the arrays of nucleic acid probes useful in the above-described methods and procedures. These probes comprise a first strand and a second strand wherein the first strand is hybridized to the second strand forming a double-stranded portion, a single-stranded portion and a variable sequence within the single-stranded portion. The array may be attached to a solid support such as a material that facilitates volatization of nucleic acids for mass spectrometry. Typically, arrays comprise large numbers of probes such as less than or equal to about $4^R$ different probes and R is the length in nucleotides of the variable sequence. When utilizing arrays for large scale sequencing, larger arrays can be used whereas, arrays which are used for detection of specific sequences may be fairly small as many of the potential sequence combinations will not be necessary.

Arrays may also comprise nucleic acid probes which are entirely single-stranded and nucleic acids which are single-stranded, but possess hairpin loops which create double-stranded regions. Such structures can function in a manner similar if not identical to the partially single-stranded probes, which comprise two strands of nucleic acid, and have the additional advantage of thermodynamic energy available in the secondary structure.

Arrays may be in solution or fixed on a solid support through streptavidin-biotin interactions or other suitable coupling agents. Arrays may also be reversibly fixed to the solid support using, for example, chemical moieties which can be cleaved with electromagnetic radiation, chemical agents and the like. The solid support may comprise materials such as matrix chemicals which assist in the volatization process for mass spectrometric analysis. Such chemicals include nicotinic acid, 3'-hydroxypicolnic acid, 2,5-dihydroxybenzoic acid, sinapinic acid, succinic acid, glycerol, urea and Tris-HCl, pH about 7.3.

Another embodiment of the invention is directed to sequencing double-stranded nucleic acids using strand-displacement polymerization. With this method it is unnecessary to denature the double-strands to obtain sequence information. Strand-displacement polymerization creates a new strand while simultaneously displacing the existing strand. Techniques for incorporating label into the growing strand are well-know and the newly polymerized strand is easily detected by, for example, mass spectrometry.

Target nucleic acid or nucleic acids containing sequences that correspond to the sequence of the target are digested, for example, with restriction enzymes, in one or more steps to create a set of fragments which are partially single-stranded and partially double-stranded. Another set of nucleic acids, the probes, are also partially single-stranded and partially double-stranded. These probes preferably contain a variable or constant regions within the single-stranded portion of the terminus of each fragment (5'- or 3'-overhangs). Probes or fragments are treated with a phosphatase to remove phosphate groups from the 5'-termini of the nucleic acids. Phosphatase treatment prevents nucleic acid ligation by ligase which requires a terminal 5'-phosphate to covalently link to a 3'-hydroxyl. Single-stranded regions of the fragments are hybridized to single-stranded regions of the probes forming an array of hybridized target/probe complexes. Adjacent or abutting nucleic acid strands of the complex are ligated, covalently joining a strand of the fragment to a strand of the probe. Phosphatase treatment prevents both self-ligation of phosphatase-treated nucleic acids and ligation between the 5'-termeni of phosphased nucleic acids and the 3'-termeni of untreated nucleic acids. These complexes are treated with a nucleic acid polymerase that recognizes and bind to the nick in the unligated strand to initiate polymerization. The polymerase synthesizes a new strand using the ligated stand as a template, while displacing the complementary strand. The reaction may be supplemented with labeled or mass modified nucleotides (e.g. mass modifications at positions C2, N3, N7 or C8 of purine, or at N7 or N9 of deazapurine) or other detectable markers that will allow for the detection of new synthesis. Either the probes or the fragments may be fixed to a solid support such as a plastic or glass surface, membrane or structure (magnetic bead) which eliminates the need for repetitive extractions or other purification of nucleic acids between steps.

Preferably, double-stranded nucleic acids containing target sequences are obtained by polymerase chain reaction or enzymatic digestion (e.g. restriction enzymes) of the target sequence. Target sequences may be DNA, RNA, RNA/DNA hybrids, cDNA, PNA or modifications or combinations thereof and are preferably from about 10 to about 1,000 nucleotides in length, more preferably, from about 20 to about 500 nucleotides in length, and even more preferably, from about 35 to about 250 nucleotides in length. 5'-termini of the nucleic acid fragments or probes may be dephosphorylated with a phosphatase, such as alkaline or calf intestinal phosphatase, which eliminates the action of a nucleic acid ligase. Upon hybridization of fragment to probe, only one of the two internal 5'-3' junctions contains a 5'-phosphate and is capable of ligation. The second junction appears as a nick in a strand of the complex. Nucleic acid polymerases, such as Klenow, recognize the nick and synthesize a new strand while displacing the complementary, ligated strand. Chain elongation can proceed in the presence of, for example, nucleotide triphosphates and chain terminating nucleotides. Nucleic acid synthesis terminates when a dideoxynucleotide is incorporated into the elongating strand. The resulting fragments represent a nested set of the sequence of the target. Precursor nucleotides may be labeled with, for example, mass modifications. The mass modified fragments can be easily analyzed by mass spectrometry to determine the sequence of the target. Complexes may further comprise single-stranded binding protein (SSB; *E. coli*) which increases stability of the complex and facilitate polymerase action. Bands otherwise obscured are more easily detected. SSB can be used to sequence fragments of greater than 100 nucleotides, preferably greater than 150 nucleotides and more preferably greater than 200 nucleotides.

This method is generally useful for manual or automated nucleic acid sequencing, and especially useful for identifying and sequencing a single or group of nucleic acid species in a mixed background containing a plurality of species of different sequences. In this method, selection is performed upon hybridization and ligation of fragments to probes. Probes may be designed to contain a common or variable sequence within the single-stranded region that is complementary to a sequence of the fragment to be identified and, if desired, sequenced. Stringency of fragment/probe hybridization can be adjusted by methods well-known to those of ordinary skill to match desired conditions of selection. For example, the single-stranded region of the probe can be designed to contain a specific sequence only found on the single-stranded region of the nucleic acid fragment of interest. Alternatively, multiple probes containing multiple variable regions may be used to select for those fragment sequences which may be longer than the length of the single-stranded region of any one probe. Hybridization and ligation selects the specific fragment from a complex mixture of different fragments and only that specific fragment is subsequently sequenced.

Probes are typically from about 15 to about 200 nucleotides in length, but can be larger or small depending on the particular application. Single-stranded regions of the probes may be about 3, 4, 5, 6, 7, 8, 9, 10, 12, 15, 20, 22, 25 or 30 nucleotides in length or larger. For probes containing a variable region within the single-stranded region, the length of this variable region may be the same or smaller than the length of the entire single-stranded portion. Variable regions may be distinct between probes or common within sets of probes. The double-stranded region of the probe is typically larger than the single-stranded region and may be about 4, 5, 6, 7, 8, 9, 10, 12, 14, 16, 18, 20, 22, 24, 26, 28, 30, 35 40 or 50 nucleotides in length or larger. Probes may also be modified to facilitate attachment to a solid support or other surfaces, or modified to be individual detectable for identification or other purposes. Sets of nucleic acids, either fragments or probes, preferably contain greater than $10^2$, $10^3$, $10^4$, $10^5$, $10^6$, $10^7$, $10^8$, $10^9$ or $10^{10}$ different members.

Another embodiment of the invention is directed to kits for detecting a sequence of a target nucleic acid. An array of nucleic acid probes is fixed to a solid support which may be coated with a matrix chemical that facilitates volatization of nucleic acids for mass spectrometry. Kits can be used to detect diseases and disorders in biological samples by detecting specific nucleic acid sequences which are indicative of the disorder. Probes may be labeled with detectable labels which only become detectable upon hybridization with a correctly matched target sequence. Detectable labels include radioisotopes, metals, luminescent or bioluminescent chemicals, fluorescent chemicals, enzymes and combinations thereof.

Another embodiment of the invention is directed to nucleic acid sequencing systems which comprise a mass spectrometer, a computer loaded with appropriate software for analysis of nucleic acids and an array of probes which can be used to capture a target nucleic acid sequence. Systems may be manual or automated as desired.

The following experiments are offered to illustrate embodiments of the invention, and should not be viewed as limiting the scope of the invention.

EXAMPLES

Example 1
Preparation of Target Nucleic Acid.

Target nucleic acid is prepared by restriction endonuclease cleavage of cosmid DNA. The properties of type II and other restriction nucleases that cleave outside of their recognition sequences were exploited. A restriction digestion of a 10 to 50 kb DNA sample with such an enzyme produced a mixture of DNA fragments most of which have unique ends. Recognition and cleavage sites of useful enzymes are shown in Table 1.

TABLE 1

| Restriction Enzymes and Recognition Sites for PSBH | |
|---|---|
| Mwo I | ↓<br>GCNNNNN-NNGC<br>CGNN-NNNNNCG<br>↑ |
| Esi YI | ↓<br>CCNNNNN-NNGG<br>GGNN-NNNNNCC<br>↑ |
| Apa BI | ↓<br>GCANNNNN-TGC<br>CGT-NNNNNACG<br>↑ |
| Mnl I | ↓<br>CCTCN$_7$<br>GGAGN$_6$<br>↑ |
| Tsp RI | ↓<br>NNCAGTGNN<br>NNGTCACNN<br>↑ |
| Cje I | ↓<br>CCANNNNNN-GTNNNN<br>GGTNNNNNN-CANNNN<br>↑ |
| Cje PI | ↓<br>CCANNNNN-NNTCNN<br>GGTNNNNN-NNAGNN<br>↑ |

One restriction enzyme, ApaB 15, with a 6 base pair recognition site may also be used. DNA sequencing is best served by enzymes that produce average fragment lengths comparable to the lengths of DNA sequencing ladders analyzable by mass spectrometry. At present these lengths are about 100 bases or less.

BsiY I and Mwo I restriction endonucleases are used together to digest DNA in preparation of PSBH. Target DNA from is cleaved to completion and complexed with PSBH probes either before or after melting. The fraction of fragments with unique ends or degenerate ends depends on the complexity of the target sequence. For example, a 10 kilobase clone would yield on average 16 fragments or a total of 32 ends since each double-stranded DNA target produces two ligatable 3' ends. With 1024 possible ends, Poisson statistics (Table 2) predict that there would be 3% degeneracies. In contrast, a 40 kilobase cosmid insert would yield 64 fragments or 128 ends, of which, 12% of these would be degenerate and a 50 kilobase sample would yield 80 fragments or 160 ends. Some of these would surely be degenerate. Up to at least 100 kilobase, the larger the target the more sequence are available from each multiplex DNA sample preparation. With a 100 kilobase target, 27% of the targets would be degenerate.

TABLE 2

Poisson Distribution of Restriction Enzyme Sites

| Target size | Mwo I | | TspR I | |
|---|---|---|---|---|
| (kb) | Sequencing | Assembly | Sequencing | Assembly |
| 10 | 0.97 | 0.60 | 0.94 | 0.94 |
| 40 | 0.88 | 0.14 | 0.80 | 0.80 |
| 100 | 0.73 | 0.01 | 0.57 | 0.57 |

Figure 5:
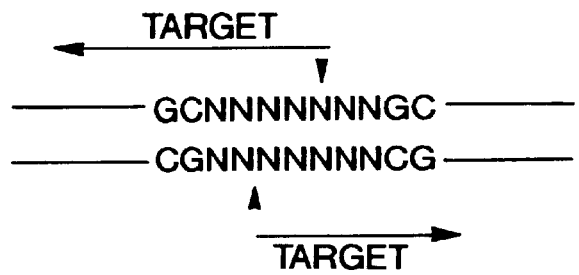
FIG. 5 Cleavage site of Mwo 1 indicating bidirectional sequencing.

With BsiY I and Mwo I, any restriction site that yields a unique 5 base end may be captured twice and the resulting sequence data obtained will read away from the site in both directions (FIG. 5). With the knowledge of three bases of overlapping sequence at the site, this sorts all sequences into 64 different categories. With 10 kilobase targets, 60% will contain fragments and, thus sequence assembly is automatic.

Two array capture methods can be used with Mwo I and BsiY I. In the first method, conventional five base capture is used. Because the two target bases adjacent to the capture site are known, they from the restriction enzyme recognition sequence, an alternative capture strategy would build the complement of these two bases into the capture sequence. Seven base capture is thermodynamically more stable, but less discriminating against mismatches.

Figure 6:
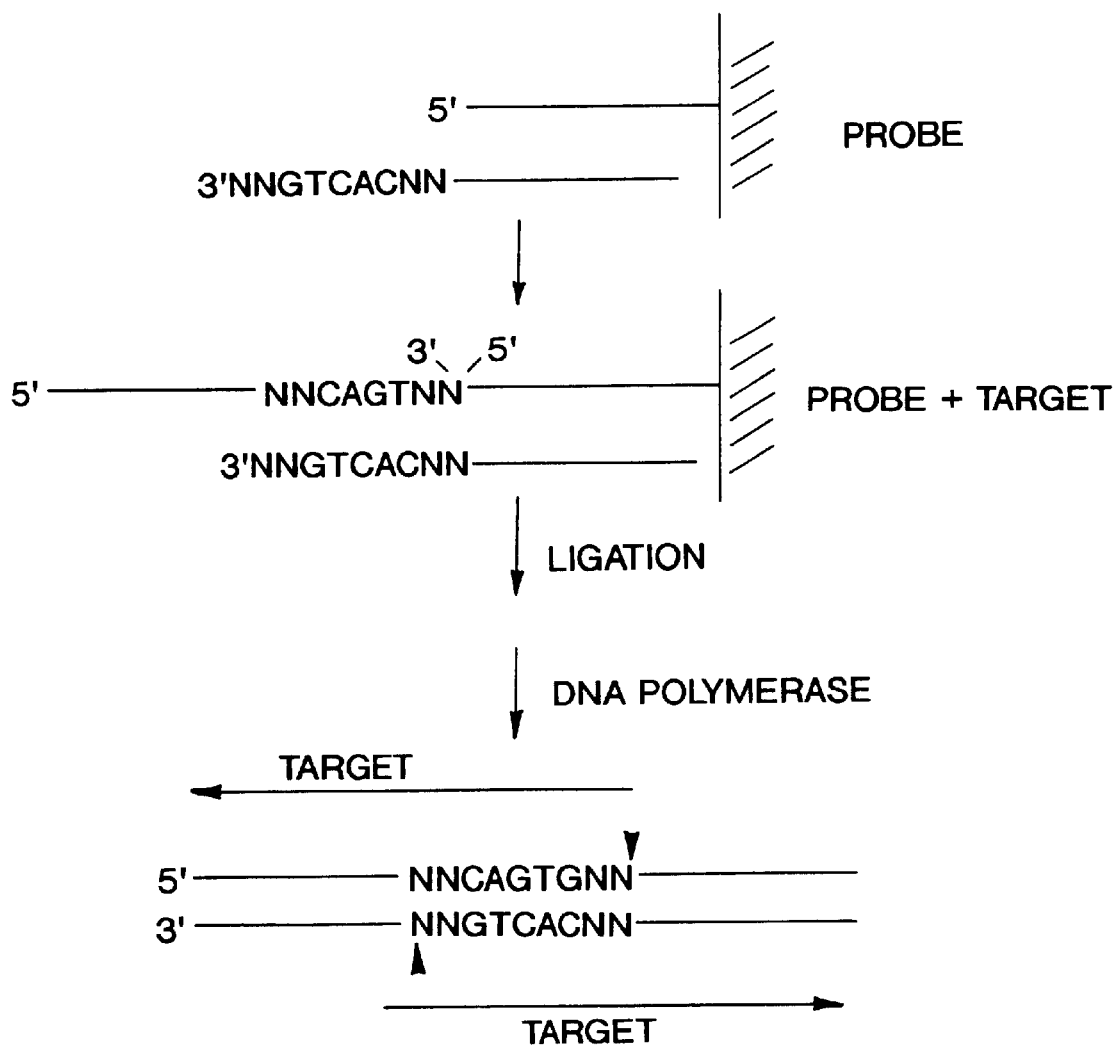
FIG. 6 Schematic of sequencing strategy after target DNA digestion by Tsp R1.

TspR I is another commercially available restriction enzyme with properties that are very attractive for use in PSBH-mediated Sanger sequencing. The method for using TspR I is shown in FIG. 6. TspR I has a five base recognition site and cuts two bases outside this site on each strand to yield nine base 3' single-stranded overhangs. These can be captured with partially duplex probes with complementary nine base overhangs. Because only four bases are not specified by enzyme recognition, TspR I digest results in only 256 types of cleavage sites. With human DNA the average fragment length that should result is 1370 bases. This enzyme is ideal to generate long Sequence ladders and are useful to input to long thin gel sequencing where reads up to a kilobase are common. A typical human cosmid yields about 30 TspR I fragments or 60 ends. Given the length distribution expected, many of these could not be sequenced fully from one end. With 256 possible overhangs, Poisson statistics (Table 2) indicate that 80% adjacent fragments can be assembled with no additional labor. Thus, very long blocks of continuous DNA sequence are produced.

Three additional restriction enzymes are also useful. These are Mnl I, Cje I and CjeP I (Table 1). The first has a four base site with one A+T should give smaller human DNA fragments on average than Mwo I or BsiYI. The latter two have unusual interrupted five base recognition sites and might supplement TspR I.

Target DNA may also be prepared by tagged PCR. It is possible to add a preselected five base 3' terminal sequence to a target DNA using a PCR primer five bases longer than the known target sequence priming site. Samples made in this way can be captured and sequenced using the PSBH approach based on the five base tag. A biotin was used to allow purification of the complementary strand prior to use as an immobilized sequencing template. A biotin may also be placed on the tag. After capture of the duplex PCR product by streptavidin-coated magnetic microbeads, the desired strand (needed to serve as a sequencing template) could be denatured from the duplex and used to contact the entire probe array. For multiplex sample preparation, a series of different five base tagged primers would be employed, ideally in a single multiplex PCR reaction This approach also requires knowing enough target sequence for unique PCR amplification and is more useful for shotgun sequencing or comparative sequencing than for de novo sequencing.

Example 2

Basic Aspects of Positional Sequencing by Hybridization.

An examination of the potential advantages of stacking hybridization has been carried out by both calculations and pilot experiments. Some calculated $T_m$'s for perfect and mismatched duplexes are shown in FIG. 7. These are based on average base compositions. The calculations revealed that the binding of a second oligomer next to a pre-formed duplex provides an extra stability equal to about two base pairs and that mis-pairing seems to have a larger consequence on stacking hybridization than it does on ordinary hybridization. Other types of mis-pairing are less destabilizing, but these can be eliminated by requiring a ligation step. In standard SBH, a terminal mismatch is the least destabilizing event, and leads to the greatest source of ambiguity or background. For an octanucleotide complex, an average terminal mismatch leads to a 6° C. lowering in $T_m$. For stacking hybridization, a terminal mismatch on the side away from the pre-existing duplex, is the least destabilizing event. For a pentamer, this leads to a drop in $T_m$ of 10° C. These considerations indicate that the discrimination power of stacking hybridization in favor of perfect duplexes are greater than ordinary SBH.

Example 3

Preparation of Model Arrays.

In a single synthesis, all 1024 possible single-stranded probes with a constant 18 base stalk followed by a variable 5 base extension can be created. The 18 base extension is designed to contain two restriction enzyme cutting sites. Hga I generates a 5 base, 5' overhang consisting of the variable bases $N_5$. Not I generates a 4 base, 5' overhang at the constant end of the oligonucleotide. The synthetic 23-mer mixture hybridized with a complementary 18-mer forms a duplex which can be enzymatically extended to form all 1024, 23-mer duplexes. These are cloned by, for example, blunt end ligation, into a plasmid which lacks Not I sites. Colonies containing the cloned 23-base insert are selected and each clone contains one unique sequence. DNA minipreps can be cut at the constant end of the stalk, filled in with biotinylated pyrimidines and cut at the variable end of the stalk to generate the 5 base 5' overhang. The resulting nucleic acid is fractionated by Qiagen columns (nucleic acid purification columns) to discard the high molecular weight material. The nucleic acid probe will then be attached to a streptavidin-coated surface. This procedure could easily be automated in a Beckman Biomec or equivalent chemical robot to produce many identical arrays of probes.

The initial array contains about a thousand probes. The particular sequence at any location in the array will not be known. However, the array can be used for statistical evaluation of the signal to noise ratio and the sequence discrimination for different target molecules under different hybridization conditions. Hybridization with known nucleic acid sequences allows for the identification of particular elements of the array. A sufficient set of hybridizations would train the array for any subsequent sequencing task. Arrays are partially characterized until they have the desired properties. For example, the length of the oligonucleotide duplex, the mode of its attachment to a surface and the hybridization conditions used can all be varied using the initial set of cloned DNA probes. Once the sort of array that works best is determined, a complete and fully characterized array can be constructed by ordinary chemical synthesis.

Example 4

Preparation of Specific Probe Arrays.

With positional SBH, one potential trick to compensate for some variations in stability among species due to GC content variation is to provide GC rich stacking duplex adjacent AT rich overhangs and AT rich stacking duplex adjacent GC rich overhangs. Moderately dense arrays can be made using a typical x-y robot to spot the biotinylated compounds individually onto a streptavidin-coated surface. Using such robots, it is possible to make arrays of $2 \times 10^4$ samples in 100 to 400 $cm^2$ of nominal surface. Commercially available streptavidin-coated beads can be adhered, permanently to plastics like polystyrene, by exposing the plastic first to a brief treatment with an organic solvent like triethylamine. The resulting plastic surfaces have enormously high biotin binding capacity because of the very high surface area that results.

In certain experiments, the need for attaching oligonucleotides to surfaces may be circumvented altogether, and oligonucleotides attached to streptavidin-coated magnetic microbeads used as already done in pilot experiments. The beads can be manipulated in microtiter plates. A magnetic separator suitable for such plates can be used including the newly available compressed plates. For example, the 18 by 24 well plates (Genetix, Ltd.; USA Scientific Plastics) would allow containment of the entire array in 3 plates. This format is well handled by existing chemical robots. It is preferable to use the more compressed 36 by 48 well format so the entire array would fit on a single plate. The advantages of this approach for all the experiments are that any potential complexities from surface effects can be avoided and already-existing liquid handling, thermal control and imaging methods can be used for all the experiments.

Figure 8:
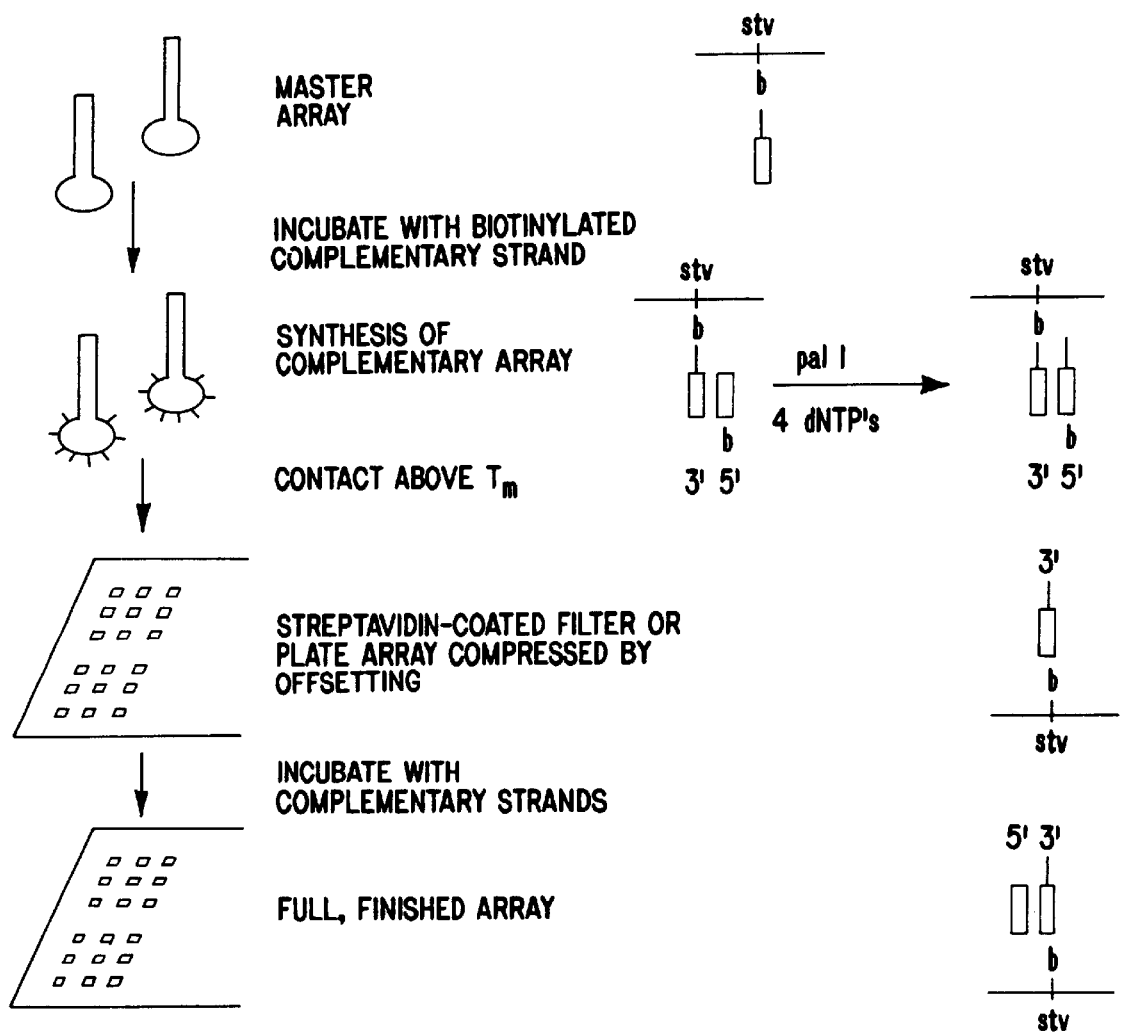
FIG. 8 Replication of a master array.

Lastly, a rapid and highly efficient method to print arrays has been developed. Master arrays are made which direct the preparation of replicas or appropriate complementary arrays. A master array is made manually (or by a very accurate robot) by sampling a set of custom DNA sequences in the desired pattern and then transferring these sequences to the replica. The master array is just a set of all 1024–4096 compounds printed by multiple headed pipettes and compressed by offsetting. A potentially more elegant approach is shown in FIG. 8. A master array is made and used to transfer components of the replicas in a sequence-specific way. The sequences to be transferred are designed to contain the desired 5 or 6 base 5' variable overhang adjacent to a unique 15 base DNA sequence.

The master array consists of a set of streptavidin bead-impregnated plastic coated metal pins. Immobilized biotinylated DNA strands that consist of the variable 5 or 6 base segment plus the constant 15 base segment are at each tip. Any unoccupied sites on this surface are filled with excess free biotin. To produce a replica chip, the master array is incubated with the complement of the 15 base constant sequence, 5'-labeled with biotin. Next, DNA polymerase is used to synthesize the complement of the 5 or 6 base variable sequence. Then the wet pin array is touched to the streptavidin-coated surface of the replica and held at a temperature above the $T_m$ of the complexes on the master array. If there is insufficient liquid carryover from the pin array for efficient sample transfer, the replica array could first be coated with spaced droplets of solvent, either held in concave cavities or delivered by a multi-head pipettor. After the transfer, the replica chip is incubated with the complement of 15 base constant sequence to reform the double-stranded portions of the array. The basic advantage of this scheme is that the master array and transfer compounds are made only once and the manufacture of replica arrays can proceed almost endlessly.

Example 5

Attachment of Nucleic Acids Probes to Solid Supports.

Nucleic acids may be attached to silicon wafers or to beads. A silicone solid support was derivatized to provide iodoacetyl functionalities on its surface. Derivatized solid support were bound to disulfide containing oligodeoxynucleotides. Alternatively, the solid support may be coated with streptavidin or avidin and bound to biotinylated DNA.

Figure 9:
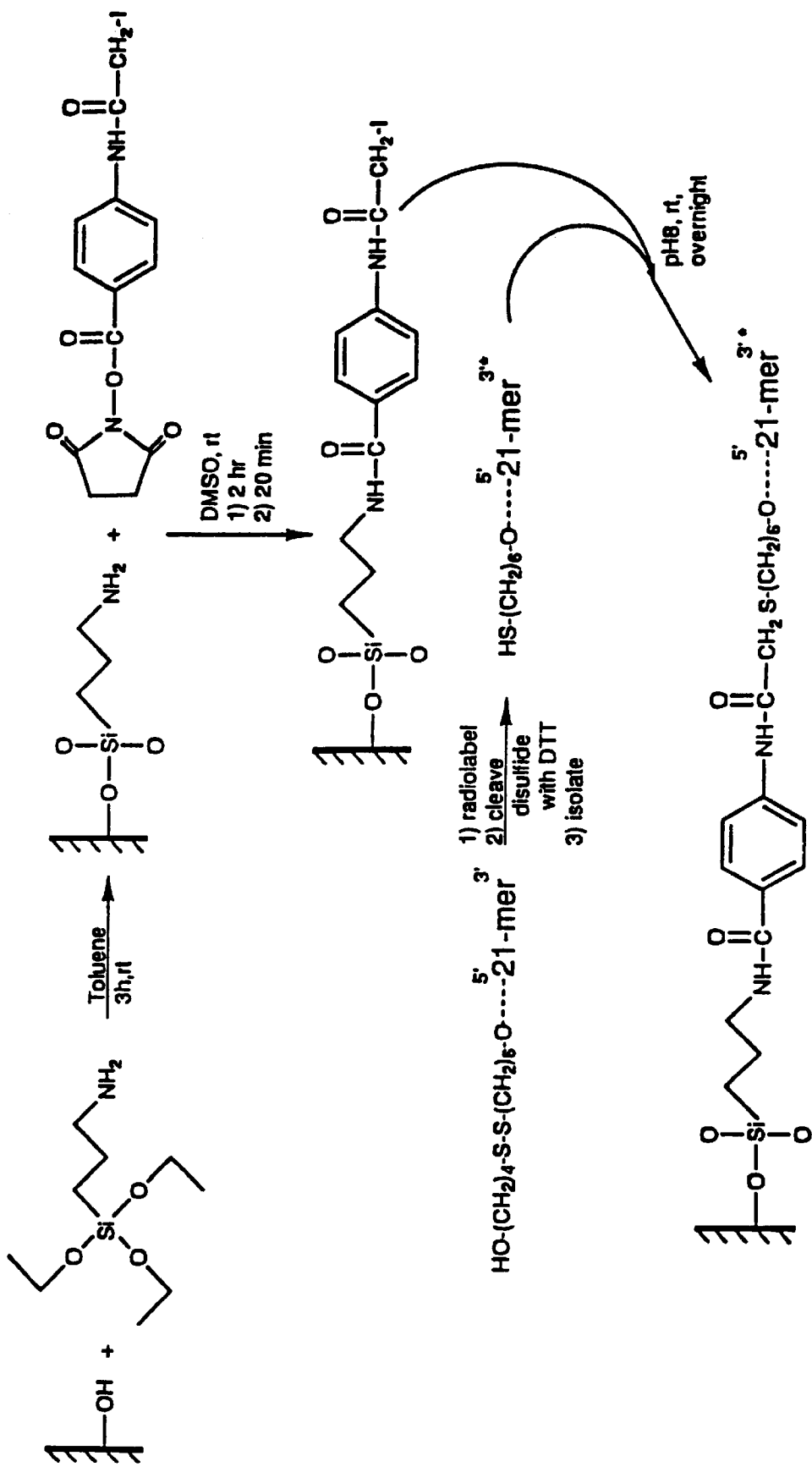
FIG. 9 Reaction scheme for the covalent attachment of DNA to a surface.

Covalent attachment of oligonucleotide to derivatized chips: Silicon wafers are chips with an approximate weight of 50 mg. To maintain uniform reaction condition, it was necessary to determine the exact weight of each chip and select chips of similar weights for each experiment. The reaction scheme for this procedure is shown in FIG. 9.

To derivatize the chip to contain the iodoacetyl functionality an anhydrous solution of 25% (by volume) 3-aminopropyltrieshoxysilane in toluene was prepared under argon and aliquotted (700 $\mu$l) into tubes. A 50 mg chip requires approximately 700 $\mu$l of silane solution. Each chip was flamed to remove any surface contaminants during its manufacture and dropped into the silane solution. The tube containing the chip was placed under an argon environment and shaken for approximately three hours. After this time, the silane solution was removed and the chips were washed three times with toluene and three times with dimethyl sulfoxide (DMSO). A 10 mM solution of N-succinimidyl (4-iodoacetyl)aminobenzoate (SIAB) (Pierce Chemical Co.; Rockford, Ill.) was prepared in anhydrous DMSO and added to the tube containing a chip. Tubes were shaken under an argon environment for 20 minutes. The SIAB solution was removed and after three washes with DMSO, the chip was ready for attachment to oligonucleotides.

Some oligonucleotides were labeled so the efficiency of attachment could monitored. Both 5' disulfide containing oligodeoxynucleotides and unmodified oligodeoxynucleotides were radiolabeled using terminal deoxynucleotidyl transferase enzyme and standard techniques. In a typical reaction, 0.5 mM of disulfide-containing oligodeoxynucleotide mix was added to a trace amount of the same species that had been radiolabeled as described above. This mixture was incubated with dithiothreitol (DTT) (6.2 $\mu$mol, 100 mM) and ethylenediaminetetraacetic acid (EDTA) pH 8.0 (3 $\mu$mol, 50 mM). EDTA served to chelate any cobalt that remained from the radiolabeling reaction that would complicate the cleavage reaction. The reaction was allowed to proceed for 5 hours at 37° C. With the cleavage reaction essentially complete, the free thiol-containing oligodeoxynucleotide was isolated using a Chromaspin-10 column.

Similarly, Tris-(2-carboxyethyl)phosphine (TCEP) (Pierce Chemical Co.; Rockford, Ill.) has been used to cleave the disulfide. Conditions utilize TCEP at a concentration of approximately 100 mM in pH 4.5 buffer. It is not necessary to isolate the product following the reaction since TCEP does not competitively react with the iodoacetyl functionality.

To each chip which had been derivatized to contain the iodoacetyl functionality was added to a 10 µM solution of the oligodeoxynucleotide at pH 8. The reaction was allowed to proceed overnight at room temperature. In this manner, two different oligodeoxynucleotides have been examined for their ability to bind to the iodoacetyl silicon wafer. The first was the free thiol containing oligodeoxynucleotide already described. In parallel with the free thiol containing oligodeoxynucleotide reaction, a negative control reaction has been performed that employs a 5' unmodified oligodeoxynucleotide. This species has similarly been 3' radiolabeled, but due to the unmodified 5' terminus, the non-covalent, non-specific interactions may be determined. Following the reaction, the radiolabeled oligodeoxynucleotides were removed and the chips were washed 3 times with water and quantitation proceeded.

To determine the efficiency of attachment, chips of the wafer were exposed to a phosphorimager screen (Molecular Dynamics). This exposure usually proceeded overnight, but occasionally for longer periods of time depending on the amount of radioactivity incorporated. For each different oligodeoxynucleotide utilized, reference spots were made on polystyrene in which the molar amount of oligodeoxynucleotide was known. These reference spots were also exposed to the phosphorimager screen. Upon scanning the screen, the quantity (in moles) of oligodeoxynucleotide bound to each chip was determined by comparing the counts to the specific activities of the references. Using the weight of each chip, it is possible to calculate the area of the chip:

(g of chip) (1130 mm$^2$/g)=×mm$^2$

By incorporating this value, the amount of oligodeoxynucleotide bound to each chip may be reported in fmol/mm$^2$. It is necessary to divide this value by two since a radioactive signal of $^{32}$P is strong enough to be read through the silicon wafer. Thus the instrument is essentially recording the radioactivity from both sides of the chip.

Following the initial quantitation each chip was washed in 5×SSC buffer (75 mM sodium citrate, 750 mM sodium chloride, pH 7) with 50% formamide at 65° C. for 5 hours. Each chip was washed three times with warm water, the 5×SSC wash was repeated, and the chips requantitated. Disulfide linked oligonucleotides were removed from the chip by incubation with 100 mM DTT at 37° C. for 5 hours.

Example 6

Attachment of Nucleic Acids to Streptavidin Coated Solid Support.

Immobilized single-stranded DNA targets for solid-phase DNA sequencing were prepared by PCR amplification. PCR was performed on a Perkin Elmer Cetus DNA Thermal Cycler using Vent$_R$ (exo$^-$) DNA polymerase (New England Biolabs; Beverly, Mass.), and dNTP solutions (Promega; Madison, Wis.). EcoR I digested plasmid NB34 (a PCR™ II plasmid with a one kb target anonymous human DNA insert) was used as the DNA template for amplification. PCR was performed with an 18-nucleotide upstream primer and a downstream 5'-end biotinylated 18-nucleotide primer. PCR amplification was carried out in a 100 µl or 400 µl volume containing 10 mM KCl, 20 mM Tris-HCl (pH 8.8 at 25° C.), 10 mM (NH$_4$)$_2$SO$_4$, 2 mM MgSO$_4$, 0.1% Triton X-100, 250 µM dNTPs, 2.5 µM biotinylated primer, 5 µM non-biotinylated primer, less than 100 ng of plasmid DNA, and 6 units of Vent (exo$^-$) DNA polymerase per 100 µl of reaction volume. Thirty temperature cycles were performed which included a heat denaturation step at 94° C. for 1 minute, followed by annealing of primers to the template DNA for 1 minute at 60° C., and DNA chain extension with Vent (exo$^-$) polymerase for 1 minute at 72° C. For amplification with the tagged primer, 45° C. was selected for primer annealing. The PCR product was purified through a Ultrafree-MC 30,000 NMWL filter unit (Millipore; Bedford, Mass.) or by electrophoresis and extraction from a low melting agarose gel. About 10 pmol of purified PCR fragment was mixed with 1 mg of prewashed magnetic beads coated with streptavidin (Dynabeads M280, Dynal, Norway) in 100 µl of 1 M NaCl and TE incubating at 37° C. or 45° C. for 30 minutes.

The magnetic beads were used directly for double stranded sequencing.

For single stranded sequencing, the immobilized biotinylated double-stranded DNA fragment was converted to single-stranded form by treating with freshly prepared 0.1 M NaOH at room temperature for 5 minutes. The magnetic beads, with immobilized single-stranded DNA, were washed with 0.1 M NaOH and TE before use.

Example 7

Hybridization Specificity.

Hybridization was performed using probes with five and six base pair overhangs, including a five base pair match, a five base pair mismatch, a six base pair match, and a six base pair mismatch. These sequences are depicted in Table 3.

TABLE 3

Hybridized Test Sequences

Test Sequences:

5 bp overlap, perfect match:

| | |
|---|---|
| 3'-TCG AGA ACC TTG GCT*-5' | (SEQ ID NO 1) |
| 3'-CTA CTA GGC TGC GTA GTC | (SEQ ID NO 2) |
| 5'-biotin-GAT GAT CCG ACG CAT CAG AGC TC-3' | (SEQ ID NO 3) |

5 bp overlap, mismatch at 3' end:

| | |
|---|---|
| 3'-TCG AGA ACC TTG GCT*-5' | (SEQ ID NO 1) |
| 3'-CTA CTA GGC TGC GTA GTC | (SEQ ID NO 2) |
| 5'-biotin-GAT GAT CCG ACG CAT CAG AGC TT-3' | (SEQ ID NO 4) |

6 bp overlap, perfect match:

| | |
|---|---|
| 3'-TCG AGA ACC TTG GCT*-5' | (SEQ ID NO 1) |
| 3'-CTA CTA GGC TGC GTA GTC | (SEQ ID NO 2) |

TABLE 3-continued

Hybridized Test Sequences

Test Sequences:

| | |
|---|---|
| 5'-biotin-GAT GAT CCG ACG CAT CAG AGC TCT-3' | (SEQ ID NO 5) |
| 6 bp overlap, mismatch four bases from 3' end: | |
| 3'-TCG AGA ACC TTG GCT*-5' | (SEQ ID NO 1) |
| 3'-CTA CTA GGC TGC GTA GTC | (SEQ ID NO 2) |
| 5'-biotin-GAT GAT CCG ACG CAT CAG AG<u>T</u> TCT-3' | (SEQ ID NO 6) |

Figure 10:
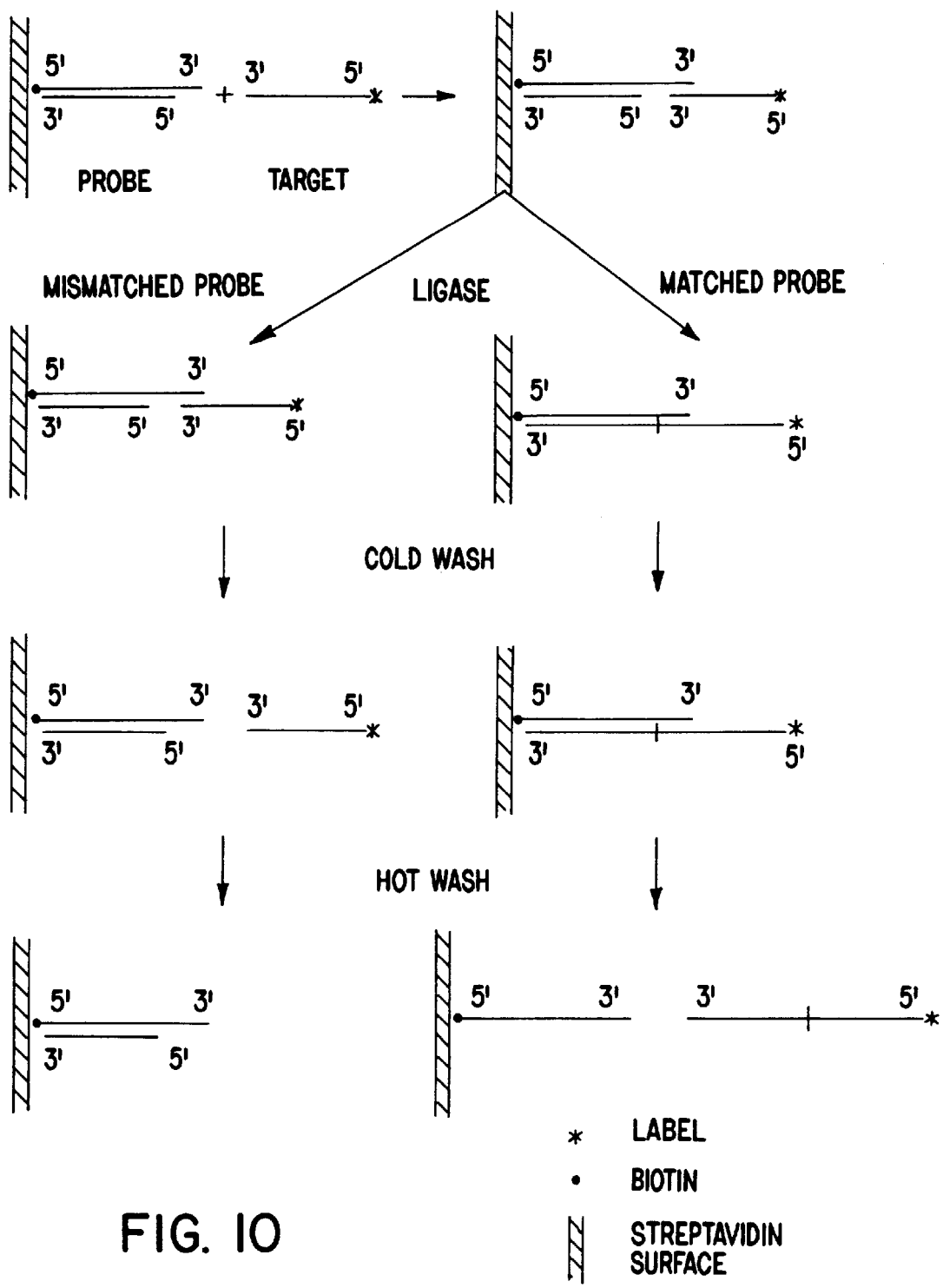
FIG. 10 Target nucleic acid capture and ligation.
Figure 11:
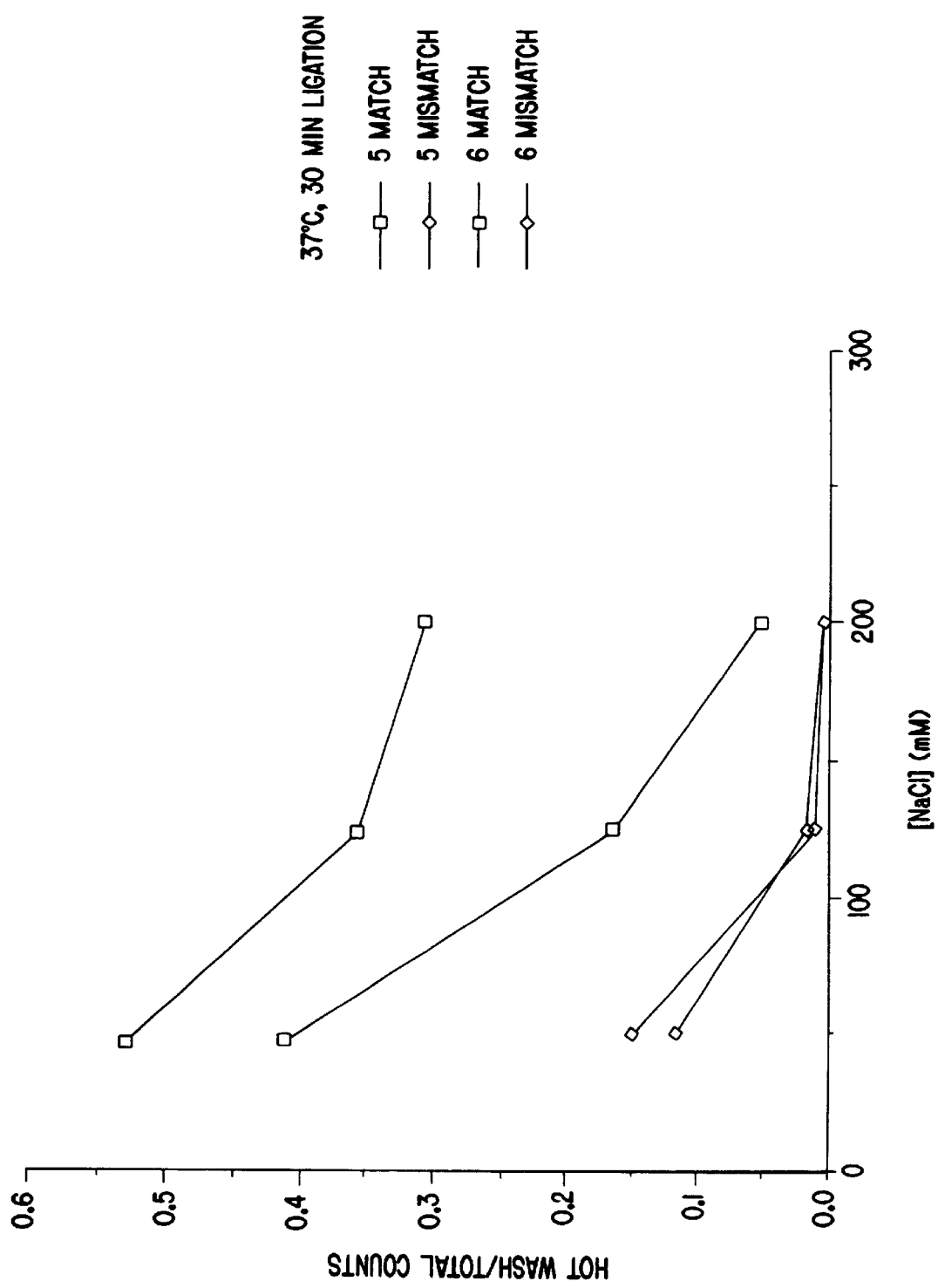
FIG. 11 Ligation efficiency of matches as compared to mismatches.
Figure 13C:
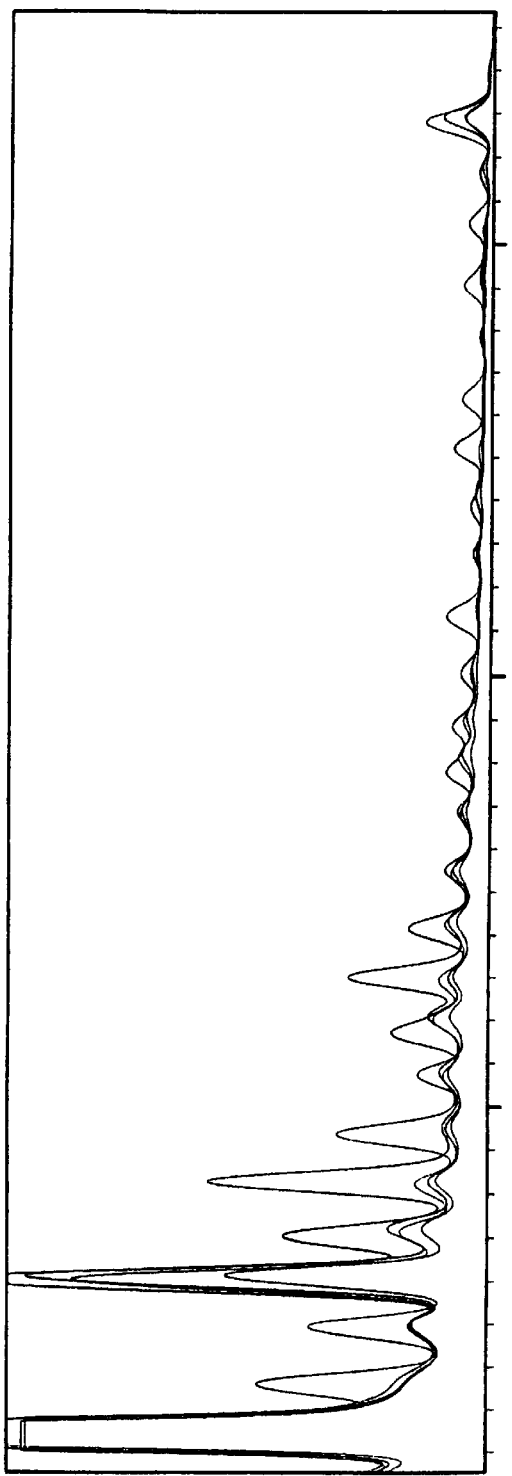
FIG. 13 Gel reader sequencing results from primer hybridization analysis.
Figure 13D:
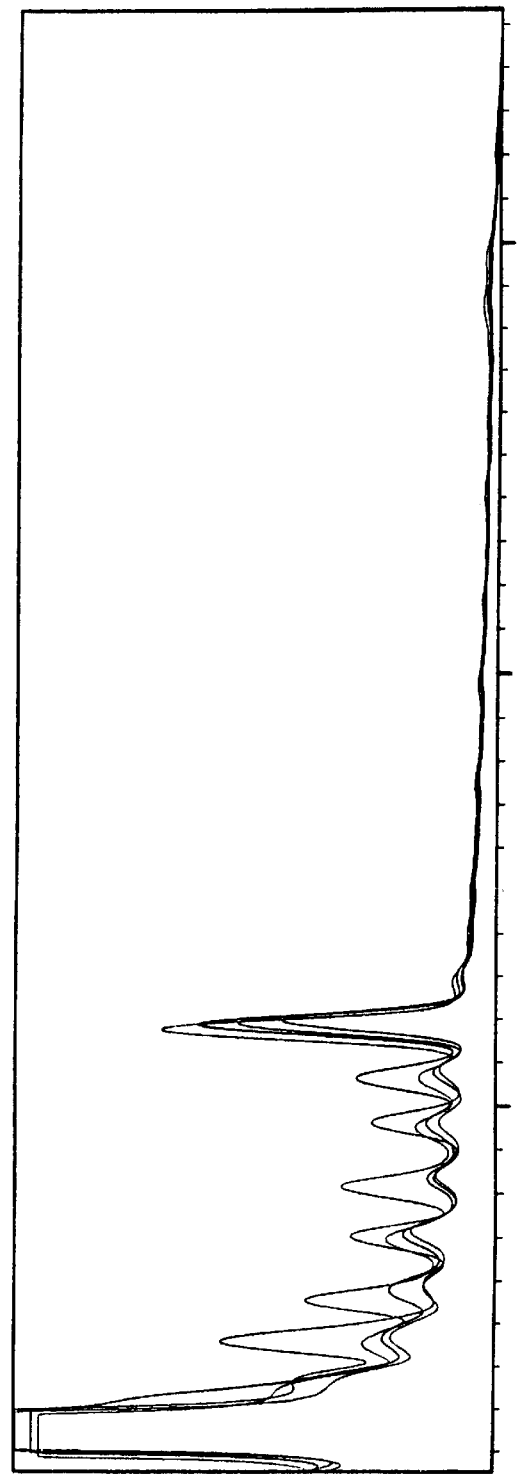
Figure 13E:
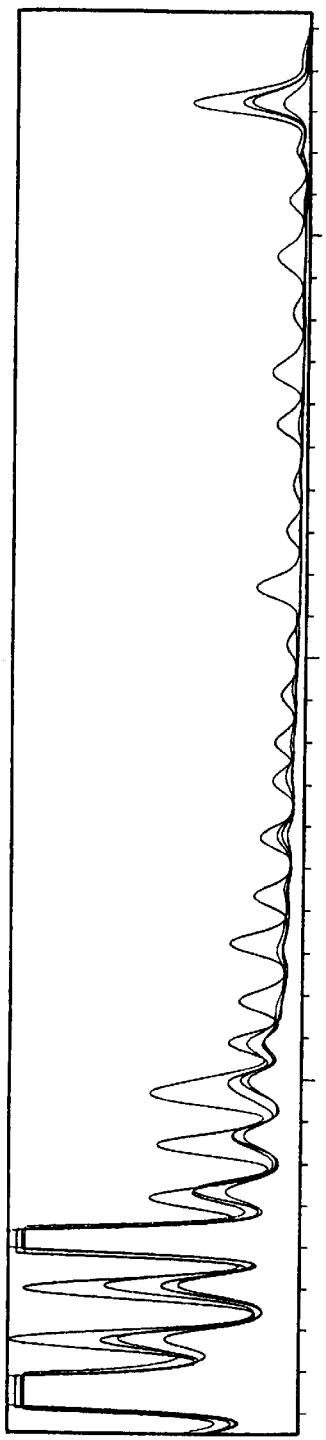
Figure 13F:
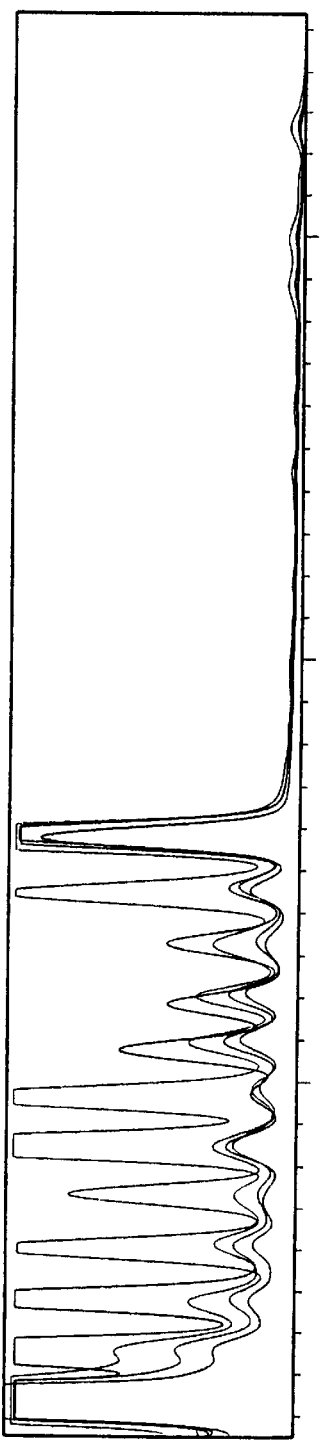
Figure 13G:
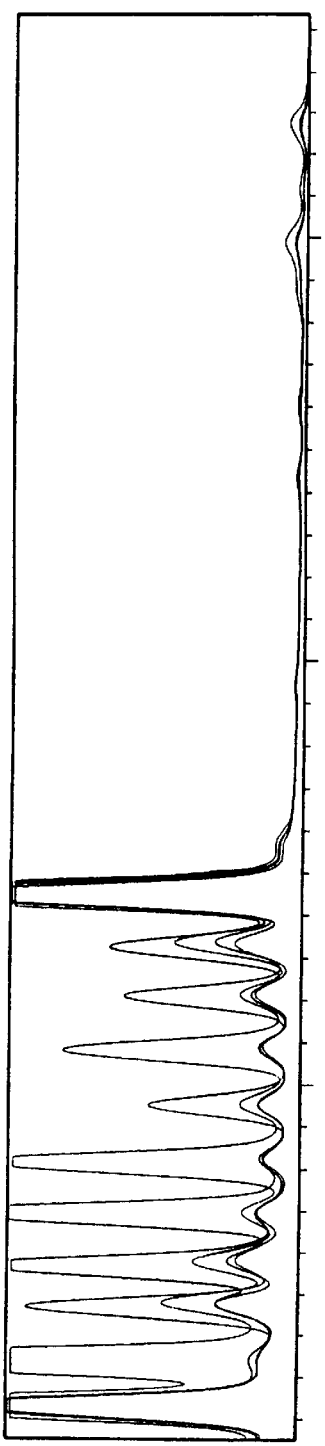
Figure 13H:
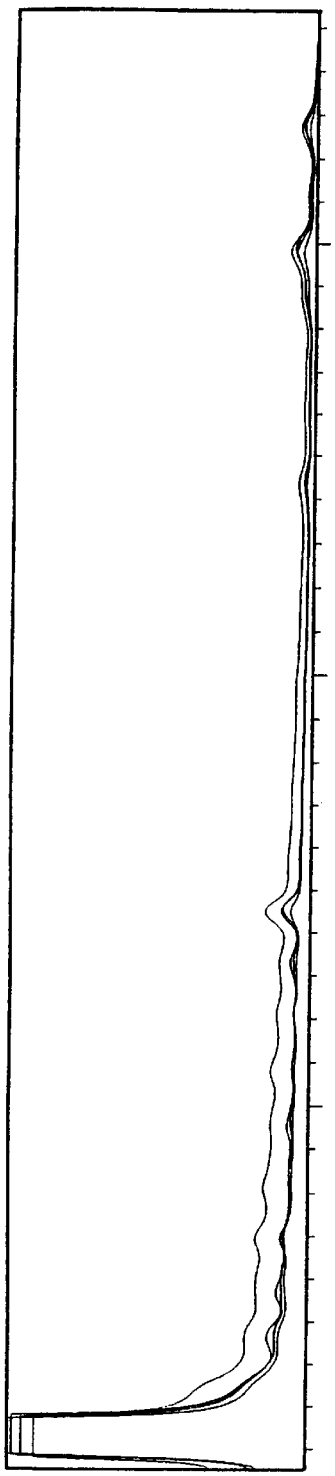
Figure 13I:
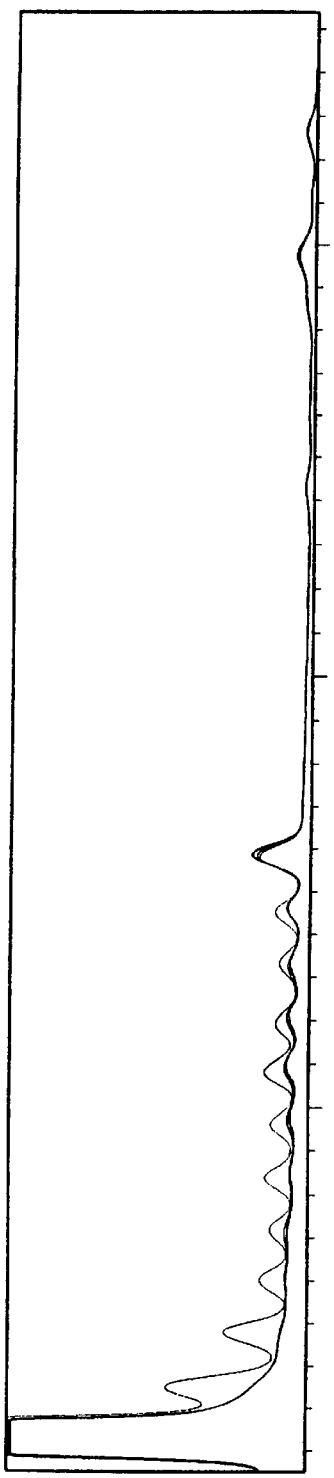
Figure 13J:
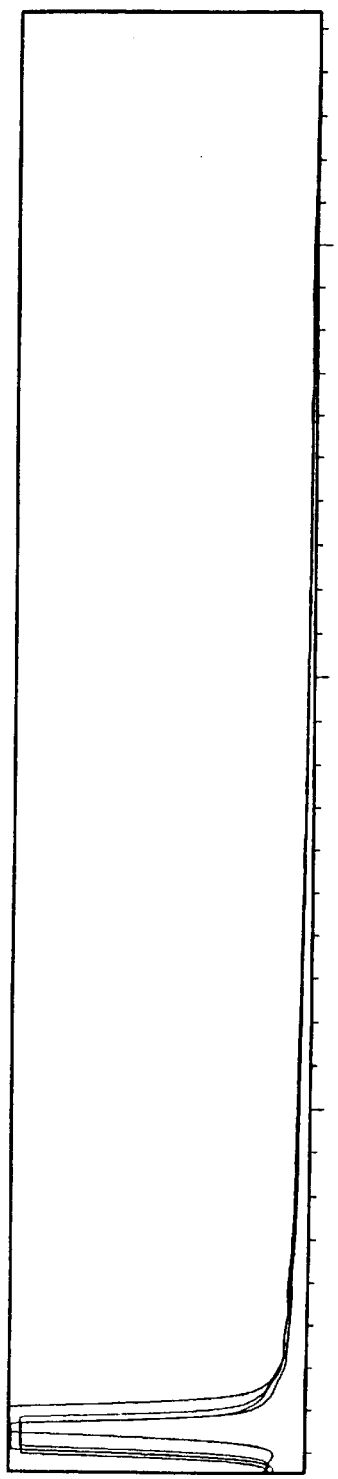

The biotinylated double-stranded probe was prepared in TE buffer by annealing the complimentary single strands together at 68° C. for five minutes followed by slow cooling to room temperature. A five-fold excess of monodisperse, polystyrene-coated magnetic beads (Dynal) coated with streptavidin was added to the double-stranded probe, which as then incubated with agitation at room temperature for 30 minutes. After ligation, the samples were subjected to two cold (4° C.) washes followed by one hot (90° C.) wash in TE buffer (FIG. 10). The ratio of $^{32}$P in the hot supernatant to the total amount of $^{32}$P was determined (FIG. 11). At high NaCl concentrations, mismatched target sequences were either not annealed or were removed in the cold washes. Under the same conditions, the matched target sequences were annealed and ligated to the probe. The final hot wash removed the non-biotinylated probe oligonucleotide. This oligonucleotide contained the labeled target if the target had been ligated to the probe.

Example 8
Compensating for Variations in Base Composition.

The Dependence on $T_M$ on base composition, and on base sequence may be overcome with the use of salts like tetramethyl ammonium halides or betaines. Alternatively, base analogs like 2,6-diamino purine and 5-bromo U can be used instead of A and T, respectively, to increase the stability of A–T base pairs, and derivatives like 7-deazaG can be used to decrease the stability of G–C base pairs. The initial Experiments shown in Table 2 indicate that the use of enzymes will eliminate many of the complications due to base sequences. This gives the approach a very significant advantage over non-enzymatic methods which require different conditions for each nucleic acid and are highly matched to GC content.

Another approach to compensate for differences in stability is to vary the base next to the stacking site. Experiments were performed to test the relative effects of all four bases in this position on overall hybridization discrimination and also on relative ligation discrimination other base analogs such as dU (deoxyuridine) and 7-deazaG may also be useful to suppress effects of secondary structure.

Example 9
DNA Ligation to Oligonucleotide Arrays.

*E. coli* and T4 DNA ligases can be used to covalently attach hybridized target nucleic acid to the correct immobilized oligonucleotide probe. This is a highly accurate and efficient process. Because ligase absolutely requires a correctly base paired 3' terminus, ligase will read only the 3'-terminal sequence of the target nucleic acid. After ligation, the resulting duplex will be 23 base pairs long and it will be possible to remove unhybridized, unligated target nucleic acid using fairly stringent washing conditions. Appropriately chosen positive and negative controls demonstrate the specificity of this method, such as arrays which are lacking a 5'-terminal phosphate adjacent to the 3' overhang since these probes will not ligate to the target nucleic acid.

There are a number of advantages to a ligation step. Physical specificity is supplanted by enzymatic specificity. Focusing on the 3' end of the target nucleic also minimize problems arising from stable secondary structures in the target DNA. DNA ligases are also used to covalently attach hybridized target DNA to the correct immobilized oligonucleotide probe. Several tests of the feasibility of the ligation method shown in FIG. 12. Biotinylated probes were attached at 5' ends (FIG. 12A) or 3' ends (FIG. 12B) to streptavidin-coated magnetic microbeads, and annealed with a shorter, complementary, constant sequence to produce duplexes with 5 or 6 base single-stranded overhangs. $^{32}$P-end labeled targets were allowed to hybridize to the probes. Free targets were removed by capturing the beads with a magnetic separator. DNA ligase was added and ligation was allowed to proceed at various salt concentrations. The samples were washed at room temperature, again manipulating the immobilized compounds with a magnetic separator to remove non-ligated material. Finally, samples were incubated at a temperature above the $T_m$ of the duplexes, and eluted single strand was retained after the remainder of the samples were removed by magnetic separation. The eluate at this point consisted of the ligated material. The fraction of ligation was estimated as the amount of $^{32}$P recovered in the high temperature wash versus the amount recovered in both the high and low temperature washes. Results indicated that salt conditions can be found where the ligation proceeds efficiently with perfectly matched 5 or 6 base overhangs, but not with G–T mismatches. The results of a more extensive set of similar experiments are shown in Tables 4–6.

Table 4 looks at the effect of the position of the mismatch and Table 5 examines the effect of base composition on the relative discrimination of perfect matches verses weakly destabilizing mismatches. These data demonstrate that effective discrimination between perfect matches and single mismatches occurs with all five base overhangs tested and that there is little if any effect of base composition on the amount of ligation seen or the effectiveness of match/mismatch discrimination. Thus, the serious problems of dealing with base composition effects on stability seen in ordinary SBH do not appear to be a problem for positional SBH. Furthermore, as the worst mismatch position was the one distal from the phosphodiester bond formed in the ligation reaction, any mismatches that survived in this position would be eliminated by a polymerase extension reaction. A polymerase such as Sequenase version 2, that has no 3'-endonuclease activity or terminal transferase activity would be useful in this regard. Gel electrophoresis analysis confirmed that the putative ligation products seen in these tests were indeed the actual products synthesized.

TABLE 4

Ligation Efficiency of Matched and Mismatched Duplexes in 0.2M NaCl at 37° C.
(SEQ ID NO 1)      3'-TCG AGA ACC TTG GCT-5'

| | | Ligation Efficiency | |
|---|---|---|---|
| | CTA CTA GGC TGC GTA GTC-5' | | (SEQ ID NO 2) |
| 5'-B- | GAT GAT CCG ACG CAT CAG AGC TC | 0.170 | (SEQ ID NO 3) |
| 5'-B- | GAT GAT CCG ACG CAT CAG AGC TT | 0.006 | (SEQ ID NO 4) |
| 5'-B- | GAT GAT CCG ACG CAT CAG AGC TA | 0.006 | (SEQ ID NO 7) |
| 5'-B- | GAT GAT CCG ACG CAT CAG AGC CC | 0.002 | (SEQ ID NO 8) |
| 5'-B- | GAT GAT CCG ACG CAT CAG AGT TC | 0.004 | (SEQ ID NO 9) |
| 5'-B- | GAT GAT CCG ACG CAT CAG AAC TC | 0.001 | (SEQ ID NO 10) |

TABLE 5

Ligation Efficiency of Matched and Mismatched Duplexes in 0.2M NaCl at 37° C. and its Dependance on AT Content of the Overhang

| | Overhang Sequences | AT Content | Ligation Efficiency |
|---|---|---|---|
| Match | GGCCC | 0/5 | 0.30 |
| Mismatch | GGCCT | | 0.03 |
| Match | AGCCC | 1/5 | 0.36 |
| Mismatch | AGCTC | | 0.02 |
| Match | AGCTC | 2/5 | 0.17 |
| Mismatch | AGCTT | | 0.01 |
| Match | AGATC | 3/5 | 0.24 |
| Mismatch | AGATT | | 0.01 |
| Match | ATATC | 4/5 | 0.17 |
| Mismatch | ATATT | | 0.01 |
| Match | ATATT | 5/5 | 0.31 |
| Mismatch | ATATC | | 0.02 |

TABLE 6

Increasing Discrimination by Sequencing Extension at 37° C.

| | | Litigation Efficiency | Litigation Extension (cpm) | |
|---|---|---|---|---|
| | | (percent) | (+) | (−) |
| | (SEQ ID NO 1)      3'-TCG AGA ACC TTG GCT-5'* | | | |
| | CTA CTA GGC TGC GTA GTC-5' (SEQ ID NO 2) | | | |
| 5'-B- | GAT GAT CCG ACG CAT CAG AGA TC (SEQ ID NO 11) | 0.24 | 4,934 | 29,500 |
| 5'-B- | GAT GAT CCG ACG CAT CAG AGC TT (SEQ ID NO 4) | 0.01 | 116 | 250 |
| | Discrimination = | x24 | x42 | x118 |
| | CTA CTA GGC TGC GTA GTC-5' (SEQ ID NO 2) | | | |
| 5'-B- | GAT GAT CCG ACG CAT CAG ATA TC (SEQ ID NO 12) | 0.17 | 12,250 | 25,200 |
| 5'-B- | GAT GAT CCG ACG CAT CAG ATA TT (SEQ ID NO 13) | 0.01 | 240 | 390 |
| | Discrimination = | x17 | x51 | x65 |

"B" = Biotin
"*" = radioactive label

The discrimination for the correct sequence is not as great with an external mismatch (which would be the most difficult case to discriminate) as with an internal mismatch (Table 6). A mismatch right at the ligation point would presumably offer the highest possible discrimination. In any event, the results shown are very promising. Already there is a level of discrimination with only 5 or 6 bases of overlap that is better than the discrimination seen in conventional SBH with 8 base overlaps.

Example 10

Capture and Sequencing of a Target Nucleic Acid.

A mixture of target DNA was prepared by mixing equal molar ratio of eight different oligos. For each sequencing reaction, one specific partially duplex probe and eight different targets were used. The sequence of the probe and the targets are shown in Tables 7 and 8.

TABLE 7

Duplex Probes Used

| (DF25) | 5'-F-GATGATCCGACGCATCAGCTGTG | (SEQ ID NO 14) |
|---|---|---|
| | 3'-CTACTAGGCTGCGTAGTC | (SEQ ID NO 2) |
| (DF37) | 5'-F-GATGATCCGACGCATCACTCAAC | (SEQ ID NO 15) |
| | 3'-CTACTAGGCTGCGTAGTG | (SEQ ID NO 2) |
| (DF22) | 5'-F-GATGATCCGACGCATCAGAATGT | (SEQ ID NO 16) |
| | 3'-CTACTAGGCTGCGTAGTC | (SEQ ID NO 2) |

TABLE 7-continued

Duplex Probes Used

| (DF28) | 5'-F-GATGATCCGACGCATCAGCCTAG | (SEQ ID NO 17) |
|---|---|---|
| | 3'-CTACTAGGCTGCGTAGTC | (SEQ ID NO 2) |
| (DF36) | 5'-F-GATGATCCGACGCATCAGTCGAC | (SEQ ID NO 18) |
| | 3'-CTACTAGGCTGCGTAGTC | (SEQ ID NO 2) |

TABLE 7-continued

Duplex Probes Used

| | | |
|---|---|---|
| (DF11a) | 5'-F-GATGATCCGACGCATCAC<u>AGCTC</u> | (SEQ ID NO 19) |
| | 3'-CTACTAGGCTGCGTAGTG | (SEQ ID NO 2) |
| (DF8a) | 5'-F-GATGATCCGACGCATCAA<u>GGCCC</u> | (SEQ ID NO 20) |
| | 3'-CTACTAGGCTGCGTAGTT | (SEQ ID NO 2) |

TABLE 8

Mixture of Targets

Match

| | | | |
|---|---|---|---|
| (NB4) | 3'-<u>TTAC</u>ACCGGATCGAGCCGGGTCGATCTAG | (DF22) | (SEQ ID NO 21) |
| (NB4.5) | 3'-<u>GGATC</u>GACCGGGTCGATCTAG | (DF28) | (SEQ ID NO 22) |
| (DF5) | 3'-<u>AGCTG</u>CCGGATCGAGCCGGGTCGATCTAG | (DF36) | (SEQ ID NO 23) |
| (TS10) | 3'-<u>TCGAG</u>AACCTTGGCT | (DF11a) | (SEQ ID NO 24) |
| (NB3.10) | 3'<u>CCGGG</u>TCGATCTAG | (DF8a) | (SEQ ID NO 25) |

Mismatch

| | | | |
|---|---|---|---|
| (NB3.4) | 3'-<u>CCGGA</u>TCAAGCCGGGTCGATCTAG | (DF8a) | (SEQ ID NO 26) |
| (NB3.7) | 3'-<u>TCAAG</u>CCGGGTCGATCTAG | (DF11a) | (SEQ ID NO 27) |
| (NB3.9) | 3'-<u>AGCCG</u>GGTCGATCTAG | (DF36) | (SEQ ID NO 28) |

Two pmol of each of the two duplex-probe-forming oligonucleotides and 1.5 pmol of each of the eight different targets were mixed in a 10 µl volume containing 2 µl of Sequenase buffer stock (200 mM Tris-HCl, pH 7.5, 100 mM MgCl$_2$, and 250 mM NaCl) from the Sequenase kit. The annealing mixture was heated to 65° C. and allowed to cool slowly to room temperature. While the reaction mixture was kept on ice, 1 µl 0.1 M dithiothreitol solution, 1 µl Mn buffer (0.15 M sodium isocitrate and 0.1 M MnCl$_2$), and 2 µl of diluted Sequenase (1.5 units) were mixed, and the 2 µl of reaction mixture was added to each of the four termination mixes at room temperature (each consisting of 3 µl of the appropriate termination mix: 16 µM dATP, 16 µM dCTP, 16 µM dGTP, 16 µM dTTP and 3.2 µM of one of the four ddNTPs, in 50 mM NaCl). The reaction mixtures were further incubated at room temperature for 5 minutes, and terminated with the addition of 4 µl of Pharmacia stop mix (deionized formamide containing dextran blue 6 mg/ml). Samples were denatured at 90–95° C. for 3 minutes and stored on ice prior to loading. Sequencing samples were analyzed on an ALF DNA sequencer (Pharmacia Biotech; Piscataway, N.J.) using a 10% polyacrylamide gel containing 7 M urea and 0.6×TBE. Sequencing results from the gel reader are shown in FIG. 13 and summarized in Table 9. Matched targets hybridized correctly and are sequenced, whereas mismatched targets do not hybridize and are not sequenced.

TABLE 9

Summary of Hybridization Data

| Reaction | Hybridization | Sequence | Comment |
|---|---|---|---|
| 1 | Probe: DF25 Target: mixture | No | mismatch |
| 2 | Probe: DF37 Target: mixture | No | mismatch |
| 3 | Probe: DF22 Target: mixture | Yes | match |
| 4 | Probe: DF28 Target: mixture | Yes | match |
| 5 | Probe: DF36 Target: mixture | Yes | match |
| 6 | Probe: DF11a Target: mixture | Yes | match |
| 7 | Probe: DF8a Target: mixture | Yes | match |
| 8 | Probe: DF8a Target: NB3.4 | No | mismatch |

TABLE 9-continued

Summary of Hybridization Data

| Reaction | Hybridization | Sequence | Comment |
|---|---|---|---|
| 9 | Probe: DF8a Target: TS12 | No | mismatch |
| 10 | Probe: DF37 Target: DF5 | No | mismatch |

Example 11

Elongation of Nucleic Acids Bound to Solid Supports.

Elongation was carried out either by using Sequenase version 2.0 kit or an AutoRead sequencing kit (Pharmacia Biotech; Piscataway, N.J.) employing T7 DNA polymerase. Elongation of the immobilized single-stranded DNA target was performed with reagents from the sequencing kits for Sequenase Version 2.0 or T7 DNA polymerase. A duplex DNA probe containing a 5-base 3' overhang was used as a primer. The duplex has a 5'-fluorescein labeled 23-mer, containing an 18-base 5' constant region and a 5-base 3' variable region (which has the same sequence as the 5'-end of the corresponding nonbiotinylated primer for PCR amplification of target DNA, and an 18-mer complementary to the constant region of the 23-mer. The duplex was formed by annealing 20 pmol of each of the two oligonucleotides in a 10 µl volume containing 2 µl of Sequenase buffer stock (200 mM Tris-HCl, pH 7.5, 100 mM MgCl$_2$, and 250 mM NaCl) from the Sequenase kit or in a 13 µl volume containing 2 µl of the annealing buffer (1 M Tris-HCl, pH 7.6, 100 mM MgCl$_2$) from the AutoRead sequencing kit. The annealing mixture was heated to 65° C. and allowed to cool slowly to 37° C. over a 20–30 minute time period. The duplex primer was annealed with the immobilized single-stranded DNA target by adding the annealing mixture to the DNA-containing magnetic beads and the resulting mixture was further incubated at 37° C. for 5 minutes, room temperature for 10 minutes, and finally 0° C. for at least 5 minutes. For Sequenase reactions, 1 µl 0.1 M dithiothreitol solution, 1 µl Mn buffer (0.15 M sodium isocitrate and 0.1 M MnCl$_2$) for the relative short target, and 2 µl of diluted Sequenase (1.5 units) were added, and the reaction mixture was divided into four ice cold termination mixes (each consists of 3 µl of the appropriate termination mix: 80 µM dATP, 80 µM dCTP, 80 µM dGTP, 80 µM dTTP and 8 µM of one of the four ddNTPs, in 50 mM NaCl). For T7 DNA polymerase reactions, 1 µl of extension buffer (40 mM McCl$_2$, pH 7.5, 304 mM citric acid and 324 mM DTT) and 1 µl of T7 DNA polymerase (8 units) were mixed, and the reaction volume was split into four ice cold termination mixes (each consisting of 1 l DMSO and 3 µl of the appropriate termination mix: 1 mM dATP, 1 mM dCTP, 1 mM dGTP, 1 mM dTTP and 5 μM of one of the four ddNTPs, in 50 mM NaCl and 40 mM Tris-HCl, pH 7.4). The reaction mixtures for both enzymes were further incubated at 0° C. for 5 minutes, room temperature for 5 minutes and 37° C. for 5 minutes. After the completion of extension, the supernatant was removed, and the magnetic beads were re-suspended in 10 μl of Pharmacia stop mix. Samples were denatured at 90–95° C. for 5 minutes (under this harsh condition, both DNA template and the dideoxy fragments are released from the beads) and stored on ice prior to loading. A control experiment was performed in parallel using a 18-mer complementary to the 3' end of target DNA as the sequencing primer instead of the duplex probe and the annealing of 18-mer to its target was carried out in a similar way as the annealing of the duplex probe.

Example 12
Chain Elongation of Target Sequences.

Sequencing of immobilized target DNA can be performed with Sequenase Version 2.0. A total of 5 elongation reactions, one with each of 4 dideoxy nucleotides and one with all four simultaneously, are performed. A sequencing solution, containing (40 mM Tris-HCl, pH 7.5, 20 mM $MgCl_2$, and 50 mM NaCl, 10 mM dithiothreitol solution, 15 mM sodium isocitrate and 10 mM $MnCl_2$, and 100 u/ml of Sequenase (1.5 units) is added to the hybridized target DNA. dATP, dCTP, dGTP and dTTP are added to 20 uM to initiate the elongation reaction. In the separate reactions, one of four ddNTP is added to reach a concentration of 8 μM. In the combined reaction all four ddNTP are added to the reaction to 8 μM each. The reaction mixtures were incubated at 0° C. for 5 minutes room temperature for 5 minutes and 37° C. for 5 minutes. After the completion of extension, the supernatant was removed and the elongated DNA washed with 2 mM EDTA to terminate elongation reactions. Reaction products are analyzed by mass spectrometry.

Example 13
Capillary Electrophoretic Analysis of Target Nucleic Acid.

Molecular weights of target sequences may also be determined by capillary electrophoresis. A single laser capillary electrophoresis instrument can be used to monitor the performance of sample preparations in high performance capillary electrophoresis sequencing. This instrument is designed so that it is easily converted to multiple channel (wavelengths) detection.

An individual element of the sample array may be engineered directly to serve as the sample input to a capillary. Typical capillaries are 250 microns o.d. and 75 microns i.d. The sample is heated or denatured to release the DNA ladder into a liquid droplet. the silicon array surfaces is ideal for this purpose. The capillary can be brought into contact with the droplet to load the sample.

To facilitate loading of large numbers of samples simultaneously or sequentially, there are two basic methods. With 250 micron o.d. capillaries it is feasible to match the dimensions of the target array and the capillary array. Then the two could be brought into contact manually or even by a robot arm using a jig to assure accurate alignment. An electrode may be engineered directly into each sector of the silicon surface so that sample loading would only require contact between the surface and the capillary array.

The second method is based on an inexpensive collection system to capture fractions eluted from high performance capillary electrophoresis. Dilution is avoided by using designs which allow sample collection without a perpendicular sheath flow. The same apparatus designed as a sample collector can also serve inversely as a sample loader. In this case, each row of the sample array, equipped with electrodes, is used directly to load samples automatically on a row of capillaries. Using either method, sequence information is determined and the target sequence constructed.

Example 14
Mass Spectrometry of Nucleic Acids.

Nucleic acids to be analyzed by mass spectrometry were redissolved in ultrapure water (MilliQ, Millipore) using amounts to obtain a concentration of 10 pmoles/μl as stock solution. An aliquot (1 μl) of this concentration or a dilution in ultrapure water was mixed with 1 μl of the matrix solution on a flat metal surface serving as the probe tip and dried with a fan using cold air. In some experiments, cation-ion exchange beads in the acid form were added to the mixture of matrix and sample solution to stabilize ions formed during analysis.

Figure 14:
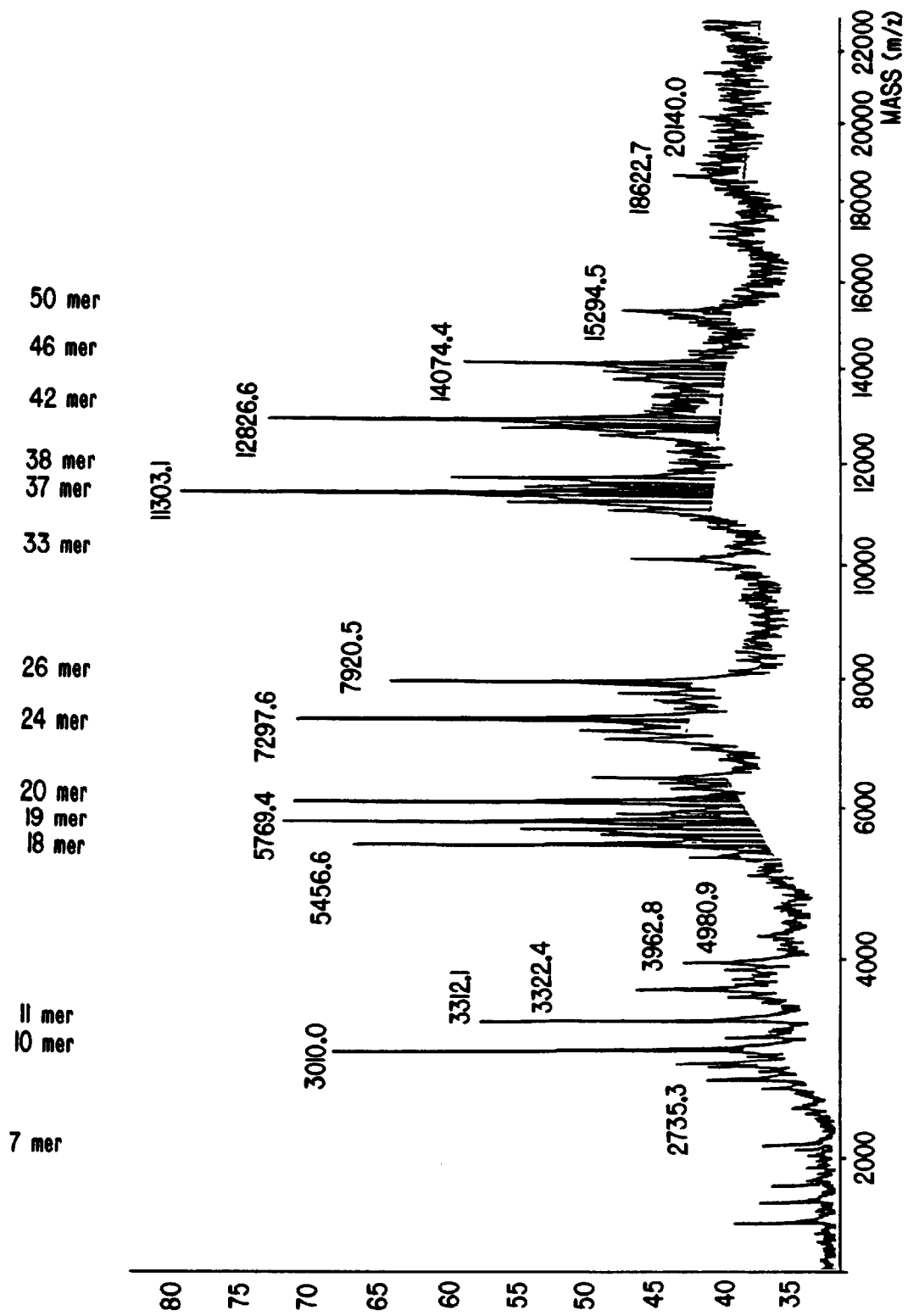
FIG. 14 Mass spectrometry of oligonucleotide ladder.

MALDI-TOF spectra were obtained on different commercial instruments such as Vision 2000 (Finnigan-MAT), VG TofSpec (Fisons Instruments), LaserTec Research (Vestec). The conditions were linear negative ion mode with an acceleration voltage of 25 kV. Mass calibration was done externally and generally achieved by using defined peptides of appropriate mass range such as insulin, gramicidin S, trypsinogen, bovine serum albumen and cytochrome C. All spectra were generated by employing a nitrogen laser with 5 nanosecond pulses at a wavelength of 337 nm. Laser energy varied between $10^6$ and $10^7$ W/cm². To improve signal-to-noise ratio generally, the intensities of 10 to 30 laser shots were accumulated. The output of a typical mass spectrometry showing discrimination between nucleic acids which differ by one base is shown in FIG. 14.

Example 15
Sequence Determination from Mass Spectrometry.

Elongation of a target nucleic acid, in the presence of dideoxy chain terminating nucleotides, generated four families of chain-terminated fragments. The mass difference per nucleotide addition is 289.19 for dpC, 313.21 for dpA, 329.21 for dpG and 304.20 for dpT, respectively. Comparison of the mass differences measured between fragments with the known masses of each nucleotide the nucleic acid sequence can be determined. Nucleic acid may also be sequenced by performing polymerase chain elongation in four separate reactions each with one dideoxy chain terminating nucleotide. To examine mass differences, 13 oligonucleotides from 7 to 50 bases in length were analyzed by MALDI-TOF mass spectrometry. The correlation of calculated molecular weights of the ddT fragments of a Sanger sequencing reaction and their experimentally verified weights are shown in Table 10. When the mass spectrometry data from all four chain termination reactions are combined, the molecular weight difference between two adjacent peaks can be use to determine the sequence.

TABLE 10

Summary of Molecular Weights Expected v. Measured

| Fragment (n-mer) | Calculated Mass | Experimental Mass | Difference |
|---|---|---|---|
| 7-mer | 2104.45 | 2119.9 | +15.4 |
| 10-mer | 3011.04 | 3026.1 | +15.1 |
| 11-mer | 3315.24 | 3330.1 | +14.9 |
| 19-mer | 5771.82 | 5788.0 | +16.2 |
| 20-mer | 6076.02 | 6093.8 | +17.8 |
| 24-mer | 7311.82 | 7374.9 | +63.1 |
| 26-mer | 7945.22 | 7960.9 | +15.7 |

TABLE 10-continued

Summary of Molecular Weights Expected v. Measured

| Fragment (n-mer) | Calculated Mass | Experimental Mass | Difference |
|---|---|---|---|
| 33-mer | 10112.63 | 10125.3 | +12.7 |
| 37-mer | 11348.43 | 11361.4 | +13.0 |
| 38-mer | 11652.62 | 11670.2 | +17.6 |
| 42-mer | 12872.42 | 12888.3 | +15.9 |
| 46-mer | 14108.22 | 14125.0 | +16.8 |
| 50-mer | 15344.02 | 15362.6 | +18.6 |

Example 16
Reduced Pass Sequencing.

To maximize the use of PSBH arrays to produce Sanger ladders, the sequence of a target should be covered as completely as possible with the lowest amount of initial sequencing redundancy. This will maximize the performance of individual elements of the arrays and maximize the amount of useful sequence data obtained each time an array is used. With an unknown DNA, a full array of 1024 elements (Mwo I or BsiY I cleavage) or 256 elements (TspR I cleavage) is used. A 50 kb target DNA is cut into about 64 fragments by Mwo I or BsiY I or 30 fragments by TspR I, respectively. Each fragment has two ends both of which can be captured independently. The coverage of each array after capture and ignoring degeneracies is 128/1024 sites in the first case and 60/256 sites in the second case. Direct use of such an array to blindly deliver samples element by element for mass spectrometry sequencing would be inefficient since most array elements will have no samples.

In one method, phosphatased double-stranded targets are used at high concentrations to saturate each array element that detects a sample. The target is ligated to make the capture irreversible. Next a different sample mixture is exposed to the array and subsequently ligated in place. This process is repeated four or five times until most of the elements of the array contain a unique sample. Any tandem target-target complexes will be removed by a subsequent ligating step because all of the targets are phosphatased.

Alternatively, the array may be monitored by confocal microscopy after the elongation reactions. This should reveal which elements contain elongated nucleic acids and this information is communicated to an automated robotic system that is ultimately used to load the samples onto a mass spectrometry analyzer.

Example 17
Synthesis of Mass Modified Nucleic Acid Primers.

Mass modification at the 5' sugar: Oligonucleotides were synthesized by standard automated DNA synthesis using β-cyanoethylphosphoamidites and a 5'-amino group introduced at the end of solid phase DNA synthesis. The total amount of an oligonucleotide synthesis, starting with 0.25 micromoles CPG-bound nucleoside, is deprotected with concentrated aqueous ammonia, purified via OligoPAK™ Cartridges (Millipore; Bedford, Mass.) and lyophilized. This material with a 5'-terminal amino group is dissolved in 100 μl absolute N,N-dimethylformamide (DMF) and condensed with 10 μmole N-Fmoc-glycine pentafluorophenyl ester for 60 minutes at 25° C. After ethanol precipitation and centrifugation, the Fmoc group is cleaved off by a 10 minute treatment with 100 μl of a solution of 20% piperidine in N,N-dimethylformamide. Excess piperidine, DMF and the cleavage product from the Fmoc group are removed by ethanol precipitation and the precipitate lyophilized from 10 mM TEAA buffer pH 7.2. This material is now either used as primer for the Sanger DNA sequencing reactions or one or more glycine residues (or other suitable protected amino acid active esters) are added to create a series of mass-modified primer oligonucleotides suitable for Sanger DNA or RNA sequencing.

Mass modification at the heterocyclic base with glycine: Starting material was 5-(3-aminopropynyl-1)-3'5'-di-p-tolyldeoxyuridine prepared and 3'5'-de-O-acylated (Haralambidis et al., Nuc. Acids Res. 15:4857–76, 1987). 0.281 g (1.0 mmol) 5-(3-aminopropynyl-1)-2'deoxyuridine were reacted with 0.927 g (2.0 mmol) N-Fmoc-glycine pentafluorophenylester in 5 ml absolute N,N-dimethylformamide in the presence of 0.129 g (1 mmol; 174 μl) N,N-diisopropylethylamine for 60 minutes at room temperature. Solvents were removed by rotary evaporation and the product was purified by silica gel chromatography (Kieselgel 60, Merck; column: 2.5×50 cm, elution with chloroform/methanol mixtures). Yield was 0.44 g (0.78 mmol; 78%). To add another glycine residue, the Fmoc group is removed with a 20 minutes treatment with 20% solution of piperidine in DMF, evaporated in vacuo and the remaining solid material extracted three times with 20 ml ethylacetate. After having removed the remaining ethylacetate, N-Fmoc-glycine pentafluorophenylester is coupled as described above. 5-(3(N-Fmoc-glycyl)-amidopropynyl-1)-2'-deoxyuridine is transformed into the 5'-O-dimethoxytritylated nucleoside-3'-O-β-cyanoethyl-N,N-diisopropylphosphoamidite and incorporated into automated oligonucleotide synthesis. This glycine modified thymidine analogue building block for chemical DNA synthesis can be used to substitute one or more of the thymidine/uridine nucleotides in the nucleic acid primer sequence. The Fmoc group is removed at the end of the solid phase synthesis with a 20 minute treatment with a 20% solution of piperidine in DMF at room temperature. DMF is removed by a washing step with acetonitrile and the oligonucleotide deprotected and purified.

Mass modification at the heterocyclic base with β-alanine: 0.281 g (1.0 -mmol) 5-(3-Aminopropynyl-1)-2'-deoxyuridine was reacted with N-Fmoc-β-alanine pentafluorophenylester (0.955 g; 2.0 mmol) in 5 ml N,N-dimethylformamide (DMF) in the presence of 0.129 g (174 μl; 1.0 mmol) N,N-disopropylethylamine for 60 minutes at room temperature. Solvents were removed and the product purified by silica gel chromatography. Yield was 0.425 g (0.74 mmol; 74%). Another β-alanine moiety can be added in exactly the same way after removal of the Fmoc group. The preparation of the 5'-O-dimethoxytritylated nucleoside-3'-O-β-cyanoethyl-N,N-diisopropylphosphoamidite from 5-(3-(N-Fmoc-β-alanyl)-amidopropynyl-1)-2'—deoxyuridine and incorporation into automated oligonucleotide synthesis is performed under standard conditions. This building block can substitute for any of the thymidine/uridine residues in the nucleic acid primer sequence.

Mass modification at the heterocyclic base with ethylene monomethyl ether: 5-(3-aminopropynyl-1)-2'-deoxyuridine was used as a nucleosidic component in this example. 7.61 g (100.0 mmol) freshly distilled ethylene glycol monomethyl ether dissolved in 50 ml absolute pyridine was reacted with 10.01 g (100.0 mmol) recrystallized succinic anhydride in the presence of 1.22 g (10.0 mmol) 4-N,N—dimethylaminopyridine overnight at room temperature. The reaction was terminated by the addition of water (5.0 ml), the reaction mixture evaporated in vacuo, co-evaporated twice with dry toluene (20 ml each) and the residue redissolved in 100 ml dichloromethane. The solution was twice extracted successively with 10% aqueous citric acid (2×20 ml) and once with water (20 ml) and the organic phase dried over anhydrous sodium sulfate. The organic phase was evaporated in vacuo. Residue was redissolved in 50 ml dichloromethane and precipitated into 500 ml pentane and the precipitate dried in vacuo. Yield was 13.12 g (74.0 mmol; 74%). 8.86 g (50.0 mmol) of succinylated ethylene glycol monomethyl ether was dissolved in 100 ml dioxane containing 5% dry pyridine (5 ml) and 6.96 g (50.0 mmol) 4-nitrophenol and 10.32 g (50.0 mmol) dicyclohexylcarbodiimide was added and the reaction run at room temperature for 4 hours. Dicyclohexylurea was removed by filtration, the filtrate evaporated in vacuo and the residue redissolved in 50 ml anhydrous DMF. 12.5 ml (about 12.5 mmol 4-nitrophenylester) of this solution was used to dissolve 2.81 g (10.0 mmol) 5-(3-aminopropynyl-1)-2'-deoxyuridine. The reaction was performed in the presence of 1.01 g (10.0 mmol; 1.4 ml) triethylamine overnight at room temperature. The reaction mixture was evaporated in vacuo, co-evaporated with toluene, redissolved in dichloromethane and chromatographed on silicagel (Si60, Merck; column 4×50cm) with dichloromethane/methanol mixtures. Fractions containing the desired compound were collected, evaporated, redissolved in 25 ml dichloromethane and precipitated into 250 ml pentane. The dried precipitate of 5-(3-N-(O-succinyl ethylene glycol monomethyl ether)-amidopropynyl-1)-2'-deoxyuridine (yield 65%) is 5'-O-dimethoxytritylated and transformed into the nucleoside-3'-O-β-cyanoethyl-N,N-diisopropylphosphoamidite and incorporated as a building block in the automated oligonucleotide synthesis according to standard procedures. The mass-modified nucleotide can substitute for one or more of the thymidine/uridine residues in the nucleic acid primer sequence. Deprotection and purification of the primer oligonucleotide also follows standard procedures.

Mass modification at the heterocyclic base with diethylene glycol monomethyl ether: Nucleosidic starting material was as in previous examples, 5-(3-aminopropynyl-1)-2'-deoxyuridine. 12.02 g (100.0 mmol) freshly distilled diethylene glycol monomethyl ether dissolved in 50 ml absolute pyridine was reacted with 10.01 g (100.0 mmol) recrystallized succinic anhydride in the presence of 1.22 g (10.0 mmol) 4-N,N-dimethylaminopyridine (DMAP) overnight at room temperature. Yield was 18.35 g (82.3 mmol; 82.3%). 11.06 g (50.0 mmol) of succinylated diethylene glycol monomethyl ether was transformed into the 4-nitrophenylester and, subsequently, 12.5 mmol was reacted with 2.81 g (10.0 mmol) of 5-(3-aminopropynyl-1)-2'-deoxyuridine. Yield after silica gel column chromatography and precipitation into pentane was 3.34 g (6.9 mmol; 69%). After dimethoxytritylation and transformation into the nucleoside-β-cyanoethylphosphoamidite, the mass-modified building block is incorporated into automated chemical DNA synthesis. Within the sequence of the nucleic acid primer, one or more of the thymidine/uridine residues can be substituted by this mass-modified nucleotide.

Mass Modification at the heterocyclic base with glycine: Starting material was $N^6$-benzoyl-8-bromo-5'-O-(4,4'-dimethoxytrityl)-2'deoxyadenosine (Singh et al., Nuc. Acids Res. 18:3339–45, 1990). 632.5 mg (1.0 mmol) of this 8-bromo-deoxyadenosine derivative was suspended in 5 ml absolute ethanol and reacted with 251.2 mg (2.0 mmol) glycine methyl ester (hydrochloride) in the presence of 241.4 mg (2.1 mmol; 366 µl) N,N-diisopropylethylamine and refluxed until the starting nucleosidic material had disappeared (4–6 hours) as checked by thin layer chromatography (TLC). The solvent was evaporated and the residue purified by silica gel chromatography (column 2.5×50cm) using solvent mixtures of chloroform/methanol containing 0.1% pyridine. Product fractions were combined, the solvent evaporated, the fractions dissolved in 5 ml dichloromethane and precipitated into 100 ml pentane. Yield was 487 mg (0.76 mmol; 76%). Transformation into the corresponding nucleoside-β-cyanoethylphospho amidite and integration into automated chemical DNA synthesis is performed under standard conditions. During final deprotection with aqueous concentrated ammonia, the methyl group is removed from the glycine moiety. The mass-modified building block can substitute one or more deoxyadenosine/adenosine residues in the nucleic acid primer sequence.

Mass modification at the heterocyclic base with glycylglycine: 632.5 mg (1.0 mmol) $N^6$-Benzoyl-8-bromo-5'-O-(4,4'dimeethoxytrityl)2'-deoxyadenosine was suspended in 5 ml absolute ethanol and reacted with 324.3 mg (2.0 mmol) glycyl-glycine methyl ester in the presence of 241.4 mg (2.1 mmol; 366 µl) N,N-diisopropylethylamine. The mixture was refluxed and completeness of the reaction checked by TLC. Yield after silica gel column chromatography and precipitation into pentane was 464 mg (0.65 mmol; 65%). Transformation into the nucleoside-β-cyanoethylphosphoamidite and into synthetic oligonucleotides is done according to standard procedures.

Mass Modification at the heterocyclic base with glycol monomethyl ether: Starting material was 5'-O-(4,4-dimethoxytrityl)-2'-amino-2'-deoxythymidine synthesized (Verheyden et al., J. Org. Chem. 36:250–54, 1971; Sasaki et al, J. Org. Chem. 41:3138–43, 1976; Imazawa et al., J. Org. Chem. 44:2039–41, 1979; Hobbs et al., J. Org. Chem. 42:714–19, 1976; Ikehara et al., Chem. Pharm. Bull. Japan 26:240–44, 1978). 5'-O-(4,4-Dimethoxytrityl)-2'-amino-2'-deoxythymidine (559.62 mg; 1.0 mmol) was reacted with 2.0 mmol of the 4-nitrophenyl ester of succinylated ethylene glycol monomethyl ether in 10 ml dry DMF in the presence of 1.0 mmol (140 µl) triethylamine for 18 hours at room temperature. The reaction mixture was evaporated in vacuo, co-evaporated with toluene, redissolved in dichloromethane and purified by silica gel chromatography (Si60, Merck; column: 2.5×50 cm; eluent: chloroform/methanol mixtures containing 0.1% triethylamine). The product containing fractions were combined, evaporated and precipitated into pentane. Yield was 524 mg (0.73 mmol; 73%). Transformation into the nucleoside-β-cyanoethyl-N,N-diisopropylphosphoamidite and incorporation into the automated chemical DNA synthesis protocol is performed by standard procedures. The mass-modified deoxythymidine derivative can substitute for one or more of the thymidine residues in the nucleic acid primer.

In an analogous way, by employing the 4-nitrophenyl ester of succinylated diethylene glycol monomethyl ether and triethylene glycol monomethyl ether, the corresponding mass-modified oligonucleotides are prepared. In the case of only one incorporated mass-modified nucleoside within the sequence, the mass difference between the ethylene, diethylene and triethylene glycol derivatives is 44.05, 88.1 and 132.15 daltons, respectively.

Mass modification at the heterocyclic base by alkylation: Phosphorothioate-containing oligonucleotides were prepared (Gait et al., Nuc. Acids Res. 19:1183, 1991). One, several or all internucleotide linkages can be modified in this way. The (−)M13 nucleic acid primer sequence (17-mer) 5'-dGTAAAACGACGGCCAGT (SEQ ID NO 29) is synthesized in 0.25 µmole scale on a DNA synthesizer and one phosphorothioate group introduced after the final synthesis cycle (G to T coupling). Sulfurization, deprotection and purification followed standard protocols. Yield was 31.4 nmole (12.6% overall yield), corresponding to 31.4 nmole phosphorothioate groups. Alkylation was performed by dissolving the residue in 31.4 μl TE buffer (0.01 M Tris pH 8.0, 0.001 M EDTA) and by adding 16 μl of a solution of 20 mM solution of 2-iodoethanol (320 nmole; 10-fold excess with respect to phosphorothioate diesters) in N,N-dimethylformamide (DMF). The alkylated oligonucleotide was purified by standard reversed phase HPLC (RP-18 Ultraphere, Beckman; column: 4.5×250 mm; 100 mM triethyl ammonium acetate, pH 7.0 and a gradient of 5 to 40% acetonitrile).

In a variation of this procedure, the nucleic acid primer containing one or more phosphorothioate phosphodiester bond is used in the Sanger sequencing reactions. The primer-extension products of the four sequencing reactions are purified, cleaved off the solid support, lyophilized and dissolved in 4 μl each of TE buffer pH 8.0 and alkylated by addition of 2 μl of a 20 mM solution of 2-iodoethanol in DMF. It is then analyzed by ES and/or MALDI mass spectrometry.

In an analogous way, employing instead of 2-iodoethanol, e.g., 3-iodopropanol, 4-iodobutanol mass-modified nucleic acid primer are obtained with a mass difference of 14.03, 28.06 and 42.03 daltons respectively compared to the unmodified phosphorothioate phosphodiester-containing oligonucleotide.

Example 18
Mass Modification of Nucleotide Triphosphates.

Mass modification of nucleotide triphosphates at the 2' and 3' amino function: Starting material was 2'-azido-2'-deoxyuridine prepared according to literature (Verheyden et al., J. Org. Chem. 36:250, 1971), which was 4,4-dimethoxytritylated at 5'-OH with 4,4-dimethoxytrityl chloride in pyridine and acetylated at 3'-OH with acetic anhydride in a one-pot reaction using standard reaction conditions. With 191 mg (0.71 mmol) 2'-azido-2'-deoxyuridine as starting material, 396 mg (0.65 mmol; 90.8%) 5'-O-(4,4-dimethoxytrityl)-3'-O-acetyl- 2'-azido-2'-deoxyuridine was obtained after purification via silica gel chromatography. Reduction of the azido group was performed (Barta et al., Tetrahedron 46:587–94, 1990). Yield of 5'-O-(4,4-dimethoxytrityl)-3'-O-acetyl-2'-amino-2'-deoxyuridine after silica gel chromatography was 288 mg (0.49 mmol; 76%). This protected 2'-amino-2'-deoxyuridine derivative (588 mg, 1.0 mmol) was reacted with 2 equivalents (927 mg; 2.0 mmol) N-Fmoc-glycine pentafluorophenyl ester in 10 ml dry DMF overnight at room temperature in the presence of 1.0 mmol (174 μl) N,N-diisopropylethylamine. Solvents were removed by evaporation in vacuo and the residue purified by silica gel chromatography. Yield was 711 mg (0.71 mmol; 82%). Detritylation was achieved by a one hour treatment with 80% aqueous acetic acid at room temperature. The residue was evaporated to dryness, co-evaporated twice with toluene, suspended in 1 ml dry acetonitrile and 5'-phosphorylated with $POCl_3$ and directly transformed in a one-pot reaction to the 5'-triphosphate using 3 ml of a 0.5 M solution (1.5 mmol) tetra (tri-n-butylammonium) pyrophosphate in DMF according to literature. The Fmoc and the 3'-O-acetyl groups were removed by a one-hour treatment with concentrated aqueous ammonia at room temperature and the reaction mixture evaporated and lyophilized. Purification also followed standard procedures by using anion-exchange chromatography on DEAE Sephadex with a linear gradient of triethylammonium bicarbonate (0.1 M–1.0 M). Triphosphate containing fractions, checked by thin layer chromatography on poly-ethyleneimine cellulose plates, were collected, evaporated and lyophilized. Yield by UV-absorbance of the uracil moiety was 68% or 0.48 mmol.

Aglycyl-glycine modified 2'-amino-2'-deoxyuridine-5'-triphosphate was obtained by removing the Fmoc group from 5'-O-(4,4-dimethoxytrityl)-3'-O-acetyl-2'-N(N-9-fluorenylmethyloxycarbonyl-glycyl)-2'-amino-2'-deoxyuridine by a one-hour treatment with a 20% solution of piperidine in DMF at room temperature, evaporation of solvents, two-fold co-evaporation with toluene and subsequent condensation with N-Fmoc-glycine pentafluorophenyl ester. Starting with 1.0 mmol of the 2'-N-glycyl-2'-amino-2'-deoxyuridine derivative and following the procedure described above, 0.72 mmol (72%) of the corresponding 2'-(N-glycyl-glycyl)-2'-amino-2'-deoxyuridine-5'triphosphate was obtained.

Starting with 5'-O-(4,4-dimethoxytrityl)-3'-O-acetyl-2'-amino-2'-deoxyuridine and coupling with N-Fmoc-β-alanine pentafluorophenyl ester, the corresponding 2'-(N-β-alanyl)-2'-amino-2'-deoxyuridine-5'-triphosphate are synthesized. These modified nucleoside triphosphates are incorporated during the Sanger DNA sequencing process in the primer-extension products. The mass difference between the glycine, β-alanine and glycyl-glycine mass-modified nucleosides is, per nucleotide incorporated, 58.06, 72.09 and 115.1 daltons, respectively.

When starting with 5'-O-(4,4-dimethoxytrityl)-3'-amino-2',3'1-dideoxythymidine, the corresponding 3'-(N-glycyl)-3'-amino-, 3'-(-N-glycyl-glycyl)-3'-amino-, and 3'-(N-β-alanyl)-3'-amino-2',3'-dideoxythymidine-5'-triphosphates can be obtained. These mass-modified nucleoside triphosphates serve as a terminating nucleotide unit in the Sanger DNA sequencing reactions providing a mass difference per terminated fragment of 58.06, 72.09 and 115.1 daltons respectively when used in the multiplexing sequencing mode. The mass-differentiated fragments are analyzed by ES and/or MALDI mass spectrometry.

Mass modification of nucleotide triphosphates at C-5 of the heterocyclic base: 0.281 g (1.0 mmol) 5-(3-Aminopropynyl-1)-2'-deoxyuridine was reacted with either 0.927 g (2.0 mmol) N-Fmoc-glycine pentafluorophenylester or 0.955 g (2.0 mmol) N-Fmoc-β-alanine pentafluorophenyl ester in 5 ml dry DMF in the presence of 0.129 g N,N-diisopropylethylamine (174 μl, 1.0 mmol) overnight at room temperature. Solvents were removed by evaporation in vacuo and the condensation products purified by flash chromatography on silica gel (Still et al., J. Org., Chem. 43: 2923–25, 1978). Yields were 476 mg (0.85 mmol; 850%) for the glycine and 436 mg (0.76 mmol; 76%) for the β-alanine derivatives. For the synthesis of the glycyl-glycine derivative, the Fmoc group of 1.0 mmol Fmoc-glycine-deoxyuridine derivative was removed by one-hour treatment with 20% piperidine in DMF at room temperature. Solvents were removed by evaporation in vacuo, the residue was coevaporated twice with toluene and condensed with 0.927 g (2.0 mmol) N-Fmoc-glycine pentafluorophenyl ester and purified as described above. Yield was 445 mg (0.72 mmol; 72%). The glycyl-, glycyl-glycyl- and β-alanyl-2'-deoxyuridine derivatives, N-protected with the Fmoc group were transformed to the 3'-O-acetyl derivatives by tritylation with 4,4-dimethoxytrityl chloride in pyridine and acetylation with acetic anhydride in pyridine in a one-pot reaction and subsequently detritylated by one hour treatment with 80% aqueous acetic acid according to standard procedures. Solvents were removed, the residues dissolved in 100 ml chloroform and extracted twice with 50 ml 10% sodium bicarbonate and once with 50 ml water, dried with sodium sulfate, the solvent evaporated and the residues purified by flash chromatography on silica gel. Yields were 361 mg (0.60 mmol; 71%) for the glycyl-, 351 mg (0.57 mmol; 75%) for the β-alanyl- and 323 mg (0.49 mmol; 68%) for the glycyl-glycyl-3-0'-acetyl-2'-deoxyuridine derivatives, respectively. Phosphorylation at the 5'-OH with $POCl_3$, transformation into the 5'triphosphate by in situ reaction with tetra(tri-n-butylammonium) pyrophosphate in DMF, 3'-de-0-acetylation, cleavage of the Fmoc group, and final purification by anion-exchange chromatography on DEAE-Sephadex was performed and yields according to UV-absorbance of the uracil moiety were 0.41 mmol 5-(3-(N-glycyl)-amidopropynyl-1)-2'-deoxyuridine-5'-triphosphate (84%), 0.43 mmol 5-(3-(N-β-alanyl)-amidopropynyl-1)-2'-deoxyuridine-5'-triphosphate (75%) and 0.38 mmol 5-(3-(N-glycyl-glycyl)-amidopropynyl-1)-2'-deoxyuridine-5'-triphosphate (78%). These mass-modified nucleoside triphosphates were incorporated during the Sanger DNA sequencing primer-extension reactions.

When using 5-(3-aminopropynyl)-2',3'-dideoxyuridine as starting material and following an analogous reaction sequence the corresponding glycyl-, glycyl-glycyl-and β-alanyl-2',3'-dideoxyuridine-5'-triphosphates were obtained in yields of 69%, 63% and 71%, respectively. These mass-modified nucleoside triphosphates serve as chain-terminating nucleotides during the Sanger DNA sequencing reactions. The mass-modified sequencing ladders are analyzed by either ES or MALDI mass spectrometry.

Mass modification of nucleotide triphosphates: 727 mg (1.0 mmol) of $N^6$-(4-tert-butylphenoxyacetyl)-8-glycyl-5'-(4,4-dimethoxytrityl)-2'- deoxyadenosine or 800 mg (1.0 mmol) $N_6$-(4-tert-butylphenoxyacetyl)-8-glycyl-glycyl-5'-(4,4-dimethoxytrityl)-2'-deoxyadenosine prepared according to literature (Köster et al., Tetrahedron 37:362, 1981) were acetylated with acetic anhydride in pyridine at the 3'-OH, detritylated at the 5'-position with 80% acetic acid in a one-pot reaction and transformed into the 5'-triphosphates via phosphorylation with $POCl_3$ and reaction in situ with tetra(tri-n-butylammonium) pyrophosphate. Deprotection of the $N^6$ tert-butylphenoxyacetyl, the 3'-O-acetyl and the O-methyl group at the glycine residues was achieved with concentrated aqueous ammonia for ninety minutes at room temperature. Ammonia was removed by lyophilization and the residue washed with dichloromethane, solvent removed by evaporation in vacuo and the remaining solid material purified by anion-exchange chromatography on DEAE-Sephadex using a linear gradient of triethylammonium bicarbonate from 0.1 to 1.0 M. The nucleoside triphosphate containing fractions (checked by TLC on polyethyleneimine cellulose plates) were combined and lyophilized. Yield of the 8-glycyl-2'-deoxyadenosine-5'-triphosphate (determined by UV-absorbance of the adenine moiety) was 57% (0.57 mmol). The yield for the 8-glycyl-glycyl-2'-deoxyadenosine-5'-triphosphate was 51% (0.51 mmol). These mass-modified nucleoside triphosphates were incorporated during primer-extension in the Sanger DNA sequencing reactions.

When using the corresponding N6-(4-tert-butylphenoxyacetyl)-8-glycyl-or -glycyl-glycyl-5'-O-(4,4-dimethoxytrityl)-2',3'-dideoxyadenosine derivatives as starting materials (for the introduction of the 2',3'-function: Seela et al., Helvetica Chimica Acta 74:1048–58, 1991). Using an analogous reaction sequence, the chain-terminating mass-modified nucleoside triphosphates 8-glycyl- and 8-glycyl-glycyl-2'.3'-dideoxyadenosine-5'-triphosphates were obtained in 53 and 47% yields, respectively. The mass-modified sequencing fragment ladders are analyzed by either ES or MALDI mass spectrometry.

Example 19

Mass Modification of Nucleotides by Alkylation After Sanger Sequencing.

2',3'-Dideoxythymidine-5'-(alpha-S)-triphosphate was prepared according to published procedures (for the alpha-S-triphosphate moiety: Eckstein et al., Biochemistry 15:1685, 1976) and Accounts Chem. Res. 12:204, 1978) and for the 2',3'-dideoxy moiety: Seela et al., Helvetica Chimica Acta 74:1048–58, 1991). Sanger DNA sequencing reactions employing 2'-deoxythymidine-5'-(alpha-S)-triphosphate are performed according to standard protocols. When using 2',3'-dideoxythymidine-5'-(alpha-S)-triphosphates, this is used instead of the unmodified 2',3'-dideoxythymidine-5'-triphosphate in standard Sanger DNA sequencing. The template (2 picomole) and the nucleic acid M13 sequencing primer (4 picomole) are annealed by heating to 65° C. in 100 μl of 10 mM Tris-HCl, pH 7.5, 10 mM $MgCl_2$, 50 mM NaCl, 7 mM dithiothreitol (DTT for 5 minutes and slowly brought to 37° C. during a one hour period. The sequencing reaction mixtures contain, as exemplified for the T-specific termination reaction, in a final volume of 150 μl, 200 μM (final concentration) each of dATP, dCTP, dTTP, 300 μM c7-deaza-dGTP, 5 μM 2',3'-dideoxythymidine-5'-(alpha-S)-triphosphate and 40 units Sequenase. Polymerization is performed for 10 minutes at 37° C., the reaction mixture heated to 70° C. to inactivate the Sequenase, ethanol precipitated and coupled to thiolated Sequelon membrane disks (8 mm diameter). Alkylation is performed by treating the disks with 10 μl of 10 mM solution of either 2-iodoethanol or 3-iodopropanol in NMM (N-methylmorpholine/water/2-propanol, 2/49/49, v/v/v) (three times), washing with 10 μl NMM (three times) and cleaving the alkylated T-terminated primer-extension products off the support by treatment with DTT. Analysis of the mass-modified fragment families is performed with either ES or MALDI mass spectrometry.

Example 20

Mass Modification of an Oligonucleotide.

This method, in addition to mass modification, also modifies the phosphate backbone of the nucleic acids to a non-ionic polar form. Oligonucleotides can be obtained by chemical synthesis or by enzymatic synthesis using DNA polymerases and α-thio nucleoside triphosphates.

This reaction was performed using DMT-TpT as a starting material but the use of an oligonucleotide with an alpha thio group is also appropriate. For thiolation, 45 mg (0.05 mM) of compound 1 (FIG. 15), is dissolved in 0.5 ml acetonitrile and thiolated in a 1.5 ml tube with 1.1-diozo-1-H-benzo[1,2]dithio-3-on (Beaucage reagent). The reaction was allow to proceed for 10 minutes and the produce is concentrated by thin layer chromatography with the solvent system dichloromethane/96% ethanol/pyridine (87%/13%/1%; v/v/v). The thiolated compound 2 (FIG. 15) is deprotected by treatment with a mixture of concentrated aqueous ammonia/acetonitrile (1/1; v/v) at room temperature. This reaction is monitored by thin layer chromatography and the quantitative removal of the beta-cyanoethyl group was accomplished in one hour. This reaction mixture was evaporated in vacuo.

To synthesize the S-(2-amino-2-oxyethyl)thiophosphate triester of DMT-TpT (compound 4), the foam obtained after evaporation of the reaction mixture (compound 3) was dissolved in 0.3 ml acetonitrile/pyridine (5/1; v/v) and a 1.5 molar excess of iodoacetamide added. The reaction was complete in 10 minutes and the precipitated salts were removed by centrifugation. The supernatant is lyophilized, dissolved in 0.3 ml acetonitrile and purified by preparative thin layer chromatography with a solution of dichloromethane/96% ethanol (85%/15%; v/v). Two fractions are obtained which contain one of the two diastereoisomers. The two forms were separated by HPLC.

Example 21
MALDI-MS Analysis of a Mass-Modified Oligonucleotide.

A 17-mer was mass modified at C-5 of one or two deoxyuridine moieties. 5-[13-(2-Methoxyethoxyl)-tridecyne-1-yl]-5'-O-(4,4'-dimethoxytrityl)-2'-deoxyuridine-3'-β-cyanoethyl-N,N-diisopropylphosphoamidite was used to synthesize the modified 17-mers.

The modified 17-mers were:

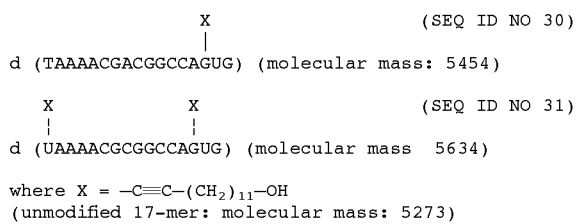

where X = $-C{\equiv}C-(CH_2)_{11}-OH$
(unmodified 17-mer: molecular mass: 5273)

Figure 16:
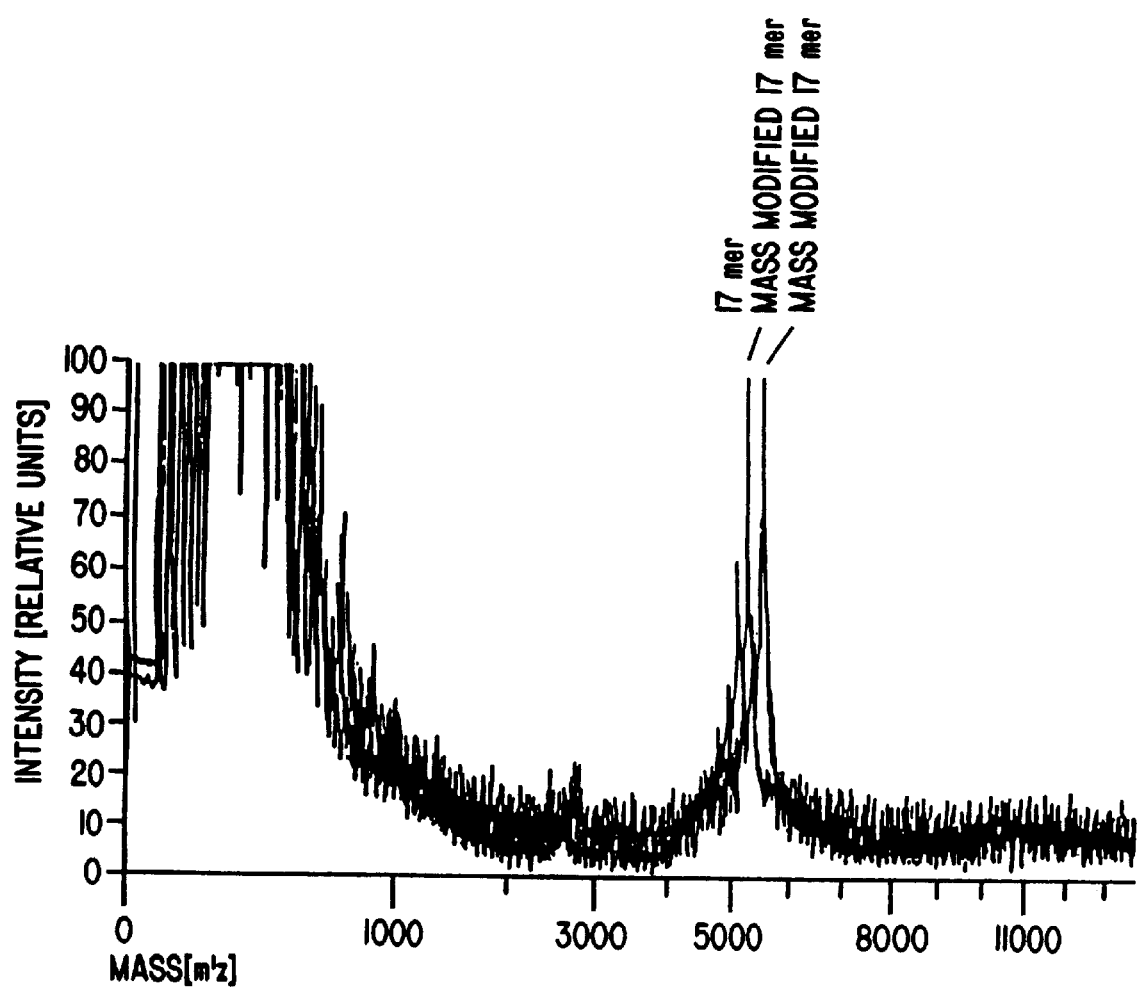
FIG. 16 Mass spectrum of 17-mer target with 0, 1 or 2 mass modified moieties.

The samples were prepared and 500 fmol of each modified 17-mer was analyzed using MALDI-MS. Conditions used were reflectron positive ion mode with an acceleration of 5 kV and post-acceleration of 20 kV. The MALDI-TOF spectra which were generated were superimposed and are shown in FIG. 16. Thus, mass modification provides a distinction detectable by mass spectrometry which can be used to identify base sequence information.

Example 22
Capture and Sequencing of a Double-Stranded Target Nucleic Acid.

Figure 17:
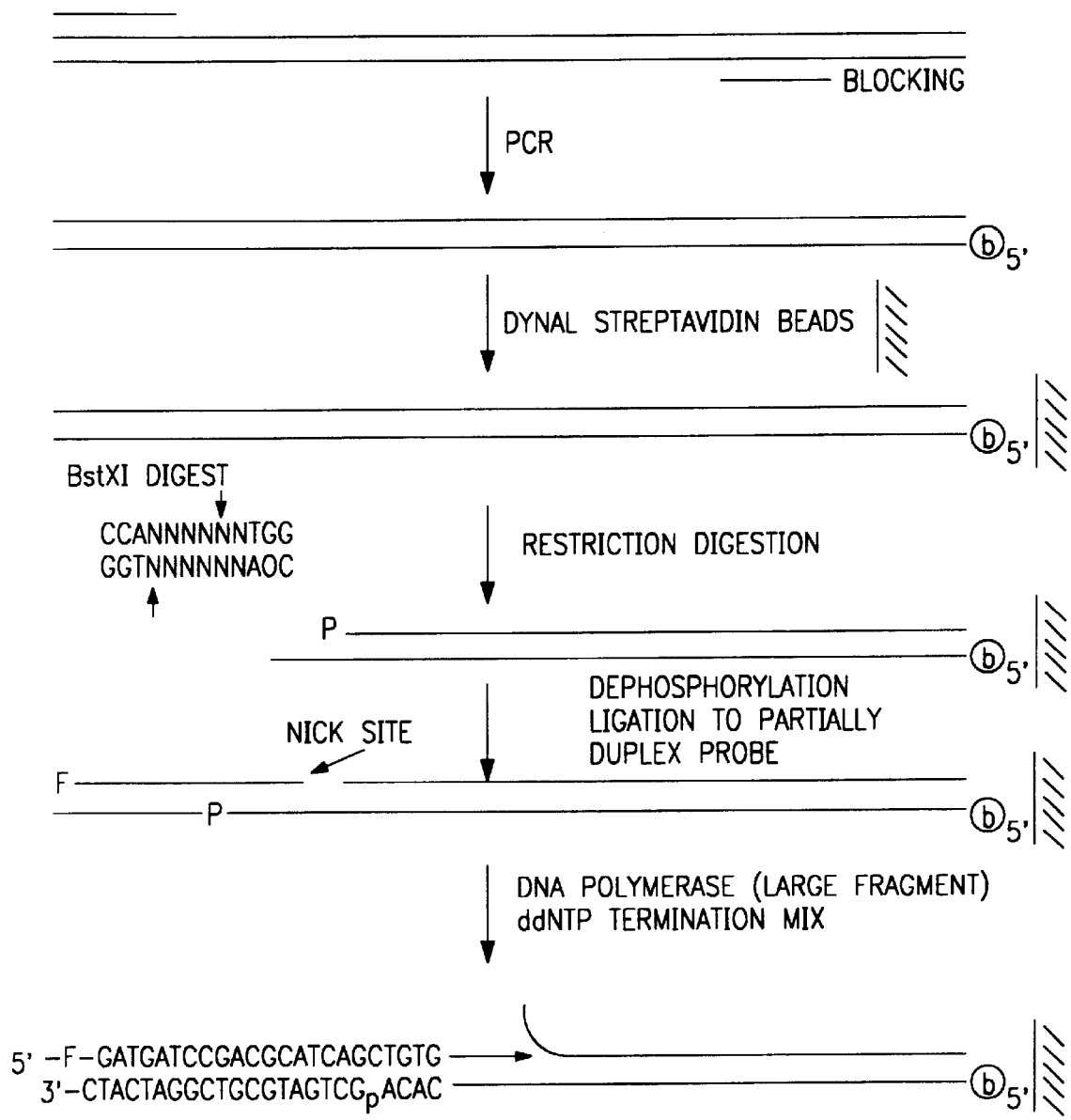
FIG. 17 Schematic of nicked strand displacement sequencing with immobilized template.

In another experiment, a nucleic acid was captured and sequenced by strand-displacement polymerization. This reaction is shown schematically in FIG. 17. Double-stranded DNA target was prepared by PCR and attached to magnetic beads as described in Example 6. EcoR I digested plasmid NB34 was used as the DNA template for amplification. NB34 comprises a PCR™ II plasmid (Invitrogen) with a one kb target human DNA insert. PCR was performed with an 16-nucleotide upstream primer (primer I, 5'-AACAGCTATTACCATG-3'; SEQ ID NO. 32), and a downstream 5'-end biotinylated 18-nucleotide primer (primer II, 5'-biotin-CTGAATTAGTCAGGTTGG-3'; SEQ ID NO. 33). Five hundred basepair PCR products, containing a single BstX I site, were immobilized by attachment to magnetic beads which were resuspended in a total of 300 µl reaction buffer containing 200 units of BstX I restriction endonuclease (Boehringer Mannheim; Indianapolis, Ind.), 50 mM Tris-HCl pH 7.5, 10 mM MgCl$_2$, 100 mM NaCl and 1 mM dithiothreitol. The mixture was incubated at 45° C. for three hours or until digestion was complete which was monitored by agarose gel electrophoresis. After digestion, magnetic beads were washed twice with 300 µl of TE to remove digested and non-immobilized fragments, excess nucleotides and restriction endonuclease.

This immobilized DNA was dephosphorylated by resuspending the beads in 100 µl buffer (500 mM Tris-HCl, pH 9.0, 1 mM MgCl$_2$, 0.1 mM ZnCl$_2$, and 1 mM spermidine) containing five units of calf intestinal alkaline phosphatase (Promega; Madison, Wis.). The reaction was incubation at 37° C. for 15 minutes and at 56° C. for 15 minutes. Five additional units of calf intestinal alkaline phosphatase was added and a second incubation was performed at 37° C. for 15 minutes and at 56° C. for 15 minutes. Beads were washed twice with TE and resuspended in 300 µl of fresh TE containing 1 M NaCl.

Loading of the beads was checked by incubating 10 µl of the beads with 10 µl of formamide at 95° C. for 5 minutes (or by boiling in TE). The mixture was analyzed by 1% agarose gel electrophoresis with ethidium bromide staining. A 10 µl bead aliquot generally contains about 80 ng of immobilized double stranded DNA.

A partial duplex DNA probe containing a four base 3' overhang was used as a sequencing primer and was ligated with BstX I digested DNA fragments which were immobilized on magnetic beads. The partial duplex had a 5'-fluorescein labeled 23 mer (DF25-SF) containing a 5' base paring region and a 4-base 3' single stranded region (which is complementary to the sequence of the 5'-protruding end of the corresponding BstX I digested target DNA as prepared above and a 19 mer (G-CM1) complementary to the base pairing region of the 23 mer. The 19 mer was 5'phosphorylated by the T4 DNA Polymerase and annealed to the corresponding 23 mer in TE at the same molar ratio. Beads, prepared from alkaline phosphatase treatment which have about 10 pmol immobilized DNA template, were ligated to 25 pmol of partially duplex probe in an 100 µl volume containing 200 units of T4 DNA ligase (New England Biolabs; Beverly, Mass.), 50 mM Tris-HCl, pH 7.8, 10 mM MgCl$_2$, 10 mM dithiothreitol, 1 mM ATP, 25 µg/ml bovine serum albumin. Ligation reactions were performed at room temperature for two hours or 4° C. overnight. Beads were washed twice with TE and resuspended in 300 µl of the same buffer.

Sequencing reactions: Thirty µl of beads containing the ligation product were used for each sequencing reaction. Beads were resuspended in a 13 µl volume containing 1.5 µl of 10×Klenow buffer (100 mM Tris-HCl, pH 7.5, 50 mM MgCl$_2$, and 75 mM dithiothreitol) and with or without one µl of single stranded DNA binding protein (SSB, 5 µg/µl; USB; Cleveland, Ohio). Mixtures were incubated on ice for 5 minutes followed with the addition of 5 units of Klenow Fragment (New England Biolabs). The reaction volume was split into four termination mixes, each consisting of 1 µl DMSO and 3 µl of the appropriate termination mixture. Termination mixtures were made in Klenow buffer and comprise the nucleotide concentrations shown below in Table 11.

TABLE 11

| Termination Mix | dATP in mM | dGTP in mM | dCTP in mM | dTTP in mM | ddNTPs |
|---|---|---|---|---|---|
| ddATP mix | 10 | 100 | 100 | 100 | 100 mM ddATP |
| ddGTP mix | 100 | 5 | 100 | 100 | 120 mM ddGTP |
| ddCTP mix | 100 | 100 | 10 | 100 | 100 mM ddCTP |
| ddTTP mix | 100 | 100 | 100 | 5 | 500 mM ddTTP |

Termination mixtures were incubated for 20 minutes at ambient temperature. Two µl of chase solution (0.5 mM of each of four dNTPs in Klenow buffer) were added to each reaction tube and mixtures were incubated for another 15 minutes, again at ambient temperature. Magnetic beads were precipitated with a magnetic particle concentrator (or centrifugation) and the supernatant discarded. Beads were resuspended in a solution containing 10 µl of deionized formamide, 5 mg/ml dextran blue and 0.1% SDS, and heated to 95° C. for 5 minutes, and stored on ice for less than 10 minutes. Samples were analyzed on a DNA sequencing gel and on an ALF DNA sequencer (Pharmacia; Piscataway, N.J.) using a 6% polyacrylamide gel with 7 M urea and 0.6×TBE. Surprisingly, sequencing reactions performed in the presence of single-stranded DNA binding protein showed considerable improvement in resolution. Only 50 bases were resolved from reactions performed without single-stranded DNA binding protein (FIG. 18, bottom panel) whereas 200 bases could be resolved from reactions performed in the presence of single-stranded DNA binding protein (FIG. 18, top panel).

ethanol. Precipitated ΦX174 DNA was washed twice with TE and resuspended in 300 μl of TE containing 1 M NaCl.

Double-stranded probes, comprising biotin (B), fluorescein (F), and infra dye (CYS) labels, were synthesized and anchored to magnetic beads as shown in Table 13.

TABLE 13

| DF27-1 | 5'F-GATGATCCGACGCATCACATCAGTGAC-3' | (SEQ ID NO. 34) |
| | 3'B-CTACTAGGCTGCGTAGTG-p-5' | (SEQ ID NO. 35) |
| DF27-2 | 5'F-GATGATCCGACGCATCACTCCACTGTT-3' | (SEQ ID NO. 36) |
| | 3'B-CTACTAGGCTGCGTAGTG-p-5' | (SEQ ID NO. 37) |
| DF27-3 | 5'F-GATGATCCGACGCATCACGTCAGTGTT-3' | (SEQ ID NO. 38) |
| | 3'B-CTACTAGGCTGCGTAGTG-p-5' | (SEQ ID NO. 39) |
| DF27-4 | 5'F-GATGATCCGACGCATCACTGCAGTGGA-3' | (SEQ ID NO. 40) |
| | 3'B-CTACTAGGCTGCGTAGTG-p-5' | (SEQ ID NO. 41) |
| DF27-5-CY5 | 5'CY5-GATGATCCGACGCATCACGTCACTGAT-3' | (SEQ ID NO. 42) |
| | 3'B-CTACTAGGCTGCGTAGTG-p-5' | (SEQ ID NO. 43) |
| DF27-6-CY5 | 5'CY5-GATGATCCGACGCATCACAACAGTGGA-3' | (SEQ ID NO. 44) |
| | 3'B-CTACTAGGCTGCGTAGTG-p-5' | (SEQ ID NO. 45) |
| DF27-7 | 5'-F-GATGATCCGACGCATCACGTCAGTGGT-3' | (SEQ ID NO. 46) |
| | 3'B-CTACTAGGCTGCGTAGTC-p-5' | (SEQ ID NO. 47) |
| DF27-8 | 5'-F-GATGATCCGACGCATCACAACACTGGT-3' | (SEQ ID NO. 48) |
| | 3'B-CTACTAGGCTGCGTAGTG-p-5' | (SEQ ID NO. 49) |
| DF27-9 | 5'-F-GATCATCCCAGGGATCACAAGAGTGAC-3' | (SEQ ID NO. 50) |
| | 3'B-CTACTAGGGTCCCTAGTG-p-5' | (SEQ ID NO. 51) |
| DF27-10 | 5'-F-GATGATCCGACGCATCACACCACTGAC-3' | (SEQ ID NO. 52) |
| | 3'B-CTACTAGGCTGCGTAGTG-p-5' | (SEQ ID NO. 53) |

Example 23
Specificity of Double-Strand Sequencing by Strand Displacement.

Figure 19:
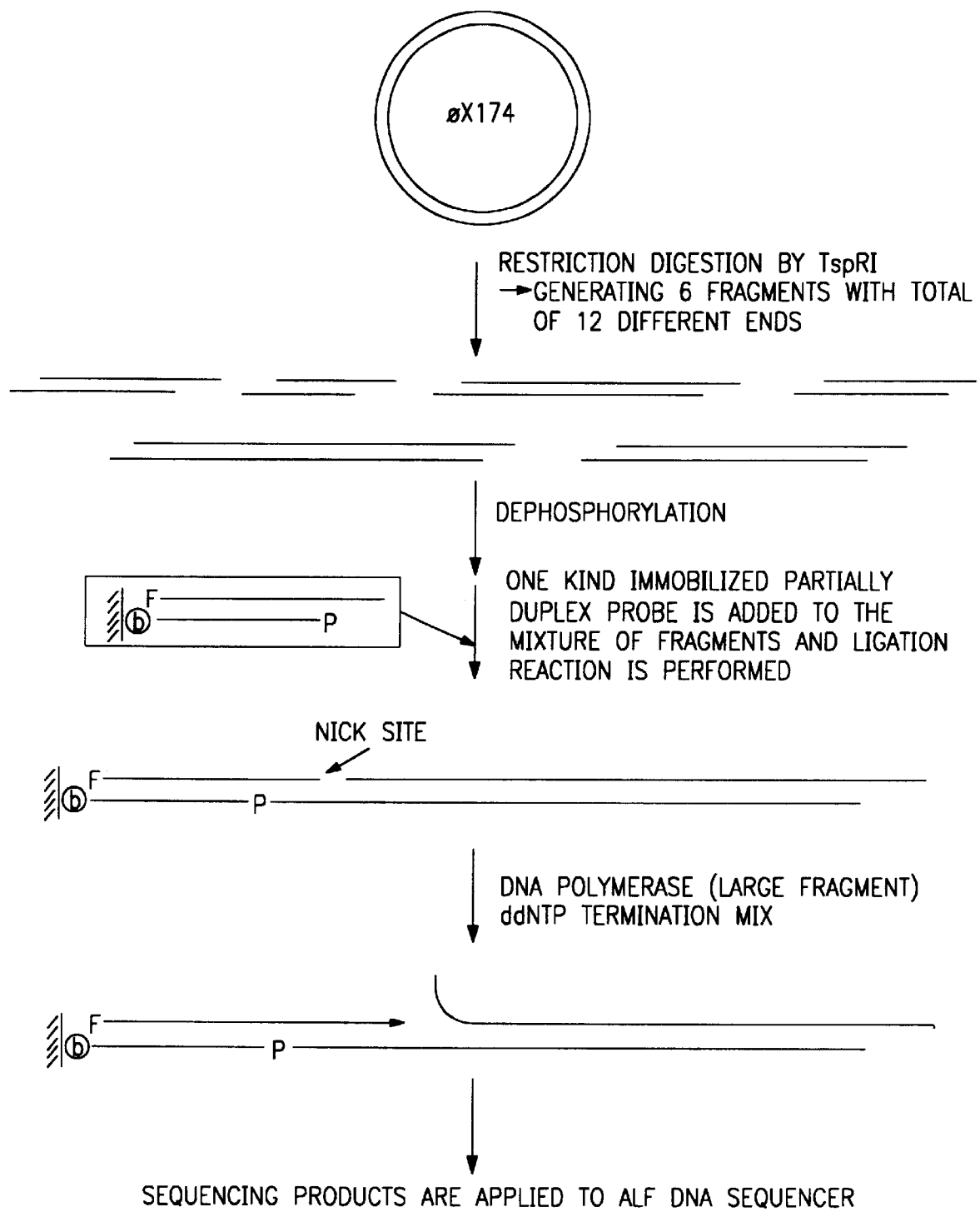
FIG. 19 Schematic of nicked strand displacement sequencing with immobilized probe.

Another experiment was performed to determine the specificity and applicability of the nick translation strand displacement method of sequencing double-stranded nucleic acids. A schematic of the experimental design is shown in FIG. 19. Briefly, a double-stranded target DNA was prepared by digesting double-stranded ΦX174 phage DNA with TspR I restriction endonuclease. TspR I has a recognition site of NNCAGTGNN and cleaves ΦX174 into 12 fragments each with distinctive 3' protruding ends. Possible ends are shown in Table 12.

TABLE 12

| 1 | 5'-AACACTGAC-3' | 7 | 5'-GTCAGTGTT-3' |
| 2 | 5'-AACAGTGGA-3' | 8 | 5'-GTCAGTGGT-3' |
| 1 | 5'-AACACTGAC-3' | 7 | 5'-GTCAGTGTT-3' |
| 3 | 5'-ACCACTGAC-3' | 9 | 5'-GTCACTGAT-3' |
| 4 | 5'-AACACTGGT-3' | 10 | 5'-TCCACTGTT-3' |
| 5 | 5'-ATCAGTGAC-3' | 11 | 5'-TGCAGTGGA-3' |
| 6 | 5'-ACCAGTGTT-3' | 12 | 5'-TCCACTGCA-3' |

ΦX174 DNA (5 pmol) was dephosphorylated using calf intestinal alkaline phosphatase. Briefly, ΦX174 DNA was resuspended in 100 μl buffer (500 mM Tris-HCl, pH 9.0, 1 mM MgCl$_2$, 0.1 mM ZnCl$_2$, and 1 mM spermidine) containing 5 units of calf intestinal alkaline phosphatase (Promega; Madison, Wis.). The reaction was incubation at 37° C. for 15 minutes and at 56° C. for 15 minutes. Five additional units of calf intestinal alkaline phosphatase was added and a second incubation was performed at 37° C. for 15 minutes and at 56° C. for 15 minutes. DNA in the samples was extracted once with phenol, once with phenol/chloroform, and once with chloroform, after which nucleic acid was precipitated in 0.3 M sodium acetate/2.5 volumes Beads with about 25 pmol of immobilized primer were ligated to 3 pmol of digested TspR I ΦX174 DNA in 50 μl containing 400 units of T4 DNA ligase (New England Biolabs; Beverly, Mass.), 50 mM Tris-HCl, pH 7.8, 10 mM MgCl$_2$, 10 mM dithiothreitol, 1 mM ATP and 25 μg/ml bovine serum albumin. Ligation reactions were performed at 37° C. for 30 minutes, at 50° C. to 55° C. for one hour (thermal ligase), at room temperature for 2 hours or at 4° C. for overnight. After ligation, beads were washed twice with TE and resuspended in 300 μl of the same buffer.

Sequencing reactions: For each sequencing reaction, 30 μl of beads containing the ligation product was used. Beads were resuspended in a 13 μl volume containing 1.5 μl of 10×Klenow buffer (100 mM Tris-HCl, pH 7.5, 50 mM MgCl$_2$ and 75 mM dithiothreitol), and with or without 1 μl of single-stranded DNA binding protein (SSB, 5 μg/μl; USB; Cleveland, Ohio). Reaction mixtures were incubated on ice for 5 minutes, followed by the addition of 5 units of Klenow Fragment (New England Biolabs). The reaction volume was split into four termination mixes, each consisting of 1 μl DMSO plus 3 μl of the appropriate termination mix. Termination mixes were made in Klenow buffer and comprise the nucleotides concentrations shown in Table 11.

Termination mixtures were incubated for 20 minutes at ambient temperature. Two μl of a chase solution containing 0.5 mM of each of the four dNTPs in Klenow buffer, was added to each reaction tube and mixtures were incubated for another 15 minutes at ambient temperature. Beads were precipitated by magnetic particle concentrator or centrifugation and the supernatant discarded. Precipitated beads were resuspended in TE or in a solution containing 10 μl deionized formamide, 5 mg/ml dextran blue and 0.1% SDS, and heated to 95° C. for 5 minutes. Mixtures were stored on ice for less than 10 minutes and analyzed by a DNA sequencing gel and on an ALF DNA sequencer (Pharmacia; Piscataway, N.J.) using a 6% polyacrylamide gel with 7 M urea and 0.6×TBE.

One double stranded primer was used for each reaction and the results achieved using primers DF27-1, DF27-2, DF27-4, DF27-5-CY5 and DF27-6-CY5, are shown in FIGS. 20, 21, 22, 23 and 24, respectively. Each primer was capable of generating sequencing information of up to 200 basepairs without significant interference from the 11 fragments with non-complementary ends.

Other embodiments and uses of the invention will be apparent to those skilled in the art from consideration of the specification and practice of the invention disclosed herein. All U.S. Patents and other references noted herein are specifically incorporated by reference. The specification and examples should be considered exemplary only with the true scope and spirit of the invention indicated by the following claims.

We claim:

1. A method for sequencing a target nucleic acid comprising the steps of:
   a) providing a set of partially single-stranded nucleic acid fragments, wherein each fragment contains a sequence that corresponds to a sequence of the target;
   b) hybridizing the single-stranded portions of the fragments to single-stranded portions of a set of partially double-stranded nucleic acid probes to form a set of complexes, and for each complex;
      i) ligating a single strand of the fragment to an adjacent single strand of the probe; and
      ii) extending the unligated strand of the complex by strand-displacement polymerization using the ligated strand as a template; and
   c) determining the sequence of the target.

2. The method of claim 1 wherein the target is between about 10 to about 1,000 nucleotides in length.

3. The method of claim 1 wherein the set of partially single-stranded fragments is a product of a polymerase chain reaction or an endonuclease digestion.

4. The method of claim 1 wherein each set of nucleic acids comprises greater than about $10^4$ different members.

5. The method of claim 1 wherein the single-stranded portion of each probe contains a variable sequence.

6. The method of claim 1 wherein the fragments or the probes are attached to a solid support.

7. The method of claim 1 wherein the nucleic acids are DNA, RNA, PNA or modifications or combinations thereof.

8. The method of claim 1 wherein the fragments or the probes are dephosphorylated by treatment with a phosphatase prior to hybridization.

9. The method of claim 1 wherein each probe is between about 10 to about 50 nucleotides in length.

10. The method of claim 1 wherein the double-stranded regions of the probes contain the same sequence for each probe of the set.

11. The method of claim 1 wherein polymerization incorporates mass-modifying nucleotides into the extended strand.

12. The method of claim 1 wherein polymerization incorporates dNTPs and ddNTPs into the extended strand.

13. The method of claim 12 wherein a plurality of extended strands comprise a nested set.

14. The method of claim 1 wherein a plurality of extended strands comprise about 0.1 femtomole to about 1.0 nanomole of nucleic acid.

15. The method of claim 1 wherein the sequence is determined by polyacrylamide electrophoresis, capillary electrophoresis or mass spectrometry.

16. A method for sequencing a target nucleic acid comprising the steps of:
   a) providing a set of partially single-stranded nucleic acid fragments, wherein each fragment contains a sequence that corresponds to a sequence of the target;
   b) hybridizing the single-stranded portions of the fragments to single-stranded portions of a set of partially double-stranded nucleic acid probes to form a set of complexes, and for each complex;
      i) ligating a single strand of the fragment to an adjacent single strand of the probe; and
      ii) extending the unligated strand of the complex by strand-displacement polymerization using the ligated strand as a template and mass-modifying the extended strand;
   c) determining the molecular weights of the extended strands; and
   d) determining the sequence of the target from the molecular weights of the extended strands.

17. The method of claim 16 wherein the extended strand contains mass-modifying functionalities.

18. The method of claim 17 wherein at least one mass-modifying functionality is coupled to a heterocyclic base.

19. The method of claim 17 wherein at least one mass-modifying functionality is coupled to a sugar moiety.

20. The method of claim 17 wherein at least one mass-modifying functionality is coupled to a phosphate group.

21. The method of claim 17 wherein the mass-modifying functionality is a chemical moiety that does not interfere with hydrogen bonding for base-pair formation.

22. The method of claim 17 wherein the mass-modifying functionality is coupled to a purine at position C2, N3, N7 or C8, or a deazapurine at position N7 or N9.

23. The method of claim 17 wherein the mass-modifying functionality is coupled to a pyrimidine at position C5 or C6.

24. The method of claim 17, wherein;
   the mass-modifying functionality is selected from the group consisting of deuterium, F, Cl, Br, I, $SiR_3$, $Si(CH_3)_3$, $Si(CH_3)_2(C_2H_5)$, $Si(CH_3)(C_2H_5)_2$, $Si(C_2H_5)_3$, $(CH_2)_nCH_3$, $(CH_2)_nNR_2$, $CH_2CONR_2$, $(CH_2)_nOH$, $CH_2F$, $CHF_2$, and $CF_3$;
   n is an integer; and
   R is selected from the group consisting of —H, deuterium and alkyls, alkoxys and aryls of 1–6 carbon atoms, polyoxymethylene, monoalkylated polyoxymethylene, polyethylene imine, polyamide, polyester, alkylated silyl, heterooligo/polyaminoacid and polyethylene glycol.

25. The method of claim 17, wherein;
   the mass-modifying functionality is —$N_3$ or —XR:
   X is selected from the group consisting of —O—, —NH—, —NR—, —S—, —NHC(S)—, —OCO$(CH_2)_n$COO—, —NHCO$(CH_2)_n$COO—, —OSO$_2$O—, —OCO$(CH_2)_n$—, —NHC(S)NH—, —OCO$(CH_2)_n$S—, —OCO$(CH_2)$S—, —NC$_4$O$_2$H$_2$S—, —OPO(O-alkyl)—, and OP(O-alkyl)—;
   n is an integer from 1 to 20; and
   R is selected from the group consisting of —H, deuterium and alkyls, alkoxys and aryls of 1–6 carbon atoms, polyoxymethylene, monoalkylated polyoxymethylene, polyethylene imine, polyamide, polyester, alkylated silyl, heterooligo/polyaminoacid and polyethylene glycol.

26. The method of claim 16 wherein the extended strand is mass-modified by thiolation.

27. The method of claim 26 wherein thiolation is performed by treating said extended strand with a Beaucage reagent.

28. The method of claim 16 wherein the extended strand is mass-modified by alkylation.

29. The method of claim 28 wherein alklyation is performed by treating said extended strand with iodoacetamide.

30. The method of claim 16 further comprising the step of removing alkali cations from said mass-modified extended strand.

31. The method of claim 30 wherein alkali cations are removed by ion exchange.

32. A method for sequencing a target nucleic acid comprising the steps of:
   a) providing a set of partially single-stranded nucleic acid fragments wherein each fragment contains a sequence that corresponds to a sequence of the target;
   b) hybridizing the single-stranded portions of the fragments to single-stranded portions of a set of partially double-stranded nucleic acid probes to form a set of complexes wherein each probe contains a variable sequence within the single-stranded region, and for each complex;
      i) ligating a single strand of the fragment to an adjacent single strand of the probe; and
      ii) extending the unligated strand of the complex by strand-displacement polymerization using the ligated strand as a template;
   c) determining the molecular weights of the extended strands; and
   d) determining the sequence of the target from the molecular weights of the extended strands.

33. The method of claim 32 wherein one set of nucleic acids is attached to a solid support.

34. The method of claim 33 wherein the solid support is selected from the group consisting of plates, beads, microbeads, whiskers, combs, hybridization chips, membranes, single crystals, ceramics and self-assembling monolayers.

35. The method of claim 33 wherein the probes are conjugated with biotin or a biotin derivative and the solid support is conjugated with avidin, streptavidin or a derivative thereof.

36. The method of claim 33 further comprising a spacer between the array and the solid support.

37. The method of claim 36 wherein the spacer is selected from the group consisting of oligopeptides, oligonucleotides, oligopolyamides, oligoethyleneglycerol, oligoacrylamides, alkyl chains of between about 6 to about 20 carbon atoms, and combinations thereof.

38. The method of claim 33 wherein the attachment is a cleavable attachment.

39. The method of claim 38 wherein the cleavable attachment is cleavable by heat, an enzyme, a chemical agent or electromagnetic radiation.

40. The method of claim 16, wherein the molecular weights of the extended strands are determined by mass spectrometry.

41. The method of claim 40, wherein the mass spectrometry includes fast atom bombardment, plasma desorption, matrix-assisted laser desorption/ionization, electrospray, photochemical release, electrical release, droplet release, resonance ionization or a combination thereof.

42. The method of claim 40, wherein the mass spectrometry format includes time of flight with reflection, time of flight without reflection, electrospray, Fourier transform, ion trap, resonance ionization, ion cyclotron resonance or a combination thereof.

43. The method of claim 40, wherein the molecular weights of two or more extended strands are determined simultaneously.

44. The method of claim 32, wherein the molecular weights of the extended strands are determined by mass spectrometry.

45. The method of claim 44, wherein the mass spectrometry includes fast atom bombardment, plasma desorption, matrix-assisted laser desorption/ionization, electrospray, photochemical release, electrical release, droplet release, resonance ionization or a combination thereof.

46. The method of claim 44, wherein the mass spectrometry includes time of flight with reflection, time of flight without reflection, electrospray, Fourier transform, ion trap, resonance ionization, ion cyclotron resonance or a combination thereof.

47. The method of claim 44, wherein the molecular weights of two or more extended strands are determined simultaneously.

* * * * *

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Title page,
Item [63], Related U.S. Application Data,

Please replace "Continuation-in-part of application number 08/420,009, filed on April 11, 1995, now abandoned, which is a continuation-in-part of application number 08/110,691, filed on August 23, 1993, now Pat. Num. 5,795,714, which is a continuation-in-part of application number 07/972,012, filed on November 6, 1992; now abandoned and a continuation-in-part of application number 08/419,994, filed on April 11, 1995, now abandoned, which is a continuation-in-part of application number 08/001,323, filed on January 7, 1993, now abandoned." with —Continuation-in-part of application number 08/420,009, filed on April 11, 1995, now abandoned, which is a continuation-in-part of application number 08/110,691, filed on August 23, 1993, now Pat. Num. 5,795,714, which is a continuation-in-part of application number 07/972,012, filed on November 6, 1992; now abandoned.—

Item [57], ABSTRACT,
Line 8, please replace "These probe comprise a single-stranded portion" with
-- These probes comprise a single-stranded portion --
Item [74], *Attorney, Agent, or Firm*: please replace "Paula Schaeneck" with
-- Paula Schoeneck --

UNITED STATES PATENT AND TRADEMARK OFFICE
CERTIFICATE OF CORRECTION

PATENT NO. : 6,436,635 B1 Page 2 of 34
DATED : August 20, 2002
INVENTOR(S) : Fu et al.

It is certified that error appears in the above-identified patent and that said Letters Patent is hereby corrected as shown below:

Item [56], References Cited, U.S. PATENT DOCUMENTS, please add the following references:

| | | |
|---|---|---|
| —3807235 | 04/30/74 | Lefkovitz *et al.* |
| 4139346 | 02/13/79 | Rabbani |
| 4214159 | 01/22/80 | Hillenkamp *et al.* |
| 4461328 | 07/24/84 | Kenney |
| 4473452 | 09/25/84 | Cantor *et al.* |
| 4683194 | 07/28/87 | Saiki *et al.* |
| 4683195 | 07/28/87 | Mullis et al. |
| 4725677 | 02/16/88 | Köster *et al.* |
| 4729947 | 03/08/88 | Middendorf *et al.* |
| 4778993 | 10/18/88 | Waugh |
| 4779467 | 10/25/88 | Rainin *et al.* |
| 4797355 | 01/10/89 | Stabinsky |
| 4806546 | 02/21/89 | Carrico *et al.* |
| 4808520 | 02/28/89 | Dattagupta *et al.* |
| 4882127 | 11/21/89 | Rosenthal *et al.* |
| 4920264 | 04/24/90 | Becker |
| 4948882 | 08/14/90 | Ruth |
| 4952518 | 08/28/90 | Johnson *et al.* |
| 4988617 | 01/29/91 | Landegren et al |
| 4994373 | 02/19/91 | Stavrianopoulos *et al.* |
| 4997928 | 03/05/91 | Hobbs, Jr. |
| 5000921 | 03/19/91 | Hanaway *et al.* |
| 5045694 | 09/03/91 | Beavis *et al.* |
| 5062935 | 11/05/91 | Schlag *et al.* |
| 5077210 | 12/31/91 | Eigler *et al* |
| 5082935 | 01/21/92 | Cruickshank |
| 5108703 | 04/28/92 | Pfost *et al.* |
| 5118605 | 06/02/92 | Urdea |
| 5118937 | 06/02/92 | Hillenkamp *et al.* |
| 5171989 | 12/15/92 | Williams *et al.* |
| 5185243 | 02/09/93 | Ullman *et al.* |
| 5202561 | 04/13/93 | Giessmann *et al.* |
| 5237016 | 08/17/93 | Ghosh *et al.* |
| 5242974 | 09/07/93 | Holmes |
| 5262128 | 11/16/93 | Leighton *et al.* |
| 5306619 | 04/26/94 | Edwards *et al.* |
| 5373156 | 12/13/94 | Franzen |
| 5376788 | 12/27/94 | Standing *et al.* |

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

U.S. PATENT DOCUMENTS cont'd,

| | | |
|---|---|---|
| 5380833 | 01/10/95 | Urdea *et al.* |
| 5381008 | 01/10/95 | Tanner *et al.* |
| 5382793 | 01/17/95 | Weinberger *et al.* |
| 5412087 | 05/02/95 | McGall *et al.* |
| 5424186 | 06/13/95 | Fodor *et al.* |
| 5430136 | 07/04/95 | Urdea *et al.* |
| 5436327 | 07/25/95 | Southern *et al.* |
| 5474895 | 12/12/95 | Ishii *et al.* |
| 5478893 | 12/26/95 | Ghosh *et al.* |
| 5482836 | 01/09/96 | Cantor *et al.* |
| 5484701 | 01/16/96 | Cocuzza *et al.* |
| 5503980 | 04/02/96 | Cantor |
| 5503980 | 04/02/96 | Cantor |
| 5506348 | 04/09/96 | Pieles |
| 5510613 | 04/23/96 | Reilly *et al.* |
| 5512295 | 04/30/96 | Kornberg *et al.* |
| 5512439 | 04/30/96 | Hornes *et al.* |
| 5514548 | 05/07/96 | Krebber *et al.* |
| 5527681 | 06/18/96 | Holmes |
| 5541313 | 07/30/96 | Ruth |
| 5545539 | 08/13/96 | Miller |
| 5547835 | 08/20/96 | Köster |
| 5547835 | 08/20/96 | Koster |
| 5547839 | 08/20/96 | Dower |
| 5578444 | 11/26/96 | Edwards *et al.* |
| 5580733 | 12/03/96 | Levis *et al.* |
| 5605662 | 02/25/97 | Heller |
| 5605798 | 02/25/97 | Köster *et al.* |
| 5622824 | 04/22/97 | Köster |
| 5624711 | 04/29/97 | Sundberg *et al.* |
| 5625184 | 04/29/97 | Vestal *et al.* |
| 5627369 | 05/06/97 | Vestal *et al.* |
| 5631134 | 05/20/97 | Cantor |
| 5631134 | 05/20/97 | Cantor |
| 5641959 | 06/24/97 | Holle *et al.* |

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

U.S. PATENT DOCUMENTS cont'd,

| | | |
|---|---|---|
| 5643722 | 07/01/97 | Rothschild *et al.* |
| 5650274 | 07/1997 | Kambara *et al.* |
| 5654545 | 08/05/97 | Holle *et al.* |
| 5663242 | 09/02/92 | Ghosh *et al.* |
| 5670381 | 09/23/97 | Jou *et al.* |
| 5677195 | 10/14/97 | Winkler *et al.* |
| 5691141 | 11/25/96 | Koster |
| 5691141 | 11/25/97 | Köster |
| 5693463 | 12/02/97 | Edwards *et al.* |
| 5700642 | 12/23/97 | Monforte |
| 5716780 | 02/10/98 | Edwards *et al.* |
| 5726014 | 03/10/98 | Edwards *et al.* |
| 5738990 | 04/14/98 | Edwards *et al.* |
| 5742049 | 04/21/98 | Holle *et al.* |
| 5744131 | 04/28/98 | Edwards *et al.* |
| 5746373 | 05/05/98 | Sanada |
| 5753439 | 05/19/98 | Smith *et al.* |
| 5760393 | 06/02/98 | Vestal *et al.* |
| 5770456 | 06/23/98 | Holmes |
| 5777324 | 07/07/98 | Hillenkamp |
| 5777325 | 07/07/98 | Weinberger *et al.* |
| 5795714 | 08/18/98 | Cantor *et al.* |
| 5795714 | 08/18/98 | Cantor *et al.* |
| 5800992 | 09/01/98 | Fodor *et al.* |
| 5807522 | 09/15/98 | Brown *et al.* |
| 5821063 | 10/13/98 | Patterson *et al.* |
| 5830655 | 11/03/98 | Monforte *et al.* |
| 5864137 | 01/26/99 | Becker *et al.* |
| 5869240 | 02/09/99 | Patterson |
| 5869242 | 02/09/99 | Kamb |
| 5871928 | 02/16/99 | Fodor *et al.* |
| 5885775 | 03/23/99 | Haff et al |
| 5894063 | 04/13/99 | Hutchens *et al.* |
| 5900481 | 05/04/99 | Lough *et al.* |
| 5902723 | 05/11/99 | Dower *et al.* |
| 5925525 | 07/20/99 | Fodor *et al.*— |

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

FOREIGN PATENT DOCUMENTS, please add the following references:

| | | |
|---|---|---|
| —0360676 | 03/28/90 | EP |
| 0360677 | 09/18/89 | EP |
| 0371437 | 06/06/90 | EP |
| 0392546 | 12/04/90 | EP |
| 0396116 | 11/07/90 | EP |
| 0412883 | 02/13/91 | EP A1 |
| 0455905 | 11/13/91 | EP |
| 0456304 | 11/13/91 | EP A1 |
| 0630972 | 12/28/94 | EP |
| 0701001 | 03/13/96 | EP A2 |
| 2215399 | 08/28/90 | JP |
| 2597260 | 10/16/87 | FR A1 |
| 3221681 | 12/08/83 | DE A1 |
| 3930312 | 04/26/90 | DE |
| 3930312 | 04/26/90 | DE |
| 4011991 | 10/18/90 | DE |
| 4011991 | 10/18/90 | DE |
| 6294796 | 10/21/94 | JP |
| 63230086 | 09/26/88 | JP |
| 8290377 | 11/05/96 | JP |
| 8903432 | 04/20/89 | PCT |
| 8909282 | 10/05/89 | PCT |
| 8909406 | 10/05/89 | PCT |
| 8912694 | 12/28/89 | PCT |
| 9001564 | 02/22/90 | PCT |
| 9003382 | 04/05/90 | PCT |
| 9007582 | 07/12/90 | PCT |
| 9014148 | 11/29/90 | PCT |
| 9014148 | 11/29/90 | PCT |
| 9015883 | 12/27/90 | PCT |
| 9105060 | 04/18/91 | PCT |
| 9106678 | 05/16/91 | PCT |
| 9111533 | 08/08/91 | PCT |
| 9202635 | 02/20/92 | PCT |
| 9203575 | 03/05/92 | PCT |
| 9207879 | 05/14/92 | PCT |
| 9210092 | 06/25/92 | PCT |
| 9210588 | 06/25/92 | PCT |
| 9213629 | 08/20/92 | PCT |
| 9306925 | 04/15/93 | PCT |
| 9309668 | 05/27/93 | PCT |
| 9400193 | 06/01/94 | PCT |
| 9411529 | 05/26/94 | PCT |
| 9411530 | 05/26/94 | PCT |
| 9411735 | 05/26/94 | PCT |
| 9416101 | 07/21/94 | PCT |
| 9416101 | 07/21/94 | PCT |
| 9504524 | 02/16/95 | PCT |
| 9507361 | 03/16/95 | PCT |
| 9514108 | 05/26/95 | PCT |
| 9530773 | 11/16/95 | PCT |
| 9602836 | 02/01/96 | PCT |
| 9619587 | 06/27/96 | PCT |
| 9629431 | 09/26/96 | PCT |
| 9629431 | 09/26/96 | PCT |
| 9632504 | 10/17/96 | PCT |
| 9636731 | 11/21/96 | PCT |
| 9636986 | 11/21/96 | PCT |
| 9636987 | 11/21/96 | PCT |
| 9708306 | 03/06/97 | PCT |

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

FOREIGN PATENT DOCUMENTS cont'd,

| | | |
|---|---|---|
| 9716699 | 05/09/97 | PCT |
| 9733000 | 09/12/97 | PCT |
| 9737041 | 10/09/97 | PCT |
| 9737041 | 10/09/97 | PCT |
| 9742348 | 11/13/97 | PCT |
| 9743617 | 11/20/97 | PCT |
| 9812355 | 03/26/98 | PCT |
| 9820019 | 05/14/98 | PCT |
| 9820019 | 05/14/98 | PCT |
| 9820020 | 05/14/98 | PCT |
| 9820020 | 05/14/98 | PCT |
| 9820166 | 05/14/98 | PCT |
| 9820166 | 05/14/98 | PCT |
| 9854751 | 12/03/98 | PCT |
| 9931278 | 06/24/99 | PCT— |

OTHER PUBLICATIONS, please add the following references:

—Agrawal *et al.*, Efficient methods for attaching non-radioactive labels to the 5' ends of synthetic oligodeoxyribonucleotides, Nucleic Acids Res. 14:6227-6245 (1986)

Alderton *et al.*, Magnetic bead purification of M13 DNA sequencing templates, Anal. Biochem. 201:166-169 (1992)

Andersen, *et al.*, Electrospray ionization and matrix assisted laser desorption/ionization mass spectrometry: Powerful analytical tools in recombinant protein chemistry, Nature Biotech. 14:449-457 (1996).

Ardrey, "Electrospray mass spectrometry", Spectroscopy Europe 4(4):10-18 (1992).

Argarana *et al.*, Molecular cloning and nucleotide sequence of the streptavidin gene, *Nuc Acids Res*, 14(4):1871-1882 (1986)

Arlinghause *et al.*, Applications of resonance ionization spectroscopy for semiconductor, environmental dn biomedical analysis, and for DNA sequencing, *SPIE* 1435:26-35 (1991)

UNITED STATES PATENT AND TRADEMARK OFFICE
CERTIFICATE OF CORRECTION

PATENT NO.    : 6,436,635 B1
DATED         : August 20, 2002
INVENTOR(S)   : Fu et al.

It is certified that error appears in the above-identified patent and that said Letters Patent is hereby corrected as shown below:

OTHER PUBLICATIONS cont'd,

Arrand, Preparation of nucleic acid probes, Nucleic Acid Hybridisation, A Practical Approach, Chapter 2, pp. 17-44 (1985)

Arshady, Reza; Review: Beaded Polymer Supports and Gels, I. Manufacturing Techniques; Journal of Chromatography, 586 (1991); pp.181-197

Arshady, Reza; Review: Beaded Polymer Supports and Gels, II. Physico-Chemical Criteria and Functionalization; Journal of Chromatography, 586 (1991); pp.199-219

Axelrod et al., Transcription from bacteriophage T7 and SP6 RNA polymerase promoters in the presence of 3'-deoxyribonucleoside 5'-thiposphate chain terminators, *Biochemistry* 24:5716-5723 (1985)

Baines, DNA sequencing by mass spectrometry. Outline of a potential future application, *Chimicaoggi* pp. 13-16 (1991)

Bains, Setting a sequence to sequence a sequence, *Bio/Tech* 10:757-758 (1992)

Bains, W., Hybridization methods for DNA sequencing, Genomics 11:294-301 (1991)

Bannwarth, Solid-phase synthesis of oligodeoxynucleotides containing phosphoramidate internucleotide linkages and their specific chemical cleavage, Helvetica Chimica Acta 71:1517-1527 (1988)

Barrell B., "DNA sequencing: present limitations and prospects for the future", FASEB Journal 5:40-45 (1991).

Batista-Viera et al., A new method for reversible immobilization of thiol biomolecules bsed on solid-phase bound thiolsulfonate groups, App. Biochem and Biotech,31:175-195 (1991)

Beck, Applications of dioxetane chemiluminescent probes to molecular biology, *Analytical Chemistry* 62:2258-2270 (1990)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Beck et al., "Chemiluminescent detection of DNA: Application of DNA sequencing and hybridization", Nucleic Acids Res. 17(13):5115-5123 (1989)

Berkenkamp et al., Infrared MALDI mass spectrometry of large nucleic acids, Science 281:260-2 (1998).

Billings PR et al., New techniques for physical mapping of the human genome, FASEB J 5(1):28-34 (1991)

Braun et al., Improved Analysis of Microsatellites Using Mass Spectrometry, Genomics 46:18-23(1997).

Braun et al., Detecting CFTR gene mutations by using primer oligo base extension and mass spectrometry, Clinical Chemistry 43:1151-1158 (1997).

Brennan et al., New methods to sequence DNA by mass spectrometry, SPIE, vol. 1206, New Technol. Cytom. Mol. Biol. pp. 60-77 (1990)

Broude et al., Enhanced DNA sequencing by hybridization, Proc. Natl. Acad. Sci. USA 91:3072-3076 (1994).

Brown, et al., "A single-bead decode strategy using electrospray ionization mass spectrometry and a new photolabile linker: 3-amino-3-(2-nitrophenyl) propionic acid", Mol. Diversity 1:4-12(1995).

Brumbaugh, Continuous, on-line DNA sequencing using oligodeoxynucleotide primers with multiple fluorophores, Proc. Natl. Acad. Sci USA 85:5610-5614 (1988)

Caldwell et al., Mid-infrared matrix assisted laser desorption ionization with a water/glycero matrix, Applied Surface Science 127-129:242-247 (1998)

Cantor CR et al., The future of DNA sequencing: methods and applications, In Mass Spectrometry in the Biological Sciences, A.L. Burlingame and S.A. Carr eds., Totawa, NJ: Humana Press, 519-533 (1996)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Cantor *et al.*, Parallel processing in DNA analysis, In Proceedings of 2nd International Workshop on Parallel Algorithms for Irregularly Structured Problems, Lyon, France: Lecture Notes in Computer Science 980, eds. A. Ferreira, J. Rolim, Springer Verag, Berlin, New York 171-185 (1995)

Cantor CR *et al.*, Pulsed-field gel electrophoresis of very large DNA molecules, In Annual Review of Biophysics and Biophysical Chemistry, ed. D.N. Engelman, C.R. Cantor, and T.D. Pollard, Annual Reviews Inc., Palo Alto, p. 287-304 (1988)

Cantor CR and Fields CA, Meeting report: Genome Sequencing Conference III: Evolution and Progress, Genomics 12:419-420 (1992)

Cantor CR *et al.*, DNA sequencing after the human genome project, Nucleosides and Nucleotides 16:591-598 91997)

Cantor CR, Budgeting the genome, Trends in Biotech 10:6-7 (1992)

Cantor CR *et al.*, Lighting up hybridization, Nature Biotech. 14:264

Cantor CR *et al.*, Massive attack on high-throughput biology, Nat. Genet. 20:5 (1998)

Cantor CR *et al.*, Instrumentation in molecular biomedical diagnostics: an overview, Genetic Analysis (Biomol. Eng.) 14:31-36 (1997)

Certified English translation of European patent 0412883A1, Fast screening and/or identification of a single base on a nucleic acid sequence, including applications.

Certified English translation of Japanese patent 6-294796, Nucleic acid analysis method.

Chrisey *et al.*, Fabrication of patterned DNA surfaces, Nucl. Acids. Res. 24:3040-3047 (1996)

Chrisey *et al.*, Covalent attachment of synthetic DNA to self-assembled monlayer films, Nucl. Acids Res. 24:3031-3039 (1996).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Chu, *Synthesis of an Amplifiable Reporter RNA for Bioassays* 14(14):5591-5603 (1986)

Church et al., "Multiplex DNA Sequencing", Science 240:185-188 (1988).

Covey, et al., The determination of protein, oligonucleotide and peptide molecular weights by ion-spray mass spectrometry, Rapid Comm. Mass Spectrom. 2:249-256 (1988).

Damha, Masad J. et al.; An Improved Procedure for Derivatization of Controlled-Pore Glass Beads for Solid-Phase Oligonucleotide Synthesis; Nucleic Acids Research Vol. 18, No. 13 (1990); pp.3813-3821

Database WPI, Derwent Publications #199502, citing Japanese Patent No. 6294796, Analysing nucleic acids in sample - by adding DNA probes to sample, hybridising and sepg. probes.

Database WPI, Derwent Publication #199015, citing European Patent No. 0360677, Identification of sub-units in complex moles. - by mass spectrometry, especially in nucleic acid sequencing.

Database WPI, Derwent Publication, AN88-311964, JP63230086 A 880926 DW8844, Carry immobilise physiological active substance comprise bind chain form di sulphide compound epoxy group latex contain polymer particle.

Database WPI, Derwent Publications #108350, citing German patent 3221681, Mass spectrometer with external specimen holder - is esp. vor vaporising and ionising sample and has thin polymer foil providing vacuum at entry window Database WPI, Derwent Publications #198942, citing International PCT Application No. WO 89/09406 published 10/05/89

Database WPI, Derwent Publications #198749, citing French patent 2597260, Sample introduction system for mass spectrometry - has table carrying sample series inserted in spectrometer chamber and rotated to present each to source in turn

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Database WPI, Derwent Publications #199043, citing German patent 4011991, Simultaneous sequencing of several DNA samples - by cloning into separate vectors, complementary strand synthesis from specific fluorescent labelled primers, electrophoretic sepn. etc.

Database WPI, Derwent Pulications, citing Japanese patent 2215399, Method for detecting DNA - includes de-naturing to single strand, combining with DNA primer having corresp. base sequence forming replicator etc.

Database WPI, Derwent Publications #199703, citing Japanese Patent No. 8290377 published 11/05/96

Databse WPI, Derwent Publications #199018, citing German patent 3930312, Nucleic acid sequencing - involving amplification-denaturation cycles in presence of deoxy-nucleoside alpha-thio-triphosphate Drmanac, *et al.*, "Sequencing of megabase plus DNA by hybridization: theory of the method", Genomics 4:114-128 (1989).

Eckstein, Nucleoside phosphorothioates, *Ann. Rev. Biochem.* 54:367-402 (1985)

Eckstein, Phosphorothioate analogues of nucleotides, Accounts of Chemical Res., *American Chemical Society* 79:204-210 (1979

Eckstein, *Oligonucleotides and Analogues: A Practical Approach,* Oxford University Press pp. 54-57, pp. 256-259 (1991)

Eckstein, Synthesis and properties of diastereoisomers of adenosine 5'-(O-1-thiotriphosphate) and adenosine 5'-(O-2-thiotriphosphate), *Biochemistry* 15(8):1685-1691 (1976)

Edmonds *et al.*, Thermospray liquid chromatography-mass spectrometry of nucleosides and of enzymatic hydrolysates of nucleic acids, Nucleic Acids Research 13:8197-8206 (1985).

UNITED STATES PATENT AND TRADEMARK OFFICE
CERTIFICATE OF CORRECTION

PATENT NO.    : 6,436,635 B1
DATED         : August 20, 2002
INVENTOR(S)   : Fu et al.

It is certified that error appears in the above-identified patent and that said Letters Patent is hereby corrected as shown below:

OTHER PUBLICATIONS cont'd,

Edmonds, Electrospray ionization mass spectrometry, *Methods in Enzymology* 193:412-431 (1990)

Eggers *et al.*, A microchip for quantitative detection of molecules utilizing luminescent and radioisotope reporter groups, BioTechniques 17:516-524 (1994)

Ehring *et al.*, Photochemical versus thermal mechanisms in matrix-assisted laser desorption/ionization probed by back side desorption, Rapid Comm in Mass Spect 10:821-824 (1996).

Frank, DNA chain length markers and the influence of base composition on electrophoretic mobility of oligodeoxyribonucleotides in polyacrylamide-gels, *Nuc Acids Res.* 6(6):2069-2087 (1979)

Fu *et al.*, Efficient preparation of short DNA sequence ladders potentially suitable for MALDI-TOF DNA sequencing, Genetic Analysis 12:137-142 (1996)

Fu *et al.*, Sequencing double-stranded DNA by strand displacement, *Nucleic Acids Res* 25(3):677-679 (1997)

Fu *et al.*, Sequencing exons 5 to 8 of the p53 gene by MALDI-TOF mass spectrometry, Nat Biotechnol 16:381-4 (1998).

Fu *et al.*, A DNA sequencing strategy which requires only five bases of known terminal sequence for priming, Paper presented, Genome Mapping and Sequencing, Cold Spring Harbor Laboratory.

Fu, *et al.*, "A DNA sequencing strategy that requires only five bases of known terminal sequence for priming (primer extention/stacking interaction/fluorescein/solid state/duplex probe)", Proc. Natl. Acad. Sci. USA 92:10162-10166 (1995).

Fu *et al.*, Sequencing double-stranded DNA by strand displacement, Nucl Acids Res 25:677-679 (1997).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Fujita et al., Surprising lability of biotin-streptavidin bond during transcription of biotinylated DNA bound to paramagnetic beads, BioTechniques 14:608-617 (1993)

Ganem et al., Detection of oligonucleotide duplex forms by ion-spray mass spectrometry, Tetrahedron Letters 34:1445-1448, (1993).

Ghosh, et al., "Covalent attachment of oligonucleotides to solid supports", Nuc. Acids. Res. 15)13):5353-5372 (1987).

Graber et al., Advanced in DNA diagnostics, Curr. Pin. Biotechnol. 9:14 (1998)

Green, Variable-wavelenth on-column fluorescence detector for open-tubular zone electrophoresis, J. of Chromatography 352:337-343 (1986)

Greene and Wuts, Protective Groups in Organic Synthesis, 2nd Edition, Wiley & Sons (1991)

Gross et al., Investigations of the metastable decay of DNA under ultraviolet matrix-assisted laser desorption/ionization conditions with post-source-decay analysis and hydrogen/deuterium exchange, J Amer Soc for Mass Spect 9:866-878 (1998).

Grothues et al., PCR amplification of megabase DNA with tagged random primers (T-PCR), Nuc. Acids Res. 21:1321-1322 (1993)

Gruić-Sovulj I. et al., Matrix-assisted laser desorption/ionisation mass spectrometry of transfer ribonucleic acids isolated from yeast, Nucleic Acids Res. 25(9):1859-61 (1997).

Haglund et al., Marix-assisted laser-desorption mass spectrometry of DNA using an infrared free-electron laser, SPIE 1854:117-128.

Hames, B.D. and Higgins, S.J. ed. Nucleic Acid Hybridization: A Practical Approach, IRL Press: Oxford (1985)

UNITED STATES PATENT AND TRADEMARK OFFICE
CERTIFICATE OF CORRECTION

PATENT NO.     : 6,436,635 B1
DATED          : August 20, 2002
INVENTOR(S)    : Fu et al.

It is certified that error appears in the above-identified patent and that said Letters Patent is hereby corrected as shown below:

OTHER PUBLICATIONS cont'd,

Haralambidis, Preparation of base-modified nucleosides suitable for non-radioactive label attachment and their incorporation into synthetic oligodexribonucleotides, *Nuc Acids Res* 15(12):4857-4876 (1987)

Hayashi, Toshio et al.; Immobilization of Thiol Proteases onto Porous Poly(Vinyl Alcohol) Beads; Polymer Journal Vol. 25, No. 5 (1993); pp.489-497

Heermann, *et al.*, "Liquid-phase hybridization and capture of hepatitis B virus DNA with magnetic beads and fluorescence detection of PCR product", J. of Virol. Methods 50:43-58 (1994).

Higuchi, A general method of in vitro preparation and specific mutagenesis of DNA fragments: study of protein and DNA interactions, *Nuc Acids Res* 16:7351-7367 (1988)

Hillenkamp and Ehring, Laser desorption mass spectrometry Part 1: Basic mechanisms and techniques, Mass Spectrometry in the Biological Sciences: A tutorial, pp. 165-179 (1992).

Hillenkamp *et al.*, Matrix assisted UV-laser desorption/ionization: A new approach to mass spectrometry of large biomolecules, Bio mass Spectr., Burlingame and McCloskey (eds.), pp. 49-61, Elsevier Science Publishers B.V., Amsterdam (1989).

Hobbs, A general method for the synthesis of 2'-azido-2'deoxy-and 2'-amino-2' deoxyribofuranosyl purines, *J. Org. Chem.* 42(4):714-719 (1977)

Hornes and Korsnes, Magnetic DNA hybridization of oligonucleotide probes attached to superparamagnetic beads and their use in the isolation of Poly(A) mRNA from eukaryotic cells, GATA 7:145-150, (1990)

Hsiung *et al.*, A new simpler photoaffinity analogue of peptidyl rRNA, Nucl Acids Res 1:1753-1762 (1974).

Hultman *et al.*, Direct solid phase sequencing of genomic and plasmid DNA using magnetic beads as solid support, Nucl. Acids Res. 17:4937-4946 (1989)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Huth-Fehre, Matrix-assisted laser desorption mass spectrometry of oligodeoxythymidylic acids, *Rapid Comm. in Mass Spectrometry* 6:209-213 (1992)

Hyman, A new method of sequencing DNA, Anal. Biochem. 174:423-436 (1988)

Ikehara, Studies of nucleosides and nucleotides. LXXIX, *Chem. Pharm. Bull.* 26:240-244 (1978)

Imazawa, Facile synthesis of 2'-amino-2'-deoxyribofuranosyl purines, *J. Org. Chem.* 44(12):2039-2041 (1979)

Innis *et al.*, DNA sequencing with *Thermus aquaticus* DNA polymerase and direct sequencing of polymerase chain reaction-amplified DNA, Proc. Natl. Acad. Sci. USA 85:9436-9440 (1988)

Innis *et al.*, editors, PCR Protocols: A guide to methods and applications, Academic Press, San Diego (1990)

Ito T *et al.*, Triplex affinity capture of a single copy clone from a yeast genomic library, Nuc. Acids. Res. 20:3524 (1992)

Ito T *et al.*, Sequence-specific DNA purification by triplex affinity capture, Proc. Natl. Acad. Sci. USA 89:495-498 (1992)

Jacobson, *et al.*, "Applications of mass spectrometry to DNA sequencing", GATA 8(8):223-229 (1991).

Jacobson *et al.*, Applications of Mass Spectrometry to DNA Sequencing, *GATA* No. 8 8(8):223-229 (1991)

Jett *et al.* High-Speed NDA Sequencing: An Approach Based Upon Fluorescense Detection of single Molecules, *J. of Bimolecular Structure & Dynamics*, 7(2):301-309 (1989)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Ji et al., Two-dimensional electrophoretic analysis of proteins expressed by normal and cancerous human crypts: Application of mass spectrometry to peptide-mass fingerprinting, Electrophoresis 15:391-405 (1994).

Juhasz et al., Applications of delayed extraction matrix-assisted laser desorption ionization time-of-flight mass spectrometry to oligonucleotide analysis, Analy Chem 68:941-946 (1996).

Jurinke et al., Recovery of nucleic acids from immobilized biotin-streptavidin complexes using ammonium hydroxide and applications in MALDI-TOF mass spectrometry, Anal. Chem. 69:904-910 (1997).

Jurinke et al., Detection of hepatitis B virus DNA in serum samples via nested PCR and MALDI-TOF mass spectrometry, Genetic Analysis 13:67-71 (1996).

Jurinke et al., Analysis of ligase chain reaction products via matrix-assisted laser desorption/ionization time-of-flight-mass spectrometry, Analy Biochem 237:174-181 (1996).

Jurinke et al., Application of nested PCR and mass spectrometry for DNA-based virus detection: HBV-DNA detected in the majority of isolated anti-HBc positive sera, Genetic Analysis 14:97-102 (1998).

Kelly et al., Enzymatic synthesis of deoxyribonucleic acid, J. of Biological Chemistry 245(1):39-45 (1970)

Kirpekar et al., "7-deaza purine bases offer a higher ion stability in the analysis of DNA by matrix-assisted laser desorption/ionization mass spectrometry" Rapid Commun. Mass Spectrom. 9:525-531 (1995)

Kirpekar et al., DNA sequence analysis by MALDI mass spectrometry, Nucleic Acids Res. 26:2554-9 (1998).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Koster et al., N-Acyl protecting groups for deoxynucleosides, Tetrahedron, 37(2):363-369 (1981)

Koster, Oligonucleotide synthesis and multiplex DNA sequencing using chemiluminescent detection, Nuc Acids Res Symposium Series 24:318-321 (1991)

Köster et al., Some improvements in the synthesis of DNA of biological interest, Nucl Acids Res 7:39-59 (1980).

Köster et al., Polymer support oligonucleotide synthesis--XV$^{1,2}$, Tetrahedron 40:102-112 (1984).

Köster et al., Well-defined insoluble primers for the enzymatic synthesis of oligo- and polynucleotides, Hoppe-Seyler's Z. Physiol. Chem. 359:11579-1589 (1978).

Köster et al., A strategy for rapid and efficient DNA sequencing by mass spectrometry, Nature Biotech. 14:1123-1128 (1996)

Köster et al., MALDI-TOF mass spectrometry - a new paradigm for DNA detection: towards high speed DNA sequencing and diagnostics, Cold Spring Harbor Laboratory.

Kussmann, et al., Matrix-assisted laser desorption/ionization mass spectrometry sample preparation techniques designed for various peptide and protein analytes, J. Mass Spec. 32:593-601 (1997).

Lagerström et al., Capture PCR: efficient amplification of DNA fragments adjacent to a known sequence in human and YAC DNA, PCR Methods and Applications Cold Spring Harbor Lab. Press, 1:111-119 (1991)

Lamture et al., "Direct detection of nucleic acid hybridization on the surface of a charge coupled device", Nucl. Acids Res. 22:2121-2125 (1994).

Landegren et al., "DNA Diagnostics - Molecular techniques and automation", Science 242:229-237 (1988)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Lane et al., The thermodynamic advantage of DNA oligonucleotide 'stacking hybridization' reactions: energetics of a DNA nick, Nuc Acids Res 25(3):611-616 (1997)

Lawrance et al., Megabase-scale mapping of the HLA gene complex by pulsed field gel electrophoresis, Science 235:1387-1389 (1987).

Li et al., "Analysis of single mammalian cell lysates by mass spectrometry", J. Am. Chem. Soc. 118:11662-11663 (1996)

Li et al., High-Resolution MALDI Fourier Transform Mass Spectrometry of Oligonucleotides, Anal Chem 68:2090-2096 (1996).

Lim, Optimal conditions for supercoil DNA sequencing with the excherichia coli DNA polymerase I large fradment, Gene Anal. Techn 5:32-39 (1988)

Liss, Alan R. "Macromolecular sequencing and synthesis selected methods and applications", Edited by David H. Schlesinger, Department of Experimental Medicine and Cell Biology, New York University Medical Center, New York, New York (1988).

Little et al., Detection of RET proto-oncogene codon 634 mutations using mass spectrometry, J. Mol Med. 75:745-750 (1997).

Little et al., Verification of 50- to 100-mer DNA and RNA sequences with high-resolution mass spectrometry, Proc. Natl. Acad. Sci. USA 92:2318-2322 (1995).

Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet", Anal chem 69:4540-4546 (1997).

Little et al., Mass spectrometry from miniaturized arrays for full comparative DNA analysis, Nature Med 3:1413-1416 (1997).

Little et al., Direct detection of synthetic and biologically generated double-stranded DNA by MALDI-TOF MS, J. Mass Spec 17:1-8 (1997).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Little et al., Identification of apolipoprotein E polymorphisms using temperature cycled primer oligo base extension and mass spectrometry, Short Communiation.

Lund, Vera et al.; Assessment of Methods for Covalent Binding of Nucleic Acids to Magnetic Beads, Dynabeads, and the Characteristics of the Bound Nucleic Acids in Hybridization Reactions; Nucleic Acids Research Vol. 16, No. 22 (1988)

Lysov et al., DNA sequencing by hybridisation to oligonucleotide matrix. Calculation of continuous stacking hybridisation efficiency, J Biomolec Struct Dynam., 11(4):797-812 (1994)

Manoharan et al., A 2'-O-thiol tether in the ribose moiety of nucleic acids for conjugation chemistry, Gene, 149:147-156 (1994).

Marshall and Hodgson, "DNA chips: An array of possibilities", Nature Biotechnology 16:27-31 (1998)

Martin, "New technologies for large-genome sequencing", Genome 31:1073-1080 (1989).

Maskos et al., Parallel analysis of oligodeoxyribonucleotide (oligonucleotide) interactions. I Analysis of factors influencing oligonucleotide duplex formation, Nuc Acids Res 20(7):1675-1678 (1992)

Masamune et al., Enzymatic removal and replacement of nucleotides at single strand breaks in deoxyribonucleic acid, J. of biologicla Chemistry 246(8):2680-2691 (1971)

Masamune and Richardson, Strand displacement during deoxyribonucleic acid synthesis at single strand breaks, J. of Biological Chemistry 246(8):2692-2701 (1971)

Matteucci et al., Synthesis of deoxyoligonucleotides on a polymer support, J. A. Chem. Soc. 103:3185-3191, 1981

Matthews, et al., "Analytical strategies for the use of DNA probes", Analytical Biochemistry 169:1-25 (1988).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Maxam, A.M. and Gilbert, W., A new method for sequencing DNA, Proc. Natl. Acad. Sci. USA 74:560-64 (1977)

Maxam and Gilbert, Sequencing end-labeled DNA with base-specific chemical cleavages, Methods in Enzymology 65:499-560 (1980)

McClelland et al., Purification of Mbo II methylase (GAAGmA) from Moraxella bovis: site specific cleavage of DNA at nine and ten base pair sequences, Nucleic Acids Res. 13:7171 (1985)

Mizusawa, Improvement of the dideoxy chain termination method of DNA sequencing by use of deoxy-7-deazaguanosing triphosphate in place of dGTP, Nucleic Acids Res. 14(3):1319-1325 (1986)

Molecular Cloning: A laboratory manual, 2nd, ed., Ch. 11: Synthetic oligonucleotide probes, Sambrook, Cold Spring Harbor Laboratory Press New York, pp. 11.1-11.61 (1989)

Monforte and Becker, High-throughput DNA analysis by time-of-flight mass spectrometry, Nature Medicine 3:360-362 (1997).

Mosca et al., Mass spectrometry and DNA analysis, Hemoglobin 17(3):261-268 (1993).

Murray, "DNA sequencing by mass spectrometry", J. Mass. Spect. 31:1203-1215 (1996).

Nakamaye, Direct sequencing of polymerase chain reaction amplified DNA fragments throught the incorporation of deoxynucleoside α-thiotruphosphates, Nucleic Acids Research, 16(21):9946-9959 (1988)

Nelson, Time-of-Flight Mass Spectrometry of Nucleic Acids by laser Ablation and Ionization from a Frozen Aqueous Matrix, Rapid Communications in Mass Spectrometry, 4(9):348-351 (1990)

Nikiforov et al. "Genetic Bit Analysis: a solid phase method for typing single nucleotide polymorphisms" Nucleic Acids Research, 22(20):4167-4175 (1994).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Nikiforov *et al.*, The use of 96-well polystyrene plates for DNA hybridization-based assays: an evaluation of different approaches tooligonucleotide immobilization, Anal Biochem 227:201-209 (1995).

Nordhoff E. *et al.*, Mass spectrometry of nucleic acids, Mass Spectrometry REviews 15:67-138 (1996)

Nordhoff *et al.*, Ion stability of nucleic acids in infrared matrix-assisted laser desorption/ionization mass spectrometry, Nuc Acids Res. 21:3347-3357 (1993).

Nordoff *et al.*, "Matrix-assisted laser desorption/ionization mass spectrometry of nucleic acids with wavelenght in the ultraviolet and infrared", Rapid Comm. Mass Spectrom. 6:771-776 (1992)

O'Donnell *et al.*, "High-Density, Covalent Attachment of DNA to Siliocn Wafers for Analysis by MALDI-TOF Mass Spectrometry", Analytical Chemistry 69(13):2438-2443 (1997).

O'Donnell *et al.*, MassArray as an enabling technology for the industrial-scale analysis of DNA, Genetic Engineering News 17 (1997).

O'Donnell-Maloney *et al.*, Microfabrication and array technologies for DNA sequencing and diagnostics, Genetic Analysis: Biomolecular Engineering 13:151-157 (1996).

O'Donnell-Maloney *et al.*, The development of microfabricated arrays for DNA sequencing and analysis, Trends in Biotechnology 14:401-407 (1996)

Overberg *et al.*, "Laser desorption mass spectrometry: part II performance and applications of matrix-assisted laser desorption/ionization of large biomolecules", Mass Spect in the Biolog Science: A Tutorial 181-197 (1992).

Perrouault *et al.*, Sequence-specific artificial photo-induced endonucleases based on triple helix-forming oligonucleotides, *Nature* 344:358-360 (1990)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Pieles *et al.*, Matrix-assisted laser desorption ionization time-of-flight mass spectrometry: a powerful tool for the mass and sequence analysis of natural and modified oligonucleotides, Nucleic Acids Res. 21:3191-3196 (1993).

Pitulle *et al.*, Initiator oligonucleotides for the combination of chemical and enzymatic RNA synthesis, *Gene* 112:101-105 (1992)

Pomerantz *et al.*, Determination of oligonucleotide composition from mass spectrometrically measured molecular weight, Am. Soc. Mass Spectrom. 4:204-09 (1993).

Pon, Richard T. et al.; Research Report: Derivatization of Controlled Pore Glass Beads for Solid Phase Oligonucleotide Synthesis; BioTechniques Vol. 6, No. 8 (1988); pp.768-770, 773-775

Prober *et al.*, A System for Rapid DNA Seqencing with Fluorescent Chain-Terminating Dideoxynucleotides, *Science* 238:238-341 (1987)

Prome *et al.*, Use of combined mass spectrometry methods for the characterization of a new variant of human hemoglobin: The double mutant hemoglobin villeparisis beta 77(EF1), J. American Society for Mass Spect 7(2):163-167 (1996).

Rasmussen *et al.*, "Covalent immobilization of DNA onto polystyrene microwells: The molecules ar eonly bound at the 5' end", Anal. Biochem. 198:138-142 (1991).

Rink, "Solid-phase synthesis of protected peptide fragments using a trialkoxy-diphenyl-methlester resin", Tetrahedron Lett. 28:3787-3790 (1987).

Rolfs *et al.*, PCR: Clinical Diagnostics and Research, Springer- Verlag (1992)

Running and Urdea, A procedure for productive coupling of synthetic oligonucleotides to polystyrene microtiter wells for hybridization capture, Biotechniques 8:276-277 (1990)

Ruppert *et al.*, A rapid and high throughput method for plasmid isolations, Presented: Automation in Mapping and DNA Sequencing Conference, Aug. 31 - Sept. 2 1994

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Ruppert et al., Preparation of plasmid DNA as sequencing templates in a microtiter plate format, Paper presented, Cold Spring Harbor Laboratory.

Ruppert et al., A filtration method for plasmid isolation using microtiter filter plates, Anal. Biochem. 230:130-134 (1995).

Ruth, Oligodeoxynucleotides with reporter Groups Attached to the Base, Oligonucleotides and Analogues: A Practical Approach (Dekstein, F.Ed.) IRL Press, Oxford 255-281 (1991)

Saiki et al., Genetic analysis of amplified DNA with immobilized sequence-specific oligonucleotide probes, Proc. Natl. Acad. Sci. 86:6230-6234 (1989)

Sanger, F. et al., DNA sequencing with chain-terminating inhibitors, Proc. Natl. Acad. Sci. USA 74:5463-67 (1977)

Sano et al., Immuno-PCR: very sensitive antigen dtection by means of specific antibody-DNA conjugates, Science 258:120-122 (1992)

Sano et al., Immuno-PCR, In The Encyclopedia of Molecular Biology and Biotechnology, Robert A. Meyers, ed., VCH Publishers Inc., New York City, N.Y., 4:288-295 (1996)

Sano et al., Identification of multiple structural domains regulating viroid pathogenicity, Proc. Natl. Acad. Sci. USA 89:10104-10108 (1992)

Sano, T., and Cantor, C.R., A streptavidin-protein a chimera that allows one-step production of a variety of specific antibody conjugates, Bio/Technology 9:1378-81 (1991)

Sano T and Cantor CR, Expression vectors for streptavidin-containing chimeric proteins, Biochem and Biophys Res Comm. 176:571-577 (1991)

Schneider K et al., Increased stability ofnucleic acids containing 7-deaza-guanosine and 7-deaza-adenosine may enable rapid DNA sequencing by matrix-assisted laser desorption spectroscopy, Nucleic Acids Res. 23(9):1570-75 (1995)

UNITED STATES PATENT AND TRADEMARK OFFICE
CERTIFICATE OF CORRECTION

PATENT NO.    : 6,436,635 B1
DATED         : August 20, 2002
INVENTOR(S)   : Fu et al.

It is certified that error appears in the above-identified patent and that said Letters Patent is hereby corrected as shown below:

OTHER PUBLICATIONS cont'd,

Schram, Karl H., "Mass Spectrometry of Nucleic Acid Components", Bio Appl of Mass Spect. 34:203-287 (1990).

Schran, Mass Spectrometry of Nucleic Acid Components, *Biomedical Applications of Mass Spectrometry*, 34:203-287 (1990)

Seela, 98.1, 7-Dideaza-2'3'-dideoxyadenosine: Syntheses of Pyrrolo [2,3-b]pyridine 2',3'-Dideoxyribofuranosides and Participation of Purine N(1) during HIV-1 Reverse Transcriptase Inhibition, *Helvetica Chimica Acta* - 74:1048-1058 (1991)

Sequenom Signs Agreement With Bruker-Franzen Analytik to Develop Mass Spectrometer for DNA Massarray Analysis, Press Release: Jan. 12, 1998, http://www.sequenom.com/pressrelease.htm.

Sequenom Reports On Use of Its DNA MassArray™Technology to Analyze Genes Associated with Alzheimer's Disease adn Arteriosclerosis: Technology Has Applications in Drug Development, Press Release: Sept. 22, 1997, http://www.sequenom.com/pressrelease.htm.

Sequenom Uses DNA MassArray™to Sequence Section of Human Cancer-Related p53 Gene", Press Release: Mar. 27, 1998, http://www.sequenom.com/pressrelease.htm.

Sequenom Advances the Industrial Genomics Revolution with the Launch of Its DNA MassArray™Automated Process Line, Press Release: Sept. 28, 1998, http://www.sequenom.com/pressrelease.htm.

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Shaler *et al.*, Effect of Impurities on the matrix-assisted laser desorption mass spectra of single-stranded oligodeoxynucleotides, Anal. Chem. 68:576-579 (1996).

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Siegert et al., Matrix-assisted laser desorption/ionization time-of-flight mass spectrometry for the detection of polymerase hain reaction products containing 7-deasapurine moieties, Anal. Biochem. 243:55-65 (1996).

Singh et al., Oligonucleotides, part 5+: synthesis and Fluorecence studies of NDA oligomers d(AT)5 containing adenines covalently linked at C-8 with dansyl fluorophore. Nucleic Acids Research 18(11):3339-3345 (1990)

Sinha et al., β-cyanoethyl N, N-dialkylamino/N-morpholinomonochloro phosphoamidites, new phosphitylating agents facilitating ease of deprotection and work-up of synthesized oligonucleotides, Tetrahedron Lett. 24:5843-5846 (1983).

Sinha et al., Polymer support oligonucleotides synthesis AVIII: use of β-cyanoethyl-N,N-dialkylamino-ln-morpholino phosphoramidite of deoxynucleosides for the synthesis of FNA fragments simplifying deprotection and isolation of the final product, Nuc Acids Res 12(11):4539-4558 (1984)

Sinha et al., Polymer support oligonucleotide synthesis XVIII: use of β-cyanoethyl-N,N-dialkylamino-/N-morpholino phosphoramidite of deoxynucleosides for the synthesis of DNA fragments simplyfying deprotection and isolation of the final product, Nucleic Acids Res. 12:4539-4557 (1984)

Siuzdak, The emergence of mass spectrometry in biochemical research, Proc. Natl. Acad. Sci. USA 91:11290-11297 (1994).

Slim et al., Configurationally defined phosphorothioate-containing oligoribonucleotides in the study of the mechanism of cleavage of hammerhead rybozymes, Nuc Acids Res, 19(6):1183-1188 (1991)

Smith CL et al., Preparation and manipulation of large DNA molecules: advances and applications, TIBS 12:284 (1987)

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

OTHER PUBLICATIONS cont'd,

Smith *et al.*, Capillary zone electrophoresis-mass spectrometry using an electrospray ionization interface, Anal. Chem. 60:436-441 (1988).

Smith CL *et al.*, Evolving strategies for making physical maps of mammalian chromosomes, Genome 31:1055 (1989)

Smith *et al.*, Fluorescence detection in automated DNA sequence analysis, *Nature* Vol. 321, 674-679 (1986)

Southern, E.M., Analyzing and comparing nucleic acid sequences by hybridization to arrays of oligonucleotides: evaluation using experimental models, *Genomics* 13:1008-1017 (1992)

Sowa *et al.*, The facile synthesis of 5'-nucleotides by the selective phosphorylation of a primary hydroxyl group of nucleosides with phosphoryl chloride, Bulletin of the Chemical Society of Japan 48(7):2084-2090 (1975)

Sproat *et al.*, 2'-O-methyloligoribonucleotides: synthesis and applications, *Oligonucleotides and Analogues: A Practical Approach* (Eckstein, F. ed.) IRL Press, Oxford, pp. 49-86 (1991)

Sproat *et al.*, The synthesis of protected 5'-mercapto-2,5'-dideoxyribonucleoside-3')-phosphoramidites; uses of 5'-mercapto-oligodeoxyribonucleotides, *Nuc Acids Res* 15(12):4837-4848 (1987)

Sproat *et al.*, The synthesis of protected 5'-amino-2',5'-dideoxyribonucleoside-3'-O-phosphoramidites; applications of 5'-amino-oligodeoxyribonucleotides, Nucleic Acids Res. 15(15):6181-6196 (1987)

Stahl *et al.*, Solid Phase DNA Sequencing using the Biotin-Avidin System, Nucleic Acids Research, vol. 16, No. 7, pp. 3024-3039 (1988)

Still *et al.*, Rapid chromoatographic technique for preparative separations with moderate resolution, *J. Org. Chem.* 43(14):2923-2925 (1978)

UNITED STATES PATENT AND TRADEMARK OFFICE
CERTIFICATE OF CORRECTION

PATENT NO.    : 6,436,635 B1
DATED         : August 20, 2002
INVENTOR(S)   : Fu et al.

It is certified that error appears in the above-identified patent and that said Letters Patent is hereby corrected as shown below:

OTHER PUBLICATIONS cont'd,

Stratagene Catalog, p. 39 (1988)

Stratagene Catalog, Synthetic Oligonucleotides, p. 106 (1992)

Strezoska, et al., "DNA sequencing by hybridization: 100 bases read by a non-gel-based method", Proc. Natl. Acad. Sci. USA 88:10089-10093 (1991).

Stults and Marsters, "Improved electrospray ionization of synthetic oligodeoxynucleotides", Rapid Comm. Mass Spectrom. 5:359-363 (1991).

Swerdlow et al., Capillary gel electrophoresis for rapid, high resolution DNA sequencing, Nuc Acids Res 18(6):1415-1419 (1990)

Tang et al., Matrix-assisted laser desorption/ionization mass spectrometry of immobilized duplex DNA probes, Nucleic Acids Research 23:3126-3131 (1995).

Tang, et al., Improving mass resolution in MALDI/TOF analysis of DNA.

Tang et al., Detection of 500-nucleotide DNA by laser desorption mass spectrometry, Rapid Commun. Mass Spectrom. 8:727-730 (1994)

Tomer et al., "Coaxial Continuous Flow Fast Atom Bombardment for Higher-Molecular-Weight Peptides: Comparison with Static Fast Atom Bombardment and electrospray Ionization", Bio Mass Spect 20:783-788 (1991).

Tong et al., Solid-phase method for the purification of DNA sequencing reactions, Anal. Chem. 64:2672-2677, (1992)

Trainor, "DNA Sequencing, Automation, and the Human Genome", Anal. Chem. 62:418-426 (1990).

Valaskovic, et al., Attomole-sensitivity electrospray source for large-molecule mass spectrometry, Anal. Chem. 67:3802-3805 (1995).

UNITED STATES PATENT AND TRADEMARK OFFICE
CERTIFICATE OF CORRECTION

PATENT NO.    : 6,436,635 B1
DATED         : August 20, 2002
INVENTOR(S)   : Fu et al.

It is certified that error appears in the above-identified patent and that said Letters Patent is hereby corrected as shown below:

OTHER PUBLICATIONS cont'd,

Verheyden *et al.*, Synthesis of some pyrimidine 2'-amino-2'-deoxynucleosides, *J. Org. Chem.* 36(2):250-254 (1971)

Vorm *et al.*, Improved resolution and very high sensitivity in MALDI TOF of matrix surfaces made by fast evaportion, Anal. Chem. 66:3281-3287 (1994).

Wang, Solid phase synthesis of protected peptides via photolytic cleavage of the α-methylphenacyl ester anchoring linkage, J. Org. Chem. 41(20):3258-3261 (1976)

Wetmur, DNA probes: applications of the principles of nucleic acid hybridization, *Critcal Rev in Biochem and Molec Biol* 26(3/4):227-259 (1991)

Williams, Time of flight mass spectrometry of DNA laser-ablated from frozen aqueous solutions: applications to the Human Genome Project, Intl. J. Mass Spectrom. and Ion Processes 131:335-344 (1994)

Wu *et al.*, Matrix-assisted Laser Desorption Time-of-flight Mass Spectrometry of Oligonucleotides Using 3-Hydroxypicolinic Acid as an Ultraviolet-sensitive Matrix, Rapid Comm Mass Spec 7:142-146 (1993).

Wu *et al.*, "Time-of-Flight Mass Spectrometry of Underivatized Single-Stranded DNA Oligomers by Matrix-Assisted Laser Desorption", Anal. Chem. 66:1637-1645 (1994).

Yates, III, Mass spectrometry and the age of the proteome, J. Mass Spec. 33:1-19 (1998).

Zhu Y *et al.*, DNA sequence analysis of human chromosome 21 not I linking clones, Genomics 18(2):199-25 (1993)

Zimmermann *et al.*, Automated preparation and purification of M13 templates for DNA sequencing, Meth. Mol. Cell. Biol. 1:29-34 (1989)

Zuckermann *et al.*, Efficient methods for attachment of thiol specific probes to the 3'-ends of synthetic oligodeoxyribonucleotides, Nucleic Acids Research, 15:13, 5305-5321 (1987).--

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Column 1,
Lines 6-14, replace,

"This application is a continuation-in-part of United States patent application, serial number 08/420,009, filed April 11, 1995, now abandoned which is a continuation-in-part of United States patent application, serial number 08/110,691, filed August 23, 1993, now U.S. patent No. 5,795,714 which is a continuation-in-part of United States patent application serial number 07/972,012, filed November 6, 1992, now abandoned; and United States patent application, serial number 419,994, filed April 11, 1995, now abandoned which is a continuation-in-part of United States patent application, serial number 08/001,323, filed January 7, 1993, now abandoned." with —This application is a continued prosecution application of U.S. Serial No. 08/614,151, filed March 12, 1996, which is a continuation-in-part of U.S. application, Serial No. 08/420,009, filed April 11, 1995, to Cantor, entitled Solid Phase Sequencing of Nucleic Acids, which is a continuation-in-part of U.S. application, Serial No. 08/110,691, filed August 23, 1993, to Cantor et al., entitled Method for Replicating an Array of Nucleic Acid Probes, now U.S. Patent No. 5,795,714, issued August 18, 1998, which is a continuation-in-part of U.S. application Serial No. 07/972,012, filed November 6, 1992, to Cantor, entitled Position Sequencing by Hybridization, now abandoned.—

Lines 16-22, please delete "Rights in the Invention This invention was made with United States Government support under grant number DE-FG-02-93ER61609, awarded by the United States Department of Energy, and the United States Government has certain rights in the invention."

Column 3,
Line 15, please replace "to" with -- too --
Line 31, between "conditions" and "ultimately" please insert -- are --
Line 31, please replace "this s the" with -- this is the --
Line 39, please replace "publication" with -- publications --

Column 6,
Line 33, after "between" please delete "particle the"
Lines 62-63, please remove the paragraph separation between "target constructed." and "Nucleic acids"

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Column 8,
Line 8, after "fragments" please delete "complexes"

Figure 18A:
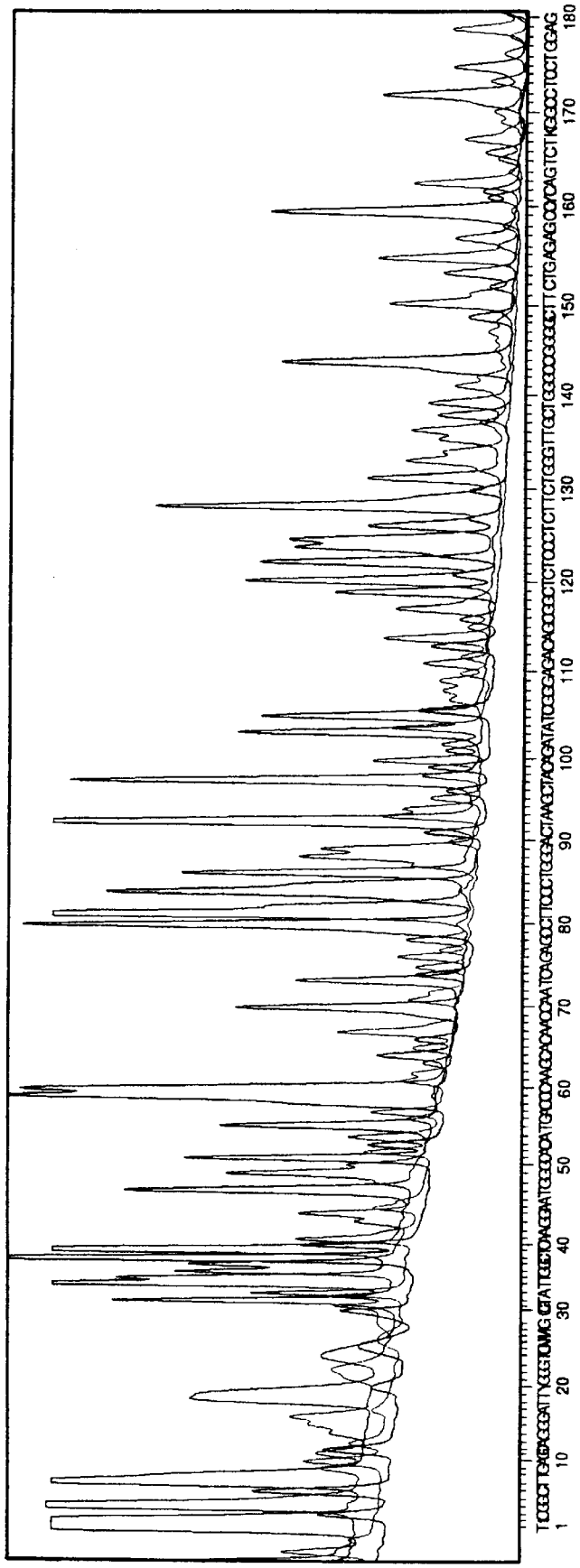
FIG. 18 Analysis of sequencing reaction in the presence and absence of single-stranded DNA binding protein.
Figure 18B:
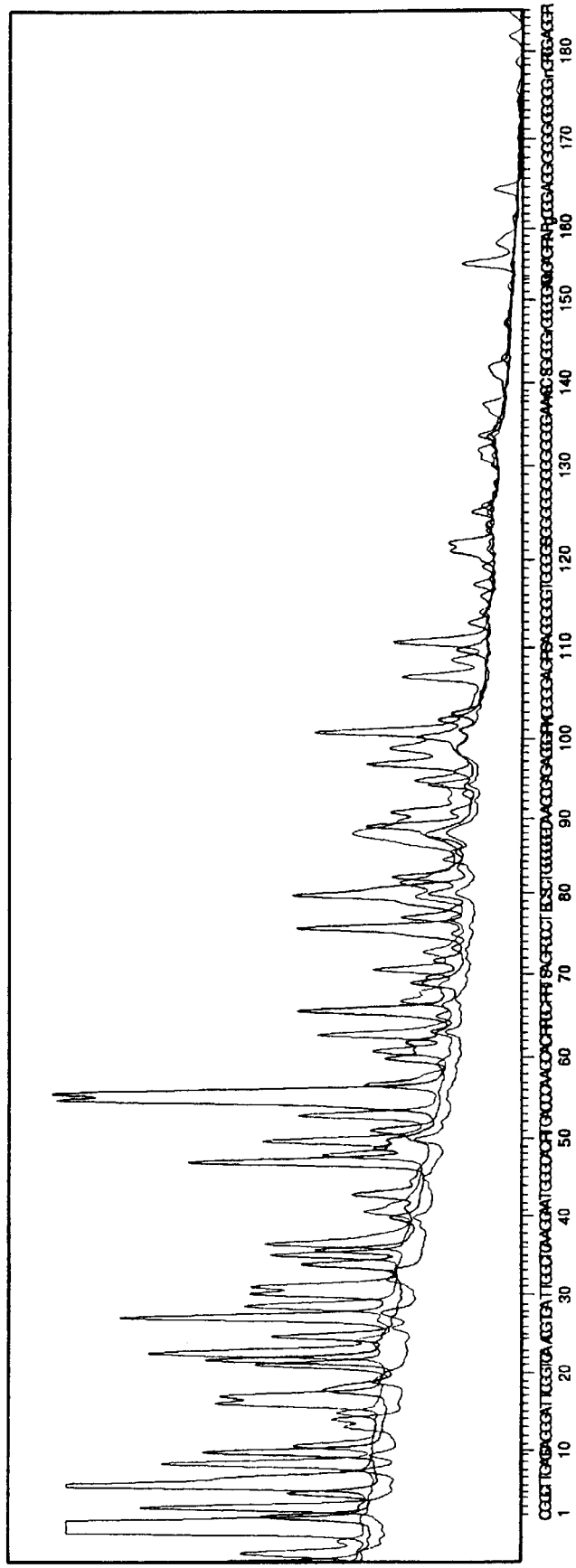
Figure 20A:
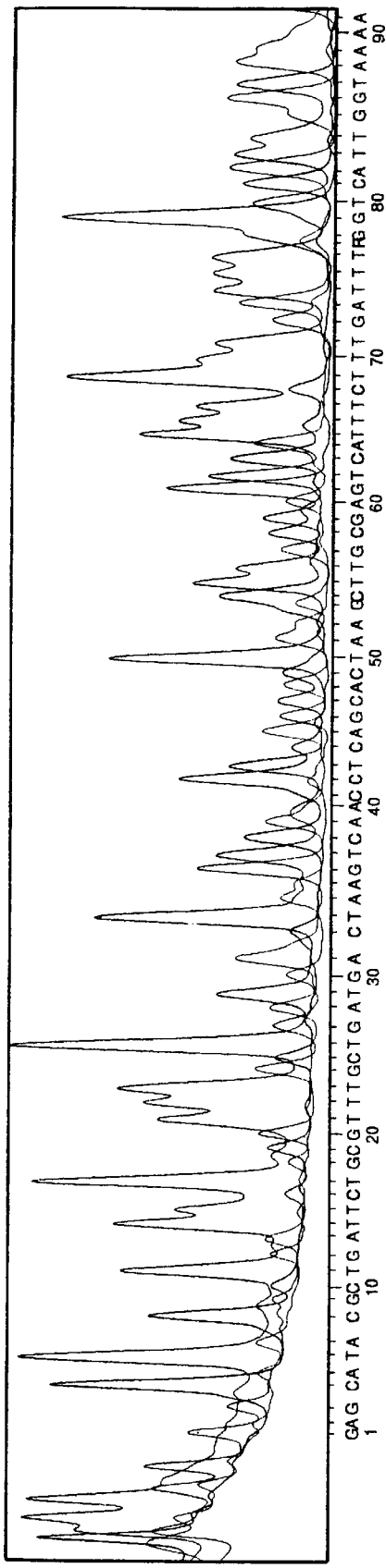
FIG. 20 Results of sequencing performed using DF27-1 as a probe.
Figure 20B:
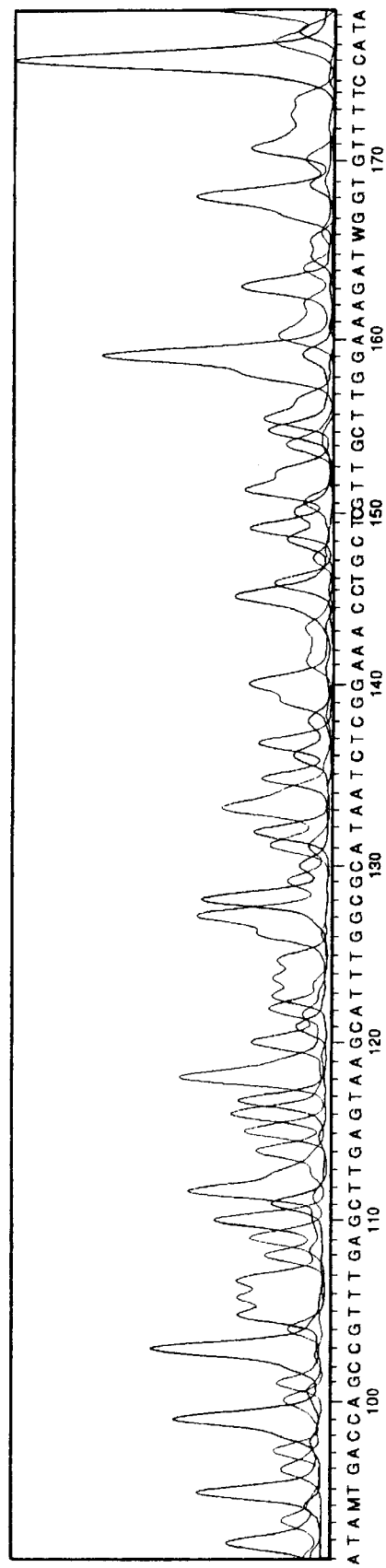
Figure 20C:
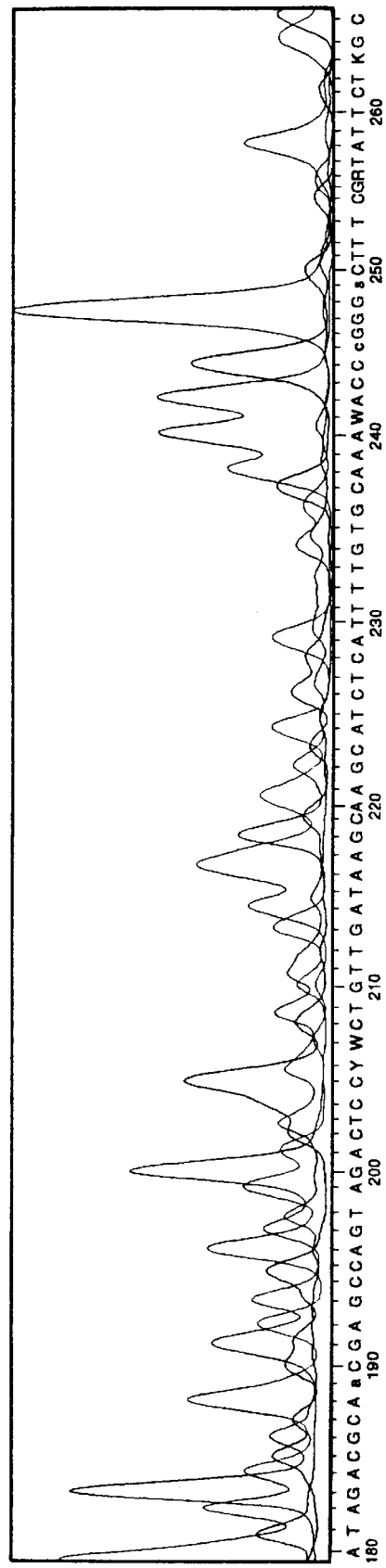
Figure 21A:
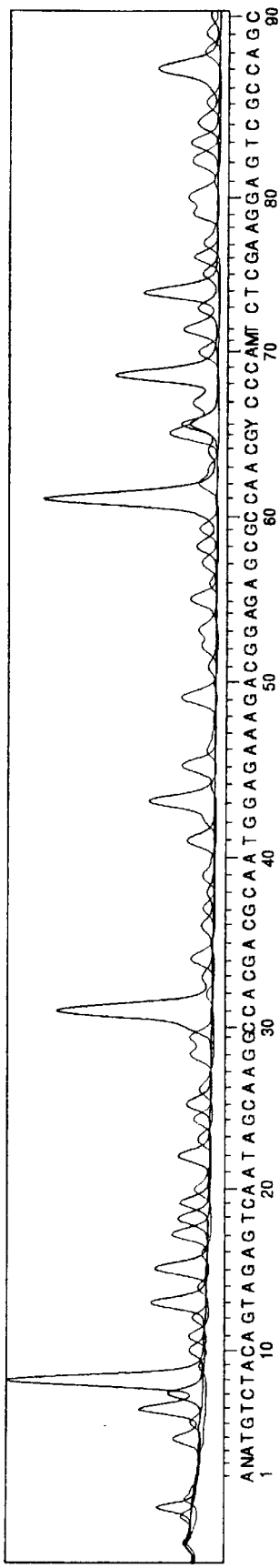
FIG. 21 Results of sequencing performed using DF27-2 as a probe.
Figure 21B:
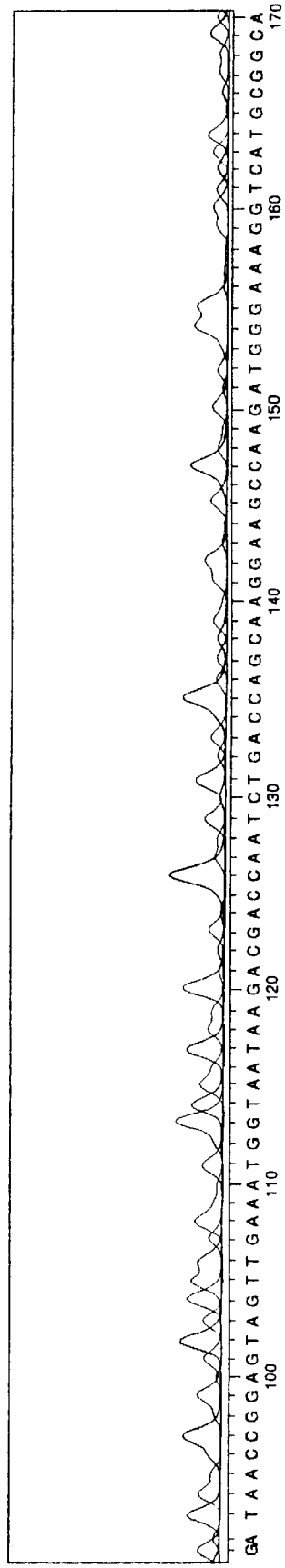
Figure 2I:
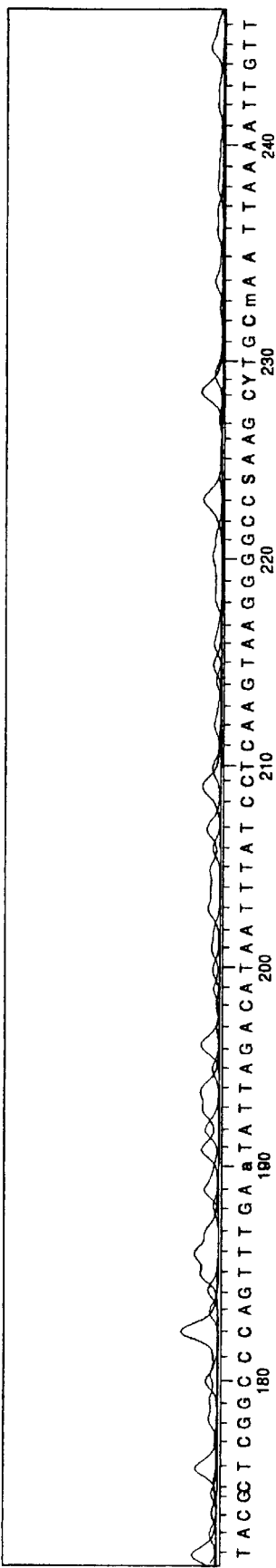
FIG. 2 (A) Schematic of mass modified nucleoside triphosphate elongators and terminators; and (B) nucleoside triphosphate mass modification moieties.
Figure 2I:
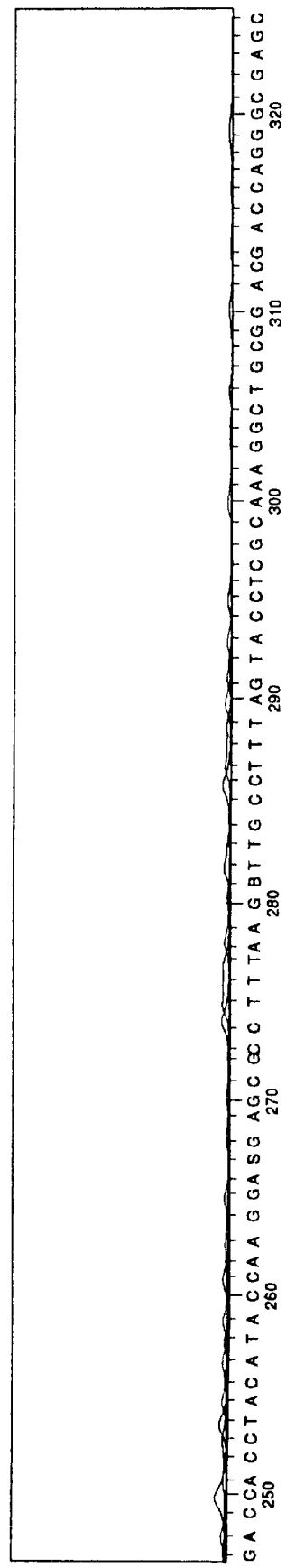
Figure 22A:
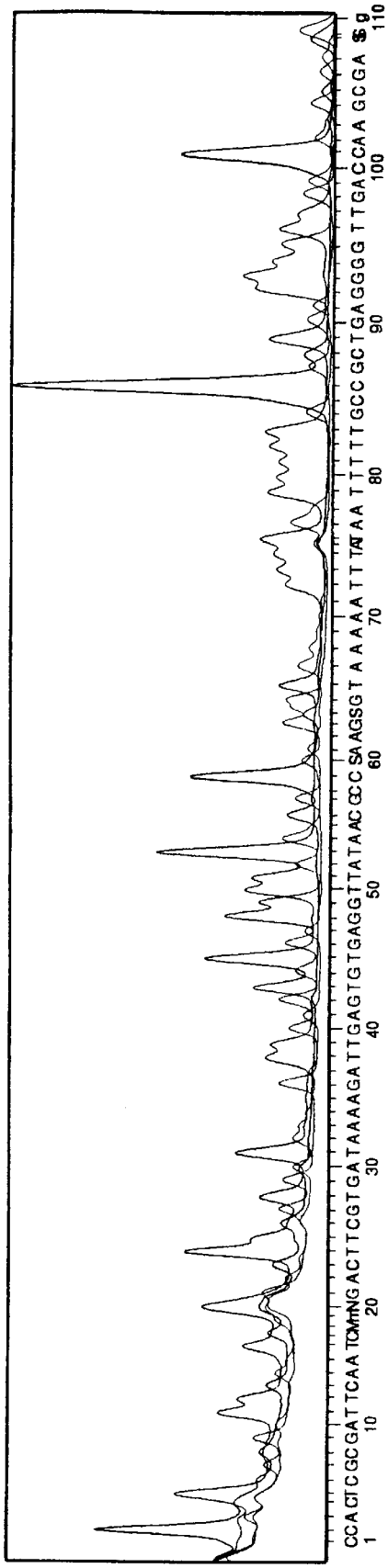
FIG. 22 Results of sequencing performed using DF27-4 as a probe.
Figure 22B:
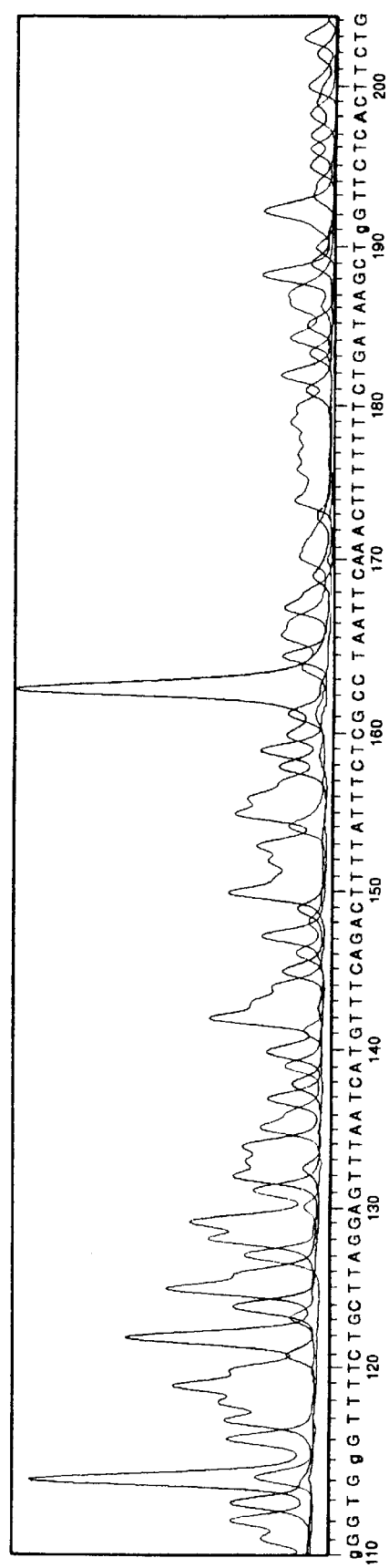
Figure 22C:
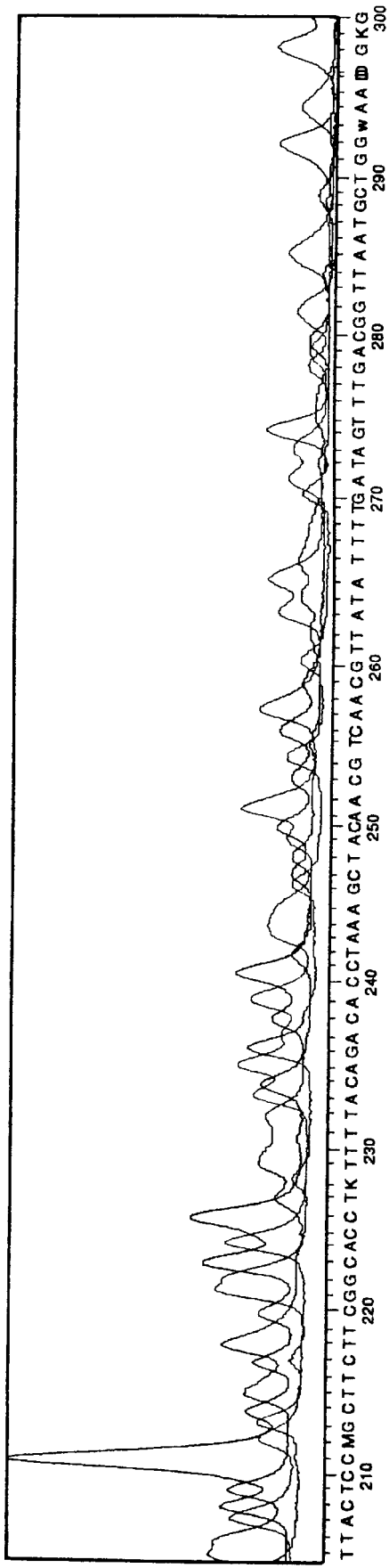
Figure 23A:
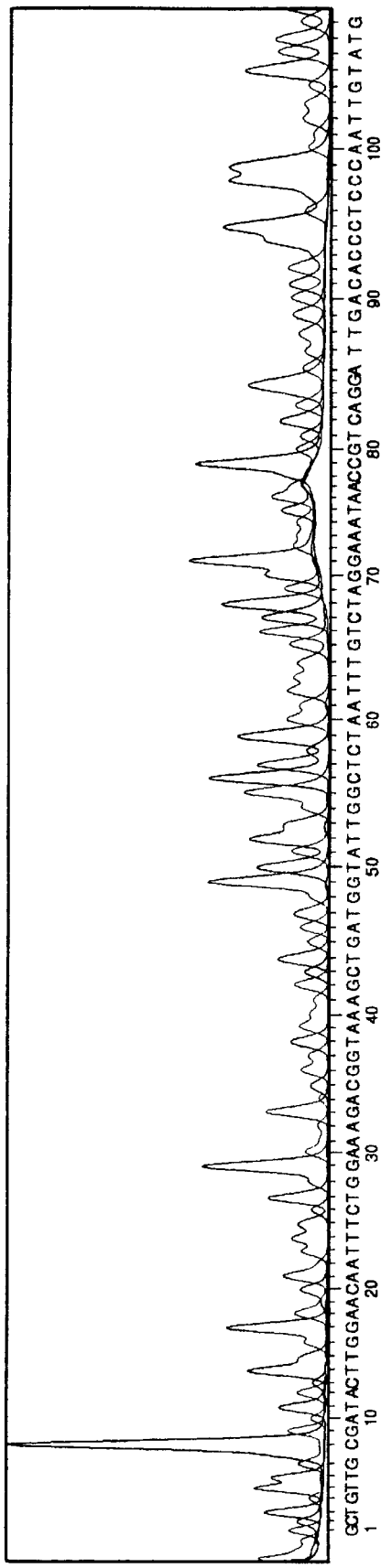
FIG. 23 Results of sequencing performed using DF27-5-CY5 as a probe.
Figure 23B:
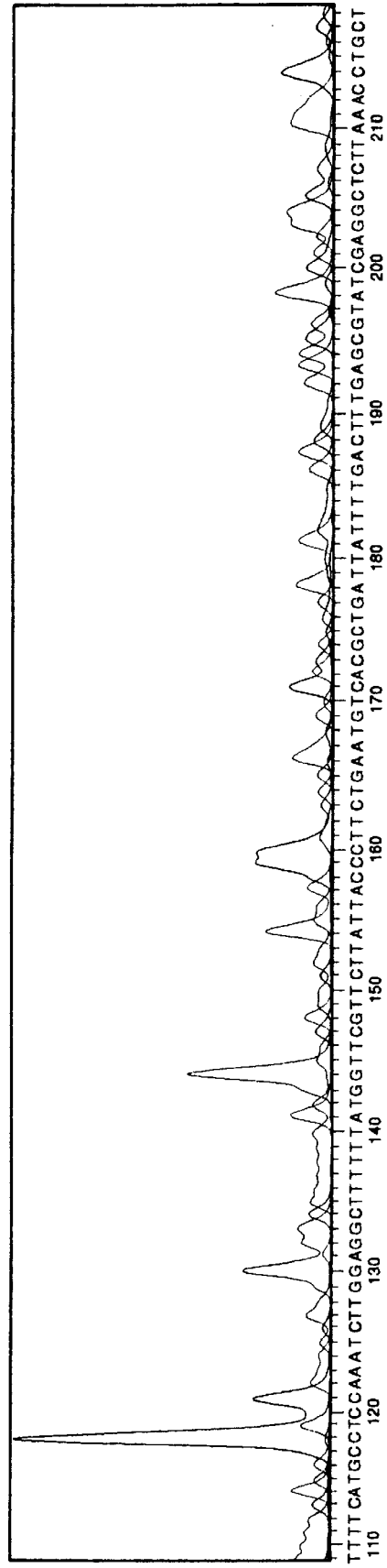
Figure 23C:
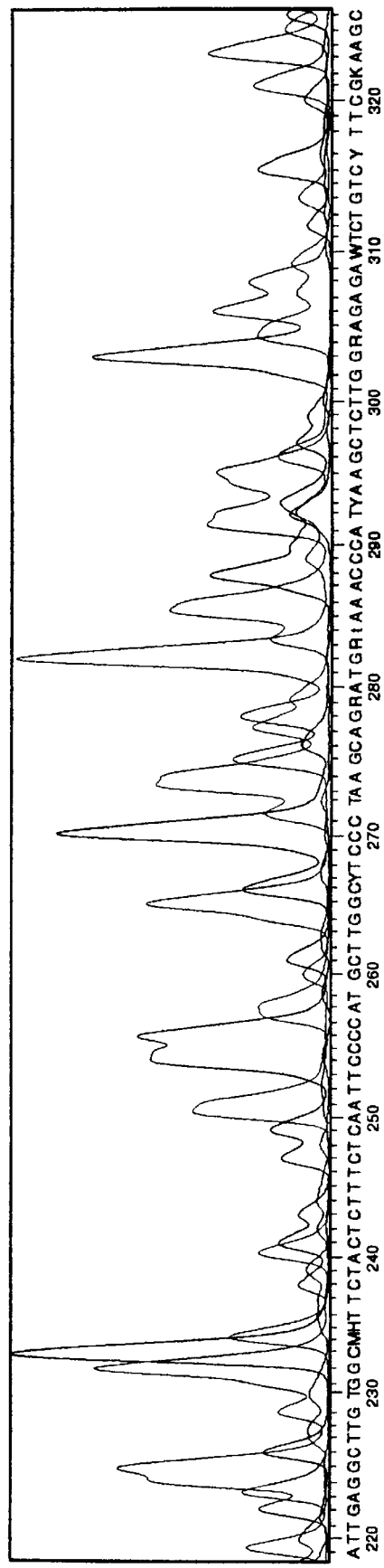
Figure 24A:
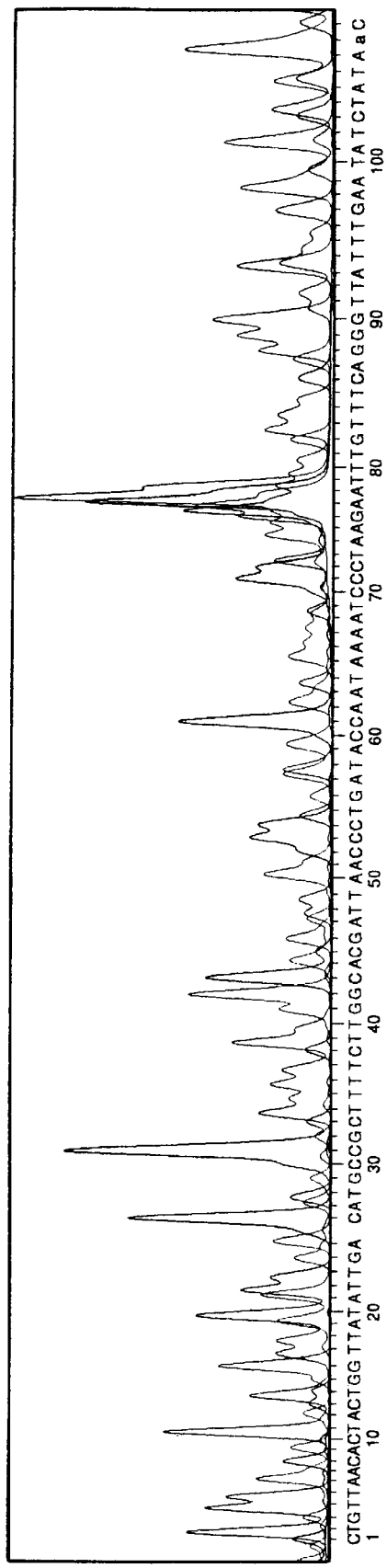
FIG. 24 Results of sequencing performed using DF27-6-CY5 as a probe.
Figure 24B:
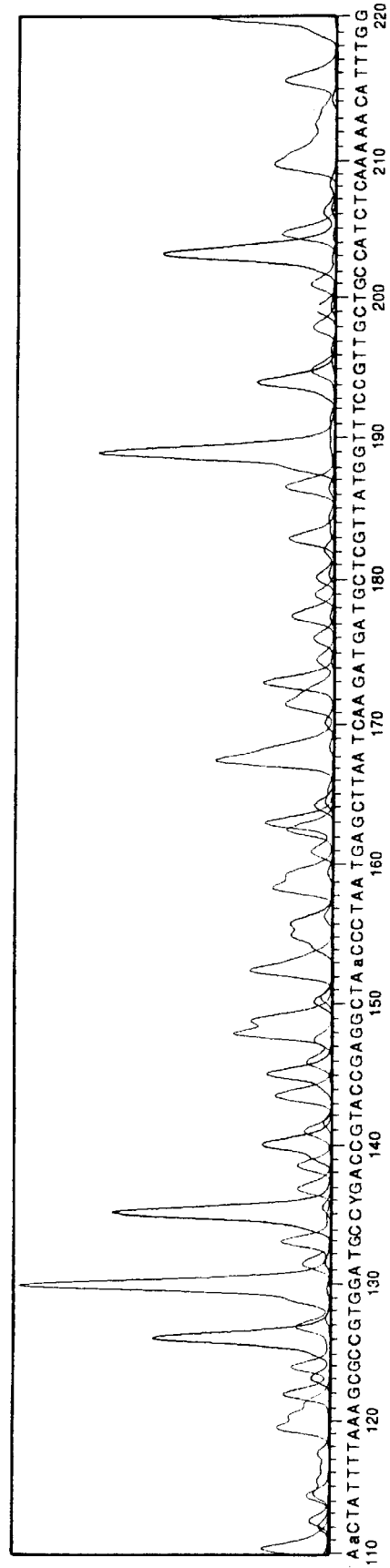
Figure 24C:
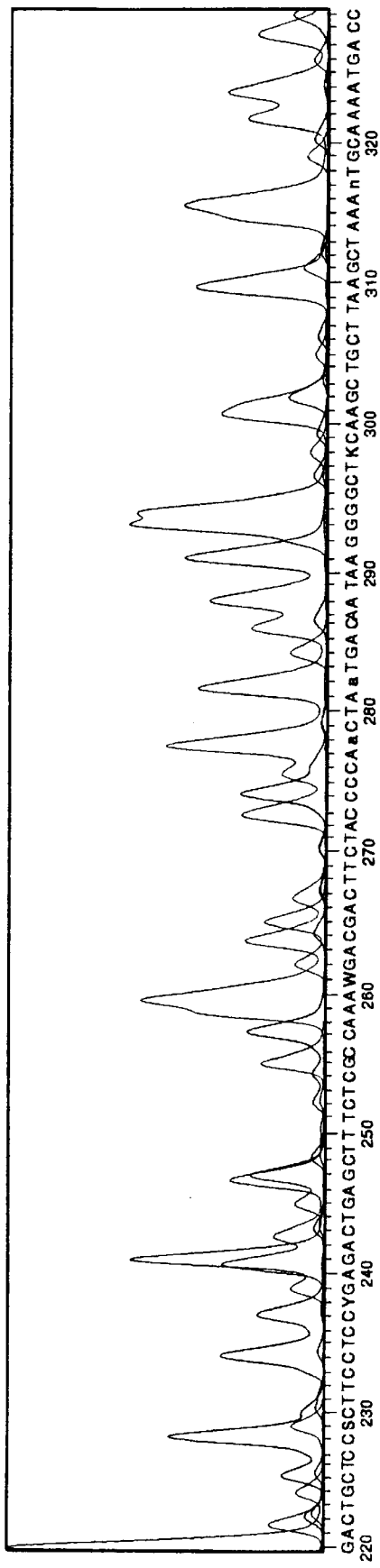

Column 9,
Line 10, please replace "FIG. 13" with -- FIGS. 13A-13J --
Line 20, please replace "FIG. 18" with -- FIGS. 18A-18B --
Line 24, please replace "FIG. 20" with -- FIGS. 20A-20C --
Line 27, please replace "FIG. 21" with -- FIGS. 21A-21D --
Line 29, please replace "FIG. 22" with -- FIGS. 22A-22C --
Line 31, please replace "FIG. 23" with -- FIGS. 23A-23C --
Line 33, please replace "FIG. 24" with -- FIGS. 24A-24C --
Line 52, please replace "be" with -- being --
Line 66, please replace "an" after "be"

Column 10,
Line 13, replace "array" with -- arrays --
Line 45, replace "includes" with -- include --

Column 12,
Line 45, please replace "common one" with -- one common --

Column 15,
Lines 31-34, replace "fluorescein, iododicarbocyanine dye, SiR, $Si(CH_3)_3$, $Si(CH_3)_2$ $(C_2H_5)$, $Si(CH_3)_2(CH_5)_2$, $Si(CH_3)(C_2H_5)_2$, $Si(C_2H_5)_3$, $(CH_2)_nCH_3$, $(CH_2)_nNR$, $CH_2CONR$, $(CH_2)_nOH$, $CH_2F$, $CHF_2$, and $CF_3$;" with -- $SiR_3$, $Si(CH_3)_3$, $Si(CH_3)_2$ $(C_2H_5)$,$Si(CH_3)(C_2H_5)_2$, $Si(C_2H_5)_3$, $(CH_2)_nCH_3$, $(CH_2)NR_2$, $CH_2CONR_2$, $(CH_2)_nOH$, $CH_2F$, $CHF_2$, and $CF_3$; --
Lines 41-45, please replace "the mass-modifying functionality is generated from a precursor functionality which is —$N_3$ or—XR, wherein X is: —OH, —$NH_2$, —NHR, —SH, —NCS, —OCO$(CH_2)_n$COOH, —NHCO$(CH_2)_n$COOH, —OSO$_2$OH, —OCO$(CH_2)$ $_n$I, or —OP(O-alkyl)-N-alkyl)$_2$," with -- Mass modifying functionalities, may also be —$N_3$ or —XR, wherein X is: —O—, —NH—, —NR—, —S—, —NHC(S)—, —OCO$(CH_2)_n$COO—, —NHCO$(CH_2)_n$COO—, —OSO$_2$O—, —OCO$(CH_2)_n$—, —OP(O-alkyl)—, —NHC(S)NH—, —OCO$(CH_2)_n$S—, —OCO$(CH_2)$S—, $NC_4O_2H_2S$—, —OPO(O-alkyl)—,— --
Line 55, please replace "acids" with -- acid --

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Column 16,
Line 33, after "nucleic" please insert -- acids --
Line 34, please replace "simply" with -- simple --
Line 40, please delete "contacting by"

Column 18,
Line 21, please replace "5002,868" with -- 5,002,868 --

Column 19,
Line 17, between "have" and successfully" please insert -- been --

Column 22,
Line 21, please replace "well-know" with -- well-known --
Line 43, please replace "5´-temeni" with -- 5´-termini --
Line 43, please replace "3´-temeni" with -- 3´-termini --

Column 23,
Line 47, please replace "small" with -- smaller --
Line 60, please replace "individual" with -- individually --

Column 24,
Line 13, please replace "an array" with -- arrays --

Column 25,
Line 1, please delete "from"
Line 6, please insert -- ordinary -- between "each" and double-stranded"
Line 14, please replace "sequence" with -- sequences --
Line 37, please replace "from" with -- form --
Line 53, after "ladder" please replace "and" with -- which --
Line 54, please replace "sequencing where" with -- sequencing, where --
Line 61, please replace "sequence" with -- sequences --

Column 26,
Lines 6 and 8, please replace " A biotin" with -- Biotin --
Line 14, please replace "reaction This" with -- reaction. This --

Column 27,
Line 35, please replace "used as" with -- used, as --
Line 66, please replace "Any unoccupied" with -- Unoccupied --

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Column 28,
Line 33, please replace "3-aminopropyltrieshoxysilane" with
-- 3-aminopropyltriethoxysilane --

Column 29,
Line 6, please replace "functionality was" with -- functionality, was --

Column 30,
Lines 35-36, please remove the paragraph separation between "double stranded sequencing." and "For single stranded"

Column 31,
Line 19, replace "as then" with -- was then --
Line 51, please replace "discrimination other" with -- discrimination, other --

Column 32,
Line 19, please replace "nucleic also minimize" with -- nucleic acid may also minimize --
Line 24, please replace "method" with -- methods --

Column 34,
Line 31, please replace "(SEQ ID NO 2)" with -- (SEQ ID NO 35) --

Column 35,
Line 6, please replace "(SEQ ID NO 2)" with -- (SEQ ID NO 35) --
Line 8, please delete "(SEQ ID NO 2)"
Line 51, please replace "FIG. 13" with -- FIG. 13A-13J --

Column 36,
Line 7, please replace "Target TS12" with -- Target TS10 -- in reaction 9
Line 40, please replace "DNA" with -- DNA) --
Line 63, please replace "40 mM McCl$_2$" with -- 40 mM MgCl$_2$ --

Column 37,
Line 23, please replace "(40 mM" with -- 40mM --
Line 32, please replace "5 minutes room temperature" with -- 5 minutes, room temperature --
Line 50, please replace "droplet. the silicon array surfaces is ideal for" with -- droplet. Silicon array surfaces are ideal for --

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Column 38,
Line 41, please replace "Comparison" with -- By comparison --
Line 43, please insert -- , -- between "nucleotide" and "the nucleic acid"

Column 40,
Line 11, please replace "5-(3-aminopropynyl-l)-2´deoxyuridine" with
-- 5-(3-aminopropynyl-1)-2´-deoxyuridine --

Column 43,
Line 14, please replace "bond" with -- bonds --

Column 44,
Line 4, please replace "Aglycyl glycine" with -- A glycyl glycine --

Column 45,
Lines 66-67, please replace "8-glycly– and 8-glycyl-glycyl-2´.3´-dideoxyadenosine-5´-triphosphates" with -- 8-glycyl– and 8-glycyl-glycyl-2´,3´-dideoxyadenosine-5´-triphosphates --

Column 46,
Line 9, please replace "15:1685, 1976) and Accounts Chem. Res. 12:204, 1978) and" with -- 15:1685, 1976 and Accounts Chem. Res. 12:204, 1978 and --

Column 47,
Line 18, please replace "d(TAAAACGACGGCCAGUG)" with
-- d(UAAAACGACGGCCAGUG) --
Line 46, please replace "5´-AACAGCTATFACCATG-3´" with
-- 5´-AACAGCTATGACCATG-3´ --
Line 65, please replace "incubation" with -- incubated --

Column 48,
Line 15, please replace "paring" with -- pairing --

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

<u>Column 49,</u>
Line 6, please replace "(FIG. 18, bottom panel)" with -- (FIG. 18B) --
Line 31, please replace "(FIG. 18, top panel)" with -- (FIG. 18A) --
Line 60, please replace "incubation" with -- incubated --

<u>Column 50,</u>
Line 53, please replace "nucleotides" with -- nucleotide --

Signed and Sealed this

Sixth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,436,635 B1
DATED : August 20, 2002
INVENTOR(S) : Fu et al.

It is certified that error appears in the above-identified patent and that said Letters Patent is hereby corrected as shown below:

Title page,
Item [63], Related U.S. Application Data, please replace "Continuation-in-part of application number 08/420,009, filed on April 11, 1995, now abandoned, which is a continuation-in-part of application number 08/110,691, filed on August 23, 1993, now Pat. Num. 5,795,714, which is a continuation-in-part of application number 07/972,012, filed on November 6, 1992; now abandoned." with -- This application is a continuation-in-part of and claims benefit of priority to U.S. Application Serial No. 08/420,009, filed April 11, 1995 (now abandoned). U.S. Application Serial No. 08/420,009 is related to U.S. application Serial No. 08/110,691, filed on August 23, 1993, now U.S. Pat. No. 5,795,714, as a continuation-in-part. U.S. application Serial No. 08/420,009 is a continuation-in-part of U.S. application serial No. 07/972,012, filed on November 6, 1992; now abandoned. --

Column 1,
Lines 6-14, replace "This application is a continued prosecution application of U.S. Serial No. 08/614,151, filed March 12, 1996, which is a continuation-in-part of U.S. application, Serial No. 08/420,009, filed April 11, 1995, to Cantor, entitled Solid Phase Sequencing of Nucleic Acids, which is a continuation-in-part of U.S. application, Serial No. 08/110,691, filed August 23, 1993, to Cantor et al., entitled Method for Replicating an Array of Nucleic Acid Probes, now U.S. Patent No. 5,795,714, issued August 18, 1998, which is a continuation-in-part of U.S. application Serial No. 07/972,012, filed November 6, 1992, to Cantor, entitled Position Sequencing by Hybridization, now abandoned." with -- This application is a continuation-in-part of and claims benefit of priority to U.S. Application Serial No. 08/420,009, filed April 11, 1995 (now abandoned). U.S. Application Serial No. 08/420,009 is related to U.S. application Serial No. 08/110,691, filed on August 23, 1993, now U.S. Pat. No. 5,795,714, as a continuation-in-part. U.S. Application Serial No. 08/420,009 is a continuation-in-part of U.S. application serial No. 07/972,012, filed on November 6, 1992; now abandoned. --

Signed and Sealed this

Ninth Day of September, 2003

JAMES E. ROGAN
*Director of the United States Patent and Trademark Office*